(12) United States Patent
Cameron et al.

(10) Patent No.: US 11,998,655 B2
(45) Date of Patent: Jun. 4, 2024

(54) COLLAGEN BIOMATERIALS AND METHODS FOR MANUFACTURING COLLAGEN BIOMATERIALS

(71) Applicant: Cambridge Enterprise Limited, Cambridge (GB)

(72) Inventors: Ruth Elizabeth Cameron, Cambridge (GB); Serena Michelle Best, Cambridge (GB); David James Barrett, Cambridge (GB); Matthew Linley, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 574 days.

(21) Appl. No.: 17/056,391

(22) PCT Filed: May 17, 2019

(86) PCT No.: PCT/EP2019/062818
§ 371 (c)(1),
(2) Date: Nov. 17, 2020

(87) PCT Pub. No.: WO2019/219916
PCT Pub. Date: Nov. 21, 2019

(65) Prior Publication Data
US 2021/0187156 A1 Jun. 24, 2021

(30) Foreign Application Priority Data
May 18, 2018 (GB) ...................................... 1808106

(51) Int. Cl.
*A61L 24/10* (2006.01)
*A61L 24/00* (2006.01)
(Continued)

(52) U.S. Cl.
CPC ......... *A61L 24/102* (2013.01); *A61L 24/0015* (2013.01); *A61L 27/24* (2013.01);
(Continued)

(58) Field of Classification Search
CPC .............................. A61L 27/24; C25D 13/04
See application file for complete search history.

(56) References Cited

U.S. PATENT DOCUMENTS 4,264,422 A  4/1981 Funabashi et al.
9,724,308 B2 8/2017 Paukshto et al.
(Continued)

FOREIGN PATENT DOCUMENTS

EP    2845612 A1 * 3/2015 ............. A61L 27/20
JP    S-55-158292 A  12/1980
(Continued)

OTHER PUBLICATIONS

Ammam. Electrophoretic deposition under modulated electric fields: a review. RSC Advances, 2012, 2, 7633-7646 (Year: 2012).*
(Continued)

*Primary Examiner* — Cachet I Proctor
(74) *Attorney, Agent, or Firm* — HAMILTON, BROOK, SMITH & REYNOLDS, P.C.

(57) ABSTRACT

This invention relates to collagen biomaterials and methods for manufacturing collagen biomaterials. Method disclosed herein include steps of providing a suspension of insoluble collagen fibres, providing a layer deposition interface and applying an electric field across the suspension to cause electrophoretic deposition of the insoluble collagen fibres at the layer deposition interface. Biomaterials disclosed herein include a layer comprising an array of fibres of collagen, and a layered composite material comprising at least first and second fibrous layers each comprising an array of fibres of collagen, and a shape adapting layer sandwiched between (Continued)

the first and second fibrous layers. Biomaterials as described herein may be useful in a range of tissue engineering and other applications.

18 Claims, 31 Drawing Sheets

(51) Int. Cl.
    *A61L 27/24*     (2006.01)
    *A61L 27/50*     (2006.01)
    *A61L 27/54*     (2006.01)

(52) U.S. Cl.
    CPC .............. *A61L 27/507* (2013.01); *A61L 27/54* (2013.01); *A61L 2420/08* (2013.01)

(56) References Cited

U.S. PATENT DOCUMENTS

| | | | | |
|---|---|---|---|---|
| 2004/0002055 | A1* | 1/2004 | Andre ................ | G01N 33/5085 435/4 |
| 2007/0142916 | A1* | 6/2007 | Olson, Jr. ............. | A61L 27/58 623/23.23 |
| 2009/0312524 | A1* | 12/2009 | Lauritzen .............. | A61K 38/17 530/356 |
| 2010/0248368 | A1* | 9/2010 | Lynn ...................... | A61L 27/56 435/407 |
| 2010/0311949 | A1 | 12/2010 | Akkus et al. | |
| 2011/0168558 | A1* | 7/2011 | Fransaer ................ | C09D 5/448 204/477 |
| 2011/0282448 | A1 | 11/2011 | Paulos et al. | |
| 2012/0015003 | A1* | 1/2012 | Gleeson .................. | A61P 19/00 424/400 |
| 2013/0071645 | A1* | 3/2013 | Park ........................ | A61L 27/24 428/318.6 |
| 2014/0193477 | A1 | 7/2014 | Chaikof et al. | |
| 2014/0242140 | A1 | 8/2014 | Neu et al. | |
| 2014/0242347 | A1* | 8/2014 | Paukshto ............ | A61L 27/3808 428/221 |
| 2018/0002672 | A1* | 1/2018 | Allbritton ............ | C12N 5/0679 |

FOREIGN PATENT DOCUMENTS

| | | | | |
|---|---|---|---|---|
| JP | 2003-534102 | A | 11/2003 | |
| JP | 2012-187926 | A | 10/2012 | |
| WO | WO-2005120631 | A1 * | 12/2005 | ............... A61N 1/05 |
| WO | WO-2011028977 | A1 * | 3/2011 | ............. A61L 27/24 |
| WO | 2013/071062 | A1 | 5/2013 | |
| WO | WO 2019/219916 | A2 | 11/2019 | |

OTHER PUBLICATIONS

Seuss et al. Electrophoretic Deposition of Biological Macromolecules, Drugs, And Cells. Biomacromolecules. 2013 (Year: 2013).*
Baker et al. Electrically Controlled Growth and Positioning of Suspended Collagen Membranes. Langmuir 2008, 24, 7, 2970-2972:Mar. 7, 2008 (Year: 2008).*
Hasan et al. Sacrificial layer electrophoretic deposition of freestanding multilayered nanoparticle films. Chem. Commun., 2009, 3723-3725 (Year: 2009).*
Partial International Search Report issued in Application No. PCT/EP2019/062818, dated Aug. 12, 2019.
European Examination Report issued in European Application No. 19725150.7, dated Oct. 10, 2022.
Japanese Office Action dated Mar. 28, 2023, issued in Application No. 2020-564316 (With English Translation).
Albayrak, O. et al., "Hydroxyapatite coating on titanium substrate by electrophoretic deposition method: Effects of titanium dioxide inner layer on adhesion strength and hydroxyapatite decomposition," *Surf. Coatings Technol.*, vol. 202, pp. 2482-2487, Feb. 2008.

Badylak, S.F. et al., "The use of xenogeneic small intestinal submucosa as a biomaterial for Achilles tendon repair in a dog model.", *J. Biomed. Mater. Res.* 29 977-85, 1995.
Benzoni, P. et al., "Biomanufacturing of a Chitosan/Collagen Scaffold to Drive Adhesion and Alignment of Human Cardiomyocyte Derived from Stem Cells," *Procedia CIRP*, vol. 49, pp. 113-120, 2016.
Besra, L. and M. Liu, "A review on fundamentals and applications of electrophoretic deposition (EPD)," *Prag. Mater. Sci.*, vol. 52, No. 1, pp. 1-61, 2007.
Besra, L. et al., "Application of constant current pulse to suppress bubble incorporation and control deposit morphology during aqueous electrophoretic deposition (EPD)," *J. Eur. Ceram. Soc.*, vol. 29, pp. 1837-1845, Jul. 2009.
Besra, L. et al., "Bubble-Free Aqueous Electrophoretic Deposition (EPD) by Pulse-Potential Application," *J. Am. Ceram. Soc.*, vol. 91, pp. 3154-3159, Oct. 2008.
Brown et al, "Ultrarapid Engineering of Miomimetic Materials and Tissues: Fabrication of Nano- and Microstructures by Plastic Compression," *Adv Funct Mater*, 15 1762-1770, 2005.
Caubert, F. et al., "Innovating pulsed electrophoretic deposition of boehmite nanoparticles dispersed in an aqueous solution, into a model porous anodic film, prepared on aluminium alloy 1050," *Surf. Coatings Technol.*, vol. 302, pp. 293-301, 2016.
Cheng, X. et al., "An electrochemical fabrication process for the assembly of anisotropically oriented collagen bundles," *Biomaterials*, vol. 29, No. 22, pp. 3278-3288, 2008.
Frajkorová, F. et al., "Biodegradable bi-layered coatings shaped by dipping of Ti films followed by the EPD of gelatin/hydroxyapatite composites," *J. Eur. Ceram. Soc.*, vol. 36, pp. 343-355, Jan. 2016.
Girman, Jan, University of Cambridge, Department of Materials Science Metallurgy, Degree Granting Institution, "Novel Treatments for Spinal Facet Arthrosis," 288 pages, 2016.
Göncü, Y. et al., "Electrophoretic deposition of hydroxyapatitehexagonal boron nitride composite coatings on Ti substrate," *Mater. Sci. Eng. C*, vol. 79, pp. 343-353, Oct. 2017.
Hasan, S.A. et al., "Transferable Graphene Oxide Films with Tunable Microstructures," *ACS Nano*, 4, 12, 7367-7372, 2010.
Jiang, T. et al., "Surface functionalization of titanium with chitosan/gelatin via electrophoretic deposition: characterization and cell behavior.," *Biomacromolecules*, vol. 11, pp. 1254-1260, May 2010.
Kumar, V. A. et al., "Collagen based substrates with tunable strength for soft tissue engineering," *Biomater. Sci.*, vol. 1, No. 11, p. 1193-1202, 2013.
Li, W.-W. et al., "A novel chitosan hydrogel membrane by an improved electrophoretic deposition and its characteristics in vitro and in vivo," *Mater. Sci. Eng. C*, vol. 74, pp. 287-297, May 2017.
Mazloomi, K. et al., "Electrical Efficiency of Electrolytic Hydrogen Production," *Int. J. Electrochem. Sci*, vol. 7, pp. 3314-3326, 2012.
Nečas, D. and P. Klapetek, "Gwyddion: an open-source software for SPM data analysis," *Cent. Eur. J. Phys*, vol. 10, No. 1, pp. 181-188, 2012.
Neirinck, B. et al., "Aqueous electrophoretic deposition in asymmetric AC electric fields (AC-EPD)," *Electrochem. commun.*, vol. 11, pp. 57-60, Jan. 2009.
Nold, A. and R. Clasen, "Bubble-free electrophoretic shaping from aqueous suspension with micro pointelectrode," *J. Eur. Ceram. Soc.*, vol. 30, pp. 2971-2975, Oct. 2010.
Panduranga Rao, K., "Recent developments of collagen-based materials for medical applications and drug delivery systems," *J. Biomater. Sci. Polym. Ed.*, vol. 7, pp. 623-645, Jan. 1996.
Pang, X. and I. Zhitomirsky, "Electrophoretic deposition of composite hydroxyapatite-chitosan coatings," *Mater. Charact.*, vol. 58, No. 4, pp. 339-348, 2007.
Perumal, V. A. et al., "Investigating a New Approach to Film Casting for Enhanced Drug Content Uniformity in Polymeric Films," *Drug Dev. Ind. Pharm.*, vol. 34, pp. 1036-1047, Jan. 2008.
Raju, K. and D. Yoon, "Electrophoretic deposition of BaTiO3 in an aqueous suspension using asymmetric alternating current," *Mater. Lett.*, vol. 110, pp. 188-190, Nov. 2013.
Sakurada, O. et al., "Bubble-free electrophoretic deposition of aqueous zirconia suspensions with hydroquinone," *J. Mater. Sci.*, vol. 39, pp. 1845-1847, Mar. 2004.

(56) References Cited

OTHER PUBLICATIONS

Schofield, J.D. et al., "The Isolation, and Amino Acid and Carbohydrate Composition of Polymeric Collagens Prepared from Various Human Tissues" *Biochem. J.* 124, 467-473, 1971.

Sculean, A. et al., "Soft tissue wound healing around teeth and dental implants.," *J. Clin. Periodontal.*, vol. 41 (Suppl 15), pp. S6-22, Apr. 2014.

Steven, F.S. "The effect of chelating agents on collagen interfibrillar matrix interactions in connective tissue", *Biochim. Biophys. Acta*, 140, 522-528, 1967.

Steven, F.S. et al, "Polymeric collagen isolated from the human intestinal submucosa", *Gut*, 10, 484-487, 1969.

Tabellion, J. and R. Clasen, "Electrophoretic deposition from aqueous suspensions for near-shape manufacturing of advanced ceramics and glasses applications," *J. Mater. Sci.*, vol. 39, pp. 803-811, Feb. 2004.

Uchikoshi, T. et al., "Dense, bubble-free ceramic deposits from aqueous suspensions by electrophoretic deposition," *J. Mater. Res.*, vol. 16, pp. 321-324, Feb. 2001.

Webster, V. A. et al., "Effect of actuating cell source on locomotion of organic living machines with electrocompacted collagen skeleton," *Bioinspir. Biomim.*, vol. 11, p. 036012, May 2016.

Webster, V. A. et al., "Fabrication of Electrocompacted Aligned Collagen Morphs for Cardiomyocyte Powered Living Machines," in Cont. Biomim. Biohybrid Syst. Living Mach. 2015 Biomim. Biohybrid Syst., pp. 429-440, Springer International Publishing, 2015.

Wu, L.-Q. et al., "Voltage-Dependent Assembly of the Polysaccharide Chitosan onto an Electrode Surface," *Langmuir*, vol. 18, pp. 8620-8625, Oct. 2002.

Xiao, X. F. and R. F. Liu, "Effect of suspension stability on electrophoretic deposition of hydroxyapatite coatings," *Mater. Lett.*, vol. 60, pp. 2627-2632, Sep. 2006.

Youncsi, M. et al., "Fabrication of compositionally and topographically complex robust tissuc forms by 3D-electrochemical compaction of collagen," *Biofabrication*. Jun. 12, 2015; 7(3):035001. doi: 10.1088/1758-5090/7/3/035001.

Younesi et al. "Tenogenic Induction of Human MSCs by Anisotropically Aligned Collagen Biotextiles", *Adv Funct Mater*. Sep. 24, 2014; 24(36): 5762-5770. doi: 10.1002/adfm.201400828.

Zhang, J. et al., "Effect of the addition CNTs on performance of CaP/chitosan/coating deposited on magnesium alloy by electrophoretic deposition," *Mater. Sci. Eng. C*, vol. 58, pp. 992-1000, Jan. 2016.

Zhitomirsky, I. and L. Gal-or, "Electrophoretic deposition of hydroxyapatite," *J. Mater. Sci. Mater. Med.*, vol. 8, pp. 213-219, Apr. 1997.

Weber et al., "Application of binary buffer systems to free flow cell electrophoresis," *Electrophoresis*, 21: 325-328, 2000.

PCT International Search Report and Written Opinion for International Application No. PCT/EP2019/062818, titled "Collagen Biomaterials And Methods For Manufacturing Collagen Biomaterials," dated Nov. 21, 2019.

UK Search Report for GB Application No. 1808106.7, titled "Collagen Biomaterials And Methods For Manufacturing Collagen Biomaterials," dated Nov. 9, 2018.

Barrett et al., "Free standing collagen films prepared by electrophoretic deposition," Front. Bioeng. Biotechnol. Conference, Abstract: 10th World Biomaterials Congress, pp. 1-2. Retrieved from the Internet on Jul. 23, 2019; https://www.frontiersin.org/10.3389/conf.FBIOE.2016.01.02753/2893/10th_World_Biomaterials_Congress/all_events/event_abstract.

Gigante et al.,"Collagen I Membranes for Tendon Repair: Effect of Collagen Fiber Orientation on Cell Behavior," Journal of Orthopaedic Research, pp. 826-832 (Jun. 2009).

Hasan et al., "Sacrificial layer electrophoretic deposition of freestanding multilayered nanoparticle films," Royal Society of Chemistry, Chem. Comm., pp. 3723-3725 (2009).

Isobe et al., "Oriented Collagen Scaffolds for Tissue Engineering," Materials, 5: 501-511 (2012).

Ma et al., "Electrophoretic Deposition of Hyaluronic Acid and Composite Films for Biomedical Applications," JOM, 62, No. 6, pp. 72-75 (Jun. 2010).

Seuss et al., "Electrophoretic Deposition of Biological Macromolecules, Drugs, And Cells," BioMacromolecules, ACS Publications, 14, 3355-3369 (2013).

Torbet et al., "Orthogonal scaffold of magnetically aligned collagen lamellae for corneal stroma reconstruction," Biomaterials 28: 4268-4276 (2007).

Baker et al., "Electrochemically Controlled Growth and Positioning of Suspended Collagen Membranes," Langmuir, 24: 2970-2972 (2008).

Boccaccini et al., "Electrophoretic deposition of biomaterials," J. R. Soc. Interface, 7: S581-S613 (2010).

\* cited by examiner (a)

(b)

COLLAGEN BIOMATERIALS AND METHODS FOR MANUFACTURING COLLAGEN BIOMATERIALS

This application is the U.S. National Stage of International Application No. PCT/EP2019/062818, filed May 17, 2019, which designates the U.S., published in English, and claims priority under 35 U.S.C. § 119 or 365(c) to Great Britain Application No. 1808106.7, filed May 18, 2018. The entire teachings of the above International Applications are incorporated herein by reference.

FUNDING

The work leading to this invention has received funding from the European Research Council under the European Union's Seventh Framework Programme (FP7/2007-2013)/ERC grant agreement number 320598.

FIELD

The present invention relates to collagen biomaterials and methods for their manufacture.

BACKGROUND

Collagen, one of the most abundant proteins found in vertebrates has been widely used in a number of forms as a biomaterial as it has a low immunogenicity, high biocompatibility, and can act as a scaffold for cell proliferation and wound healing.

Native collagen may be harvested directly from animal tissues and is strong and highly organised. Small intestinal submucosa (SIS) for example has been widely used as a biomaterial [1]. However, native collagen tissue does not contain cells and cannot be easily engineered or tailored to specific requirements.

The major fraction of most collagen tissue is insoluble triple helical collagen (also term polymeric collagen; PC) which is composed of naturally cross-linked tropocollagen in the form of large diameter collagen fibrils. Polymeric collagen may be purified from native collagen tissue by swelling the polymer at low pH into a clear solution/suspension, and then re-condensing/re-aggregating the collagen fibres by neutralisation [2, 3, 4].

Monomeric collagen is composed of isolated collagen triple helices and is soluble. Gels may be generated through the fibrillogenesis (gelling) of soluble monomeric collagen. These gels are relatively weak, with random fibril organisation. However, biomimetic materials have been prepared by the plastic compression of collagen gels [5].

Collagen membranes produced by solvent casting and air drying have been used as biomaterials in a range of applications, such as wound dressings [6], guided tissue regeneration [7], and barrier layers [8]. However, solvent casting however requires extensive drying times, even layer production can be difficult at scale, and there can be uneven loading of incorporated drugs leading to undesirable release profiles [9].

Collagen membranes have been produced from solutions of soluble monomeric collagen using an electric field by a process of electrochemical compaction. In some reported methods, the monomeric collagen migrates to the isoelectric point, where fibrillogenesis is induced to produce collagen fibres or films. In other reported methods, monomeric collagen migrates to an electrode where fibrillogenesis is induced [38].

SUMMARY

The present inventors have realised that it would be advantageous to manufacture dense, reproducible collagen layers (such as membranes). It is advantageous if such layers have controllable, preferably even, thickness. It is further advantageous if such layers can be produced at dimensions and/or shapes to suit different requirements.

Electrophoretic deposition (EPD) is a colloidal processing method widely used in ceramic processing as a rapid, low cost, scalable, and highly reproducible technique for producing coatings and free standing films that is currently being explored for use in polymer and biological systems such as chitosan [10, 11, 12, 13, 14, 15] and hydroxyapatite [14, 16, 17, 18, 19, 20] using aqueous suspension media. There have been a small number of papers that have examined the effects of an electric field on collagen monomers [21, 22, 23, 24], however to the knowledge of the inventors at the time of writing there have been no reports on the production of films or coatings from polymeric collagen by EPD.

While most EPD of ceramic systems uses organic liquids as a suspension medium, allowing for high applied potentials, EPD of biomaterials requires use of a non-toxic suspension medium, such as an aqueous system [25]. The use of aqueous suspension media in EPD is associated with a number of problems, particularly the electrolysis of water. When a potential above 1.23V at 25° C. is applied across an aqueous liquid, electrolysis typically occurs, leading to the release of hydrogen and oxygen gas at the cathode and anode respectively [26]. The evolution of these gasses at the electrodes cause bubbles to form which disturb the deposit as it forms, damaging it and reducing the rate of deposition, and which can become trapped within the deposit [27]. A number of different approaches have been used to avoid gas evolution at the electrodes in aqueous media, including the use of hydrogen absorbing palladium electrodes [28], the addition of a barrier membrane located between the electrodes as a substrate for deposition [29], the addition of hydroquinone which reacts with the oxygen generated [30], the use of AC electric fields [31, 32, 33], and the application of pulsed electric fields (Pulsed-EPD) [27, 34, 35].

Reliable and tuneable methods of generating collagen biomaterials using EPD would be useful in a range of tissue engineering and other applications.

Accordingly, in a first aspect, the present invention provides a layer of collagen comprising an array of fibres of collagen, the layer having a thickness direction perpendicular to a plane extending within the layer, there being defined a range of in-plane directions perpendicular to the thickness direction and lying in the plane extending within the layer, wherein the fibres of collagen are substantially aligned within the layer along a first in-plane direction such that, when the ultimate tensile strength (UTS) of the layer is tested along said range of in-plane directions, the first in-plane direction corresponds to a maximum UTS and in a second in-plane direction, not parallel to the first in-plane direction, corresponds to a UTS that is at most 90% of the maximum UTS.

A second aspect of the invention provides a layer of collagen comprising an array of fibres of collagen, the layer having a thickness direction perpendicular to a plane extending within the layer, there being defined a range of in-plane directions perpendicular to the thickness direction and lying in the plane extending within the layer, wherein the fibres of collagen are substantially aligned within the layer along a first in-plane direction such that the birefringence of the layer is at least 0.01 when measured using polarised light microscopy.

A third aspect of the invention provides a laminated structure comprising at least two layers according to the first or second aspect.

A fourth aspect of the invention provides a method of manufacturing a layer comprising an array of fibres of collagen, the method comprising:
providing a suspension of insoluble collagen fibres;
providing a layer deposition interface;
applying an electric field across the suspension to cause electrophoretic deposition of the insoluble collagen fibres at the layer deposition interface, thereby building up a layer comprising deposited collagen, wherein the electric field is pulsed in order to subject the suspension to pulsed electrophoresis, the electric field strength being in the range 100-2000V/m, the average pulse length being in the range 10-100 ms and a duty cycle being 20-70%.

A fifth aspect of the invention provides a method of manufacturing a layer comprising an array of fibres of collagen, the method comprising:
providing a suspension of insoluble collagen fibres;
providing a layer deposition interface;
applying an electric field across the suspension to cause electrophoretic deposition of the insoluble collagen fibres at the layer deposition interface, thereby building up a layer comprising deposited collagen, wherein the layer deposition interface comprises a raft of bubbles generated in the suspension by the electric field.

A sixth aspect of the invention provides a method of manufacturing a layer comprising an array of fibres of collagen, the method comprising:
providing a suspension of insoluble collagen fibres;
providing a layer deposition interface;
applying an electric field across the suspension to cause electrophoretic deposition of the insoluble collagen fibres at the layer deposition interface, thereby building up a layer comprising deposited collagen,
wherein the insoluble collagen suspension is dialysed substantially to remove salts before the electrophoretic deposition A seventh aspect of the invention provides a method of manufacturing a layer comprising an array of fibres of collagen, the method comprising:
providing a suspension of insoluble collagen fibres;
providing a layer deposition interface;
applying an electric field across the suspension to cause electrophoretic deposition of the insoluble collagen fibres at the layer deposition interface, thereby building up a layer comprising deposited collagen,
wherein the layer deposition interface comprises a surface of a release layer.

An eighth aspect of the invention provides a method of manufacturing a layer comprising an array of fibres of collagen, the method comprising:
providing a suspension of insoluble collagen fibres;
providing a layer deposition interface;
applying an electric field across the suspension to cause electrophoretic deposition of the insoluble collagen fibres at the layer deposition interface, thereby building up a layer comprising deposited collagen,
wherein the layer deposition interface comprises at least a region having a non-planar profile, the layer being formed so as to conform with the shape of the layer deposition interface including said region having a non-planar profile.

A ninth aspect of the invention provides a method of manufacturing a layer comprising an array of fibres of collagen, the method comprising:
providing a suspension of insoluble collagen fibres;
providing a layer deposition interface;
applying an electric field across the suspension to cause electrophoretic deposition of the insoluble collagen fibres at the layer deposition interface, thereby building up a layer comprising deposited collagen,
wherein the layer deposition interface is provided by a membrane or scaffold having opposing major surfaces, the membrane or scaffold being supported by the suspension by at least one of the major surfaces of the membrane or scaffold being in contact with the suspension.

A tenth aspect of the invention provides a method of manufacturing a layer comprising an array of fibres of collagen, the method comprising:
providing a suspension of insoluble collagen fibres;
providing a layer deposition interface;
applying an electric field across the suspension to cause electrophoretic deposition of the insoluble collagen fibres at the layer deposition interface, thereby building up a layer comprising deposited collagen,
causing relative movement, in a relative movement direction, between the layer deposition interface and the suspension, thereby causing alignment of the collagen fibres in the layer, the fibres being substantially aligned within the layer along a first in-plane direction substantially parallel to the relative movement direction.

An eleventh aspect of the invention provides a method of manufacturing a layer comprising an array of fibres of collagen, the method comprising:
providing a suspension of insoluble collagen fibres;
providing a layer deposition interface;
applying an electric field across the suspension to cause electrophoretic deposition of the insoluble collagen fibres at the layer deposition interface, thereby building up a layer comprising deposited collagen,
wherein the suspension comprises viable mammalian cells, such that the cells are embedded in the layer after deposition.

A twelfth aspect of the invention provides a layered composite material comprising at least first and second fibrous layers each comprising an array of fibres of collagen, and a shape adapting layer, sandwiched between the first and second fibrous layers, the shape adapting layer being shear deformable substantially without damage to the first and second fibrous layers in order to conform the layered composite material to a required shape.

A thirteenth aspect of the invention provides a method of manufacturing a layered composite material comprising at least first and second fibrous layers each comprising an array of fibres of collagen, and a shape adapting layer, sandwiched between the first and second fibrous layers, the method comprising:
providing a suspension of insoluble collagen fibres;
providing a layer deposition interface;
applying an electric field across the suspension to cause electrophoretic deposition of the insoluble collagen fibres at the layer deposition interface, thereby building up a layer comprising deposited collagen to form the first fibrous layer;
depositing a shape adapting layer on the first fibrous layer;

providing the same or a further suspension of insoluble collagen fibres; and applying an electric field across the suspension to cause electrophoretic deposition of the insoluble collagen fibres at a surface of the shape adapting layer, thereby building up a layer comprising deposited collagen to form the second fibrous layer.

A fourteenth aspect of the invention provides a method of conforming a layered composite material to a required shape, comprising:

providing a layered composite material comprising at least first and second fibrous layers each comprising an array of fibres of collagen, and a shape adapting layer, sandwiched between the first and second fibrous layers, the layered composite material having a first shape; and deforming the first shape towards a second shape, different to the first shape, by shear deformation of the shape adapting layer without damage to the first and second fibrous layers, and setting the shape adapting layer.

A fifteenth aspect of the invention provides a method of manufacturing a layer comprising an array of fibres of collagen, the method comprising:

providing a suspension of insoluble collagen fibres;
providing a layer deposition interface;
applying an electric field across the suspension to cause electrophoretic deposition of the insoluble collagen fibres at the layer deposition interface, thereby building up a layer comprising deposited collagen, wherein the suspension comprises one or more therapeutic compounds, such that the one or more therapeutic compounds are comprised in the layer after deposition.

A sixteenth aspect of the invention provides a method of manufacturing a layer comprising an array of fibres of collagen, the method comprising:

providing a suspension of insoluble collagen fibres;
providing a layer deposition interface;
applying an electric field across the suspension by application of a deposition voltage to cause electrophoretic deposition of the insoluble collagen fibres at the layer deposition interface, thereby building up a layer comprising deposited collagen, wherein the electric field is varied with time to thereby vary the density of the layer comprising deposited collagen.

Preferred/optional features of these aspects are set out below. These are combinable singly or in any combination with any aspect of the invention, unless the context demands otherwise.

BRIEF DESCRIPTION OF THE FIGURES

FIG. 16 shows the manufacture of shaped and macro-textured collagen films by Pulsed-EPD: FIG. 16C shows schematic side and plan views of pulsed-EPD where one tubular electrode is placed within another, with collagen suspension between.

DETAILED DESCRIPTION

Figure 1:
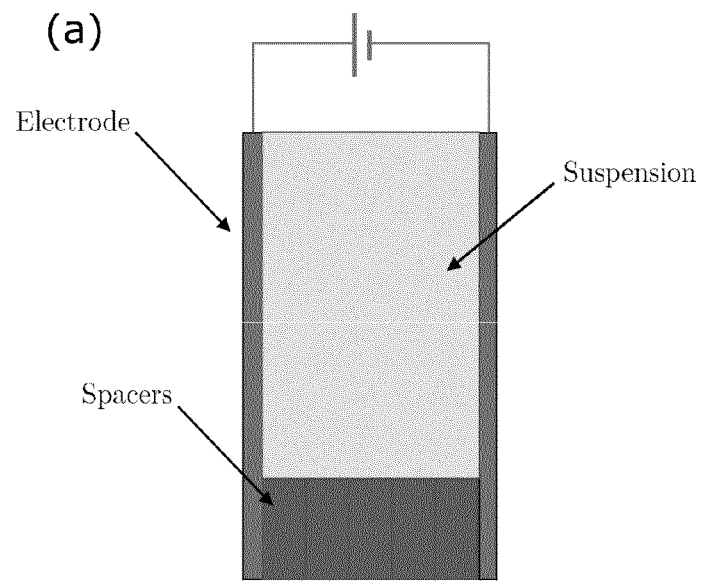
FIG. 1 shows a schematic of the systems used for pulsed-electrophoretic deposition, depicting (a) the EPD cell used, (b) a constant voltage pulse with period 10 ms and 40% duty cycle, as used in Pulsed-EPD.
Figure 1:
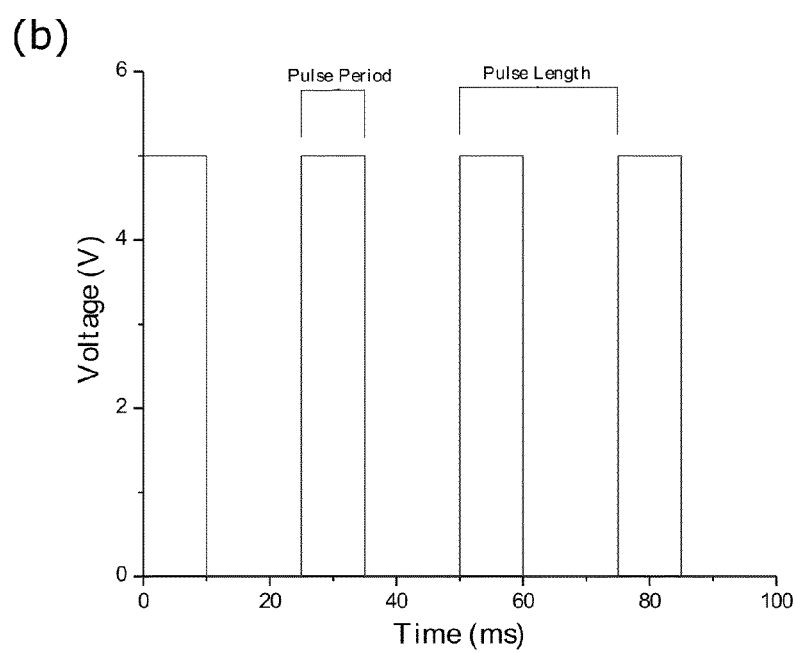

This invention relates to collagen biomaterials produced by the electrophoretic deposition of insoluble collagen suspensions at an interface, such as the surface of an electrode, to form a deposited collagen layer.

Insoluble or polymeric collagen forms the major fraction of most collagen tissue. It comprises aligned strands of collagen fibres which are covalently cross-linked and organised into large diameter fibrils with few small oligomeric aggregates. The large diameter fibrils contain covalent intrafibrillar cross-linkages. Insoluble collagen may obtained from commercial suppliers (e.g. Sigma Aldrich, UK, e.g. insoluble bovine achilles tendon collagen (C9879)) or may be purified from native collagen tissue by swelling the polymer at low pH into a clear solution/suspension, and then re-condensing/re-aggregating the collagen fibres by neutralisation (Steven F. S. (1967) Biochim. Biphys. Acta 140, 522-528; Schofield, J. D. et al (1971) Biochem. J. 124, 467-473; Steven, F. S. et al (1969) Gut 10, 484-487).

Insoluble collagen from any source may be used to generate biomaterials as described herein.

A suspension of insoluble collagen may be prepared, for example by rehydrating dried insoluble collagen. The dried insoluble collagen may be rehydrated in any non-toxic, water-miscible solvent, including ethanol, acetone, or glycerol. In some embodiments, the dried insoluble collagen is rehydrated in acid, preferably acetic acid, for example in 0.05M acetic acid at 4° C. for 48 hr, The rehydrated collagen may be homogenised, for example by treatment at 0° C. for 30 minutes using a homogeniser. In some embodiments, salts, ethanol and/or acetic acid may be introduced to the homogenised suspension of insoluble collagen.

The $\zeta$-potential of the homogenised suspension may affect the stability of the suspension and the rate of deposition. Preferably, the $\zeta$-potential of the homogenised suspension is 10 or higher, preferably 30 or higher.

In the present disclosure, electrophoresis of an insoluble collagen suspension permits the formation of a layer of deposited collagen at a layer deposition interface, such as an electrode surface.

A layer of deposited collagen produced as described herein may comprise an array of fibres of collagen. The layer may have a thickness direction perpendicular to a plane extending within the layer. A range of in-plane directions may be defined perpendicular to the thickness direction and lying in the plane extending within the layer.

In some embodiments, the array of fibres of collagen may be randomly orientated in-plane in the deposited layer.

In other embodiments, the array of fibres of collagen may be substantially aligned in a first in-plane direction in the deposited layer. The first in-plane direction may correspond to the direction of maximum ultimate tensile strength (UTS) of the layer. For example, the layer may have a UTS in a second in-plane direction that is not parallel to the first in-plane direction that is at most 90% of the maximum UTS. UTS may be measured using standard techniques. For example a collagen layer may be subjected to controlled tension until it fails and the maximum value on the stress-strain curve measured. A suitable method for determining UTS may comprise;

preparing a rectangular or dumbbell shaped sample of the membrane,
optionally, rehydrating the sample in a liquid medium,
measuring the initial thickness and width of the sample,
clamping the sample into appropriate grips of a mechanical testing machine, the separation between the grips being measured
applying a tensile force and recording the extension of the sample and the applied force,
increasing the tensile force until the sample breaks
converting the tensile force into a stress measurement using the recorded thickness and width (Stress=Force/Area)
converting the extension into a strain measurement (Strain=Extension/Original Length)
plotting the stress and strain onto a graph, with stress as the y axis and strain as the x axis wherein ultimate tensile stress is defined as the peak value on the stress-strain curve.

A layer of deposited collagen produced as described herein may be birefringent. The fibres of collagen may be substantially aligned within the layer along the first in-plane direction such that the birefringence of the layer is at least 0.015 when measured using polarised light microscopy. More preferably, the birefringence of the layer may be at least 0.02, at least 0.025 or at least 0.03 when measured using polarised light microscopy. A suitable protocol for measurement of birefringence of collagen membranes is set out below (see Example 18).

The second in-plane direction may be substantially perpendicular to the first in-plane direction.

A layer as described herein may have a thickness of at least 5 μm or at least 10 μm. A layer as described herein may have a thickness of up to 50 μm, or up to 100 μm or more. For example, a layer may be 10-50 μm thick.

The surface area of a layer is determined by the area of the layer deposition interface and may be adjusted in order to meet the requirements of the intended use of the layer. In some preferred embodiments, a layer as described herein may have an area, when viewed in plan view, of at least 20 cm$^2$, at least 30 cm$^2$, at least 50 cm$^2$, at least 100 cm$^2$, at least 500 cm$^2$, or at least 1000 cm$^2$.

In some embodiments, at least two layers of collagen as described herein may form a laminated structure (multilayer structure). The layers in the laminated structure may have respective first in-plane directions that are substantially parallel or more preferably substantially perpendicular to each other. In other words, the layers in the laminated structure may have respective first in-plane directions disposed at a predetermined angle to at least one other layer in the laminated structure, wherein the predetermined angle is an angle between 0 and 90°. Preferably the predetermined angle is between 10° and 90°, for example 10°, 20°, 30°, 40°, 50°, 60°, 70°, 80° or 90°, wherein the angle is measured as the smallest angle between two lines defined by the respective first in-plane directions of each layer in the laminated structure. Suitable laminated structures may be produced for example by multiple rounds of electrophoretic deposition as described below.

A layer of collagen as described herein may form a tubular structure. The layer in the tubular structure may be seamless. For example, tubular structures with a cross-sectional diameter of 500 μm or greater may be produced.

A layer of collagen or collagen membrane (single layer or multilayer) as described herein or as formed by a method described herein may be used to contain bodily fluids during surgery, or as a patch to stop blood loss, or as a venous or arterial replacement.

In some embodiments, a layer comprising an array of fibres of collagen may be produced by pulsed electrophoretic deposition. For example, a method may comprise applying a pulsed electric field across a suspension of insoluble collagen fibres to cause electrophoretic deposition of the insoluble collagen fibres at a layer deposition interface, thereby building up a layer comprising deposited collagen.

The electric field strength of the pulsed electric field may be in the range 10 to 5000 volts/m, preferably 100-2000 volts/m.

The average pulse length of the pulsed electric field may be in the range 10 to 100 ms, for example 15-50 ms.

The duty cycle of the pulsed electric field may be 20 to 70%, preferably 30 to 60%.

The pulsed electric field may be applied between opposing electrodes. At least one of the electrodes may be in contact with the suspension and a surface of the electrode may provide the layer deposition interface.

When the surface of an electrode provides the layer deposition interface, the potential difference between the electrodes for pulsed EPD may be at 1 to 20V, preferably 3 to 15V.

In other embodiments, a layer comprising an array of fibres of collagen may be produced by non-pulsed electrophoretic deposition. For example, a method may comprise applying a non-pulsed electric field, for example a DC electric field, across a suspension of insoluble collagen fibres to cause electrophoretic deposition of the insoluble collagen fibres at a layer deposition interface, thereby building up a layer comprising deposited collagen.

In some embodiments the electric field may be varied with time, for example by changing the applied voltage (also referred to herein as a deposition voltage) time to thereby vary the density of the layer comprising deposited collagen. For example, a method may comprise varying a deposition voltage with time to thereby vary the density of the layer comprising deposited collagen. By controlling the density of the deposited layer, it may be possible to produce membranes having different degradation properties, in particular for in-vivo use. Without wishing to be bound by theory, the inventors suggest that layers having higher density will degrade more slowly.

In some embodiments the deposition voltage may be increased over time to thereby increase the density of the deposited layer through the thickness of the deposited layer. In other embodiments the deposition voltage may be decreased over time to thereby decrease the density of the deposited layer through the thickness of the deposited layer. By controlling the how the density of the layer varies in a thickness direction, it may be possible to provide a layer having a variable rate of degradation over time.

In some embodiments, multiple collagen layers may be deposited, wherein electric field may be different during electrophoretic deposition of subsequent layers. In this way it may be possible to produce a multilayer collagen structure wherein the density of some or all of the layers in the multilayer structure is different.

The layer deposition interface may comprise a raft of bubbles generated in the suspension by the electric field. The raft of bubbles may be generated at a surface of an electrode in contact with the suspension, the layer deposition interface thereby being spatially separated from the surface of the electrode. In this case, the bubbles are generated due to electrolysis of a carrier liquid comprised in the suspension (e.g. water).

The electric field may be applied between opposing electrodes with the potential difference between the electrodes being, for example at least 20 V. The potential difference between the electrodes may be, for example at most 200 V.

In preferred embodiments, the insoluble collagen suspension may be dialysed before the electrophoretic deposition. For example, a method of manufacturing a layer comprising an array of fibres of collagen may comprise: providing a suspension of insoluble collagen fibres dialysed substantially to remove salts before the electrophoretic deposition; and applying an electric field across the suspension to cause electrophoretic deposition of the insoluble collagen fibres at a layer deposition interface, thereby building up a layer comprising deposited collagen.

In some embodiments, a method may comprise the step of dialysing the insoluble collagen suspension. One or more dialysis steps may be employed, to progressively reduce the salt content of the suspension to the desired level. Dialysis may be useful for example in ensuring the consistency of deposition between different sources of insoluble collagen.

Suitable methods of dialysis, for example using dialysis membrane, are well known in the art. For example, the suspension may be enclosed in a cellulose dialysis membrane and dialysed in deionised water for 24 hours.

In some embodiments, the collagen layer may be deposited on the surface of a release layer. For example a method of manufacturing a layer comprising an array of fibres of collagen may comprise applying an electric field across a suspension of insoluble collagen fibres to cause electrophoretic deposition of the insoluble collagen fibres at a layer deposition interface, thereby building up a layer comprising deposited collagen, wherein the layer deposition interface comprises a surface of a release layer.

The release layer may be at a surface of an electrode to permit separation of the deposited layer from the electrode. The release layer may be a sacrificial layer that is selectively removed in order to permit separation of the deposited layer from the electrode.

The sacrificial layer may be a coating comprising a sacrificial polymer. Suitable sacrificial polymers may be non-toxic and are preferably soluble in first solvent, for example an organic solvent, such as acetone, and insoluble in an acidic aqueous solution.

Suitable sacrificial polymers include cellulose acetate. Following deposition of the collagen layer, the sacrificial polymer within the coating may be dissolved using the first solvent to release the deposited layer from the electrode. The use of a cellulose acetate sacrificial layer to release a film deposited by EPD is known in the art (S. A. Hasan, et al ACS Nano, 4, 12, pp. 7367-7372, 2010). A collagen layer produced as described herein may be analysed or characterised by any suitable analytical method. Suitable methods include fourier-transform infrared spectroscopy (FTIR), For example, a collagen layer may be analysed by generating a FTIR spectrum showing the absorption of the collagen layer at each wavelength across a range of IR light. Absorption at a wavelength is determined by the specific molecular bonds and transitions present in the layer and an FTIR spectrum may be characteristic of the composition of a collagen layer. Differences in the composition of two collagen layers may be indicated by the presence or absence of additional peaks in their FTIR spectra.

The methods described herein may be useful in producing shaped collagen layers that have a non-planar profile. For example, a method of manufacturing a layer comprising an array of fibres of collagen may comprise applying an electric field across a suspension of insoluble collagen to cause electrophoretic deposition of the insoluble collagen fibres at a layer deposition interface that comprises at least a region having a non-planar profile, the layer being formed so as to conform with the shape of the layer deposition interface including said region having a non-planar profile.

The region having the non-planar profile may occupy at least 50% of the layer deposition interface.

The region having a non-planar profile may comprise one or more protrusions or depression. For example, the layer formed on the region of the interface may comprise one or more grooves and/or ridges.

The region having a non-planar profile may comprise a partially or continuously curving profile. For example, the layer formed on the region of the interface may comprise a seamless tube.

In some embodiments, the layer deposition interface is provided by a membrane or scaffold. In some embodiments the membrane or scaffold is formed from collage. For example, the layer deposition interface may be provided by a collagen membrane or collagen scaffold. In other embodiments the membrane or scaffold is formed from a non-collagenous material. For example, the membrane or scaffold may be formed from nitrile or silicone rubber. In some embodiments the membrane or scaffold may contain perforations or pores (the membrane or scaffold may be porous.

In some embodiments, the membrane or scaffold has at one major surface in contact with the suspension, and the opposing major surface of the membrane or scaffold is in contact with a second liquid, e.g. a liquid selected from water, ethanol, acetone, or any combination of these liquids. In other embodiments, the membrane or scaffold is held within the suspension and both of the major surfaces of the membrane or scaffold may be in contact with the suspension.

For example, a method of manufacturing a layer comprising an array of fibres of collagen may comprise applying an electric field across a suspension of insoluble collagen fibres to cause electrophoretic deposition of the insoluble collagen fibres at a layer deposition interface provided by a collagen membrane having opposing major surfaces, the collagen membrane being held within the suspension and with both major surfaces in contact with the suspension.

The layer deposition interface may be provided by the surface of one of the electrodes, optionally with a sacrificial layer formed over the surface of the electrode as described herein. The electrode surface may provide the non-planar profile as described above.

Alternatively, where the layer deposition interface is not provided by the electrode surface or a sacrificial layer formed on the electrode surface, the shape of the electrode may still influence the shape of the deposited layer. For example, the electrode may be provided with electric field concentration features. Suitable electric field concentration features comprise sharp protrusions at which the electric field is concentrated by virtue of the local shape of the electrode. At positions of the layer deposition interface corresponding to (e.g. overlying) the electric field concentration features, there may be a more rapid build-up of deposited collagen, leading to a corresponding local increase in thickness of the deposited layer and hence a variation in shape of the deposited layer.

The collagen membrane that provides the layer deposition interface may be produced by a method described herein.

In some embodiments, the collagen fibres may be aligned in the deposited layer by relative flow between the layer deposition interface and the suspension. For example, a method of manufacturing a layer comprising an array of fibres of collagen may comprise applying an electric field across a suspension of insoluble collagen fibres to cause electrophoretic deposition of the insoluble collagen fibres at a layer deposition interface, and causing relative movement, in a relative movement direction, between the layer deposition interface and the suspension, thereby causing alignment of the collagen fibres in the layer. The fibres may be substantially aligned within the layer along a first in-plane direction substantially parallel to the relative movement direction.

Relative movement or flow between the layer deposition interface and the suspension may be generated by any convenient method. For example, the suspension may be moved across the layer deposition interface using a pump or the layer deposition interface may be moved through the suspension, for example by rotating or spinning an electrode.

Relative flow between the layer deposition interface and the suspension is preferably in in a range of 1 to 15 cm/min, preferably 3 to 10 cm/min. Providing a relative flow speed in this range may provide for optimal deposition of collagen.

After deposition of a first layer, the relative movement direction may be changed, in order to deposit a subsequent layer in which the fibres are substantially aligned within the layer along a second in-plane direction, not parallel with the first in-plane direction. The second in-plane direction may be arranged at an angle of between 1° and 90° to the first in-plane direction, for example 10°, 20°, 30°, 40°, 50°, 60°, 70°, 80° or 90° to the first in-plane direction, wherein the angle is measured as the smallest angle between two lines defined by the first and second in-plane directions respectively.

In some embodiments one or more therapeutic compounds (drugs) may be incorporated into the deposited collagen layer. For example, a method of manufacturing a layer comprising an array of fibres of collagen may comprise applying an electric field across a suspension comprising insoluble collagen fibres and one or more therapeutic compounds to cause electrophoretic deposition of the insoluble collagen fibres and the one or more therapeutic compounds at the layer deposition interface, thereby building up a layer comprising deposited collagen with the one or more therapeutic compounds comprised therein. A wide range of therapeutic compounds may be suitable for electrophoretic deposition in this manner, including, for example, tetracycline, dexamethasone, gentamicin, tobramycin, minocycline, teicoplanin, sulbactam-cefoperazone, cefotaxime, fusidic acid, or clindamycin, or any other suitable therapeutic compound.

In some embodiments, multiple collagen layers may be deposited, wherein the concentration of the one or more therapeutic compounds may be changed between electrophoretic deposition of subsequent layers, for example by changing the concentration of the one or more therapeutic compounds in the suspension before application of the electric field to deposit each subsequent layer. In this way, it may be possible to form a multilayer collagen membrane having one or more therapeutic compounds comprised therein, wherein the concentration of the one or more therapeutic compounds is different in some or all of the layers of the multilayer membrane. In this may it is possible to provide a collagen membrane with a varying drug release profile.

In some embodiments, multiple collagen layers may be deposited, wherein the concentration of the one or more therapeutic compounds remains the same or is varied between electrophoretic deposition of subsequent layers, wherein the electric field is different during deposition of some or all of the layers in the resultant multilayer structure.

In this was, it may be possible to provide a multilayer collagen membrane having one or more therapeutic compounds comprised therein, wherein the density of some or all of the layers of the multilayer membrane is different. In this may it is possible to provide a collagen membrane with a varying drug release profile, due to different degradation properties of layers having different densities.

In some embodiments, mammalian cells may be incorporated into the deposited collagen layer. For example, a method of manufacturing a layer comprising an array of fibres of collagen may comprise applying an electric field across a suspension comprising insoluble collagen fibres and viable mammalian cells to cause electrophoretic deposition of the insoluble collagen fibres and cells at the layer deposition interface, thereby building up a layer comprising deposited collagen with viable mammalian cells are embedded therein.

Mammalian cells may include muscle cells to provide contractile structures, vascular and/or neural cells to provide conductive elements, metabolically active secretory cells, such as liver cells, hormone synthesising cells, sebaceous cells, pancreatic islet cells or adrenal cortex cells to provide secretory structures, fibroblasts, such as dermal fibroblasts, skin keratinocytes, melanocytes (and combination keratinocytes of the two), neurons and glial cells, such as Schwann cells, for nerve implants, smooth muscle cells and endothelial cells for vessel structures, urothelial and smooth muscle cells for bladder/urethra structures, osteocytes, chondrocytes, and tendon cells for bone and tendon structures and stem cells, such as corneal (limbal) stem cells, skin epidermal stem cells, gut (intestinal) stem cells, orogenital stem cells, bronchial and other epithelial stem cells, bone marrow stem cells, growth plate stem cells. Preferred cells may include dermal fibroblasts, keratinocytes, melanocytes, stem cells and chondrocytes.

Cells may be distributed interstitially within a collagen biomaterial or composite material in any arrangement. For example, the cells may be distributed homogeneously throughout the collagen biomaterial or composite material or may be distributed in one or more layers of the biomaterial.

Mammalian cells may be incorporated into the collagen suspension under suitable conditions of temperature, neutral pH, ionic strength, osmolarity and sheer to maintain viability. Preferably, the collagen suspension is neutralised before the cells are added and/or one or more additional components added to provide suitable conditions to maintain cell viability. For example, carbon sources and salts, such as sucrose, glucose, Mg2+, and sodium chloride may be added to the suspension. Glycosaminoglycans (GAGs) may be added to the suspension. For example, hyaluronic acid or chondroitin sulphate, in concentrations of e.g. 3-0.03 g/L may be added to the suspension. Adding GAGs to the suspension may provide for improved electrophoretic deposition of collagen fibres and/or cells by increasing the charge of the aggregates. The osmolarity of the suspension may be adjusted to 250-350 Osm/L, preferably around 300 mOsm/L. The cells may be added to the collagen suspension, for example by pipette seeding followed by gentle mixing. The conductivity of the suspension may be about 3.2 mS/cm.

The initial cell density in the collagen suspension may be from about $1\times10^4$ to $1\times10^7$ cells per ml, more preferably from about $1\times10^5$ to $5\times10^6$ cells per ml, for example $1.5\times10^5$ to $3.5\times10^6$.

To reduce and/or prevent cell death or damage, a collagen layer or biomaterial comprising mammalian cells may be stored under conditions which maintain viability but which do not support cell growth, until ready for use. A layer or biomaterial may for example be stored frozen, or at low temperature, room temperature or 37° C. The layer or biomaterial may be stored at low temperature e.g. 0 to 10° C. or frozen (<0° C.) in the presence of a cryoprotectant. The layer or biomaterial can be stored in cell culture medium for short periods of time, for example up to 1 week.

In some embodiments, the layer or biomaterial may be subjected to drying or desiccation, for example heat, airflow or vacuum drying. In other embodiments, the layer or biomaterial may be partially dehydrated, for example by removal of up to 40% up to 50% up to 60% up to 70% or up to 80% (w/w) of the liquid from the collagen layer or biomaterial. This partial dehydration may be the result of drying or desiccation as previously mentioned. Preferably, where the layer or biomaterial comprises mammalian cells, the layer or biomaterial may be at most partially dehydrated. Full dehydration may kill mammalian cells comprised in the layer or biomaterial.

In some embodiments, the layer or biomaterial may be subjected to desiccation by lyophilisation (also known as cryodesiccation or freeze-drying). Where the layer or biomaterial is subjected to lyophilisation, a porous collagen membrane or scaffold can be formed. By altering the freeze drying parameters and thickness of the collagen layer or biomaterial before lyophilisation, the porosity in the final porous collagen membrane/scaffold can be altered.

In some embodiments, a collagen membrane produced by a method disclosed herein (e.g. produced by drying or desiccation of a collagen layer produced by a method disclosed herein) may be used to produce a porous collagen scaffold incorporating the collagen membrane. In such methods, the collagen membrane may be placed in a mould together with a collagen suspension. The mould containing the collagen membrane and collagen suspension may then be lyophilised (freeze-dried) to form a porous collagen scaffold with an attached collagen membrane.

The methods described herein may be useful in producing layered composite materials that can be deformed and shaped. A layered composite material may for example comprise at least first and second fibrous layers that each comprising an array of fibres of collagen. The material may further comprise a shape adapting layer that is sandwiched between the first and second fibrous layers. The shape adapting layer may be shear deformable substantially without damage to the first and second fibrous layers, allowing the layered composite material to conform to a required shape.

A suitable layered composite material may be manufactured by a method comprising;
  applying an electric field across a suspension of insoluble collagen fibres to cause electrophoretic deposition of the insoluble collagen fibres at the layer deposition interface, thereby building up a layer comprising deposited collagen to form the first fibrous layer;
  depositing a shape adapting layer on the first fibrous layer;
  providing the same or a further suspension of insoluble collagen fibres; and
  applying an electric field across the suspension to cause electrophoretic deposition of the insoluble collagen fibres at a surface of the shape adapting layer, thereby building up a layer comprising deposited collagen to form the second fibrous layer.

A layered composite material having a first shape may be conformed to a required shape by deforming the first shape towards a second shape, different to the first shape, by shear deformation of the shape adapting layer without damage to the first and second fibrous layers, and setting the shape adapting layer.

At least in the first fibrous layer, the fibres of collagen may be substantially aligned within the layer along a first in-plane direction.

In the second fibrous layer, the fibres of collagen may be substantially aligned within the layer along a second in-plane direction, the second in-plane direction being non-parallel with the first in-plane direction. The second in-plane direction may be arranged at an angle of between 1° and 90° to the first in-plane direction, for example 10°, 20°, 30°, 40°, 50°, 60°, 70°, 80° or 90° to the first in-plane direction, wherein the angle is measured as the smallest angle between two lines defined by the first and second in-plane directions respectively The shape adapting layer comprises a shear thinning material, such as hyaluronic acid, lubricin, xantham gum, carrageenan, GAG hydrogels and HyA derivatives, such as methacrylated HyA.

The shape adapting layer may further comprise a cross linking agent, activatable to cross link the shape adapting layer. Suitable cross-linking agents may include Riboflavin, Irgacure, and Rose Bengal.

The shape adapting layer may be deposited onto the first fibrous layer by electrophoretic deposition as described herein. The presence of one or more shape adapting layers in a composite material allows the material to be moulded after production. This may be useful in adjusting the shape of the composite material to correspond to the shape of a defect in a patient in the clinic.

In some preferred embodiments, the layered composite material may comprise at least 4 fibrous layer and at least 3 shape adapting layers separating the respective fibrous layers.

Collagen layers, biomaterials and composite materials described herein may be useful for research or for use in therapy, pharmaceutical development, cell culture, orthopaedics, dermatology, dentistry, for example in dental ridge augmentation, and wound healing, for example to promote skin regeneration.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and any sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

EXPERIMENTAL

1. Materials and Methods

Preparation of Collagen Suspension

Collagen was rehydrated from insoluble bovine achilles tendon collagen (C9879 Sigma Aldrich, UK) by soaking in 0.05M acetic acid at 4° C. for 48 hr. It was then homogenised on ice for 30 minutes at 10,000 rpm using an Ultra-Turrax VD125 homogeniser (VWR International Ltd, UK) until a milky appearance was achieved and no large particles were apparent. Ethanol was then added under further homogenisation. The ζ-potential of the suspension was determined using laser Doppler electrophoresis with a Zetasizer Nano-ZS (Malvern Instruments).

Preparation of Hyaluronic Acid Solutions

Hyaluronic acid (hyaluronic acid, sodium salt, from *Streptococcus equi*, 91%, Alfa Aesar, UK) was dissolved in DI water under ice and homogenised at 10,000 rpm using an Ultra-Turrax VD125 homogeniser (VWR International Ltd, UK) for 5 minutes until a clear mixture was achieved with no visible hyaluronic acid present. The solution was refrigerated overnight, and kept on ice while ethanol was added dropwise to 70% vol under homogenisation at 12,000 rpm.

Electrophoretic Deposition by DC- and Pulsed-EPD

EPD was carried out at constant voltage using a custom built cell as seen schematically in FIG. 1a, consisting of two 316L steel electrodes separated by silicone rubber spacers, with deposition area 2.5 cm×3.5 cm. The two electrodes were connected to an EP-603 DC power supply (Manson Engineering Industrial Ltd) for DC-EPD, or to a TGA1241 Arbitrary Waveform Generator (TTI) for Pulsed-EPD.

Pulsed voltage EPD uses a pulse of constant voltage, in which the pulse length, duty cycle, and voltage can be independently varied, shown in FIG. 1b. The duty cycle is defined as DC=PulsePeriod/PulseLength, and the sum total of the time that the voltage is above 0 is called the $T_{on}$, i.e. DC=$T_{on}/(T_{on}+T_{off})$. Unless otherwise noted, depositions were carried out for a total $T_{on}$ of 1.5 hours. Deposited films were evaluated either as is, or were dried overnight in a fume hood, and dry masses of films were measured using a Sartorius CP124S balance (0.0001 g±0.0001).

To carry out multilayer electrophoretic depositions, collagen or hyaluronic acid was injected into the cell before the generator was activated for the required $T_{on}$. After deposition, the electrodes were removed and air dried in a fume hood. Subsequent layers were produced by re-attaching the electrodes to the EPD cell, injecting the desired suspension, and applying a pulsed electric field. This can be seen schematically in FIG. 2.

Preparation of Solvent Cast Collagen Membranes for Comparison

Cast films were prepared by syringing 5 ml of collagen suspension into a silicone mould (Lakeland Ltd.), before drying overnight in a fume hood. Samples were released by inversion of the moulds.

Atomic Force Microscopy

AFM was carried out by placing samples on a silicon substrate before imaging with a Dimension 3100 (Bruker Ltd) in light tapping mode using RTESP Silicon AFM tips (Veeco: resonant frequency 200400 Hz, spring constant 2040 N m−1) at room temperature. Scans were performed at random locations at a scan rate of 0.5 HZ and 512 samples per line. Image analysis was performed with Gwyddion software [36].

SEM & cryoSEM

Samples for SEM were mounted on stubs before being sputter coated using a gold target at 25 mA for 4 minutes. Samples were imaged on a JEOL JSM-5800LV SEM (JEOL UK Ltd) at 15 kV accelerating voltage in secondary electron imaging mode.

Samples for cryoSEM were frozen with slushy nitrogen at −195° C. and shattered under vacuum, before being sputter coated with a platinum target in situ. Samples were then transferred to a Zeiss EVO HD15 (Carl Zeiss Ltd) where they were imaged at 25 kV accelerating voltage in backscattered electron imaging (BSD) mode.

μ-CT 3D visualisation by micro-computed tomography (μ-CT) was performed using a Skyscan 1272 system (Bruker microCT). Images were with a 4 k camera at an operating voltage of 25 kV, a pixel size of 1.25 μm, step size of 0.2°, a frame average of 2, and a rotation of 180°. Projections were processed into 3D datasets using a full cone beam feldkamp reconstruction algorithm in NRecon, before visualisation in CTVox (Bruker Ltd.).

Dialysis of Collagen Suspensions

Collagen suspensions were generated as described above before being enclosed in cellulose dialysis membranes and dialysed in deionised water for 24 hours, changing the water after the first 2 and 4 hours. Dialysis water is normally changed more times than this, such as up to 4-5 times over a 48 hour period.

For comparative assays, collagen solutions were generated from collagen I stocks obtained from 4 different suppliers and dialysed as described above. Sigma bovine achilles tendon collagen 1—C9879 CS-Dermal—01AWB004 (CS010), Devro—01AWB003 (FS28005), CD-Tendon—CS301

2. Results

Example 1: Effect of Pulse Parameters on Collagen Deposition

In order to investigate the effect of pulse parameters on surface morphology, a series of collagen films were prepared by pulsed EPC with a range of pulse width, duty cycles, and voltages, with a total $T_{on}$ of 5 minutes for a 0.01 wt % collagen slurry.

Effect of pulse width: the number of bubbles formed in the deposit (considered to be due to the evolution of hydrogen gas at the electrode) initially decreased with a reduction in the pulse time from 50 ms to 1 ms, before increasing again when the pulse time was reduced below 1 ms. The low pulse widths employed indicate that the deposition of collagen by Pulsed-EPD is highly sensitive to the evolution of gas at the electrodes. Pulsed-EPD has been theorised to reduce the formation of bubbles in deposits by leading to a change in the gas generation site with each separate pulse. Without wishing to be bound by theory, we can explain the increase in bubble formation below 1 ms by theorising that when the pulse length becomes short enough there is not sufficient time for gas molecules to diffuse away from the gas generating site before the site becomes active again during a later pulse.

Effect of duty cycle on deposit formation: there is a reduction in the number of bubbles produced in the deposit as the duty cycle decreases from 50% to 20%, but when the duty cycle reached 20% the formation of the film was disrupted, with no coherent deposit being obtained.

Effect of voltage on deposit formation: a clear change can be seen in both the quantity of bubbles produced and in the quality of the deposit. At 5V there is a large number of bubbles present in the deposit, at 4V there are no bubbles present and there is a coherent deposit, and at 3V no deposit was formed.

Example 2: Effect of Organic Liquid Additions on Collagen Deposition

To investigate the effect of addition of an organic liquid to the collagen suspension, ethanol was chosen as it is completely miscible with water and is non-toxic.

Figure 4:
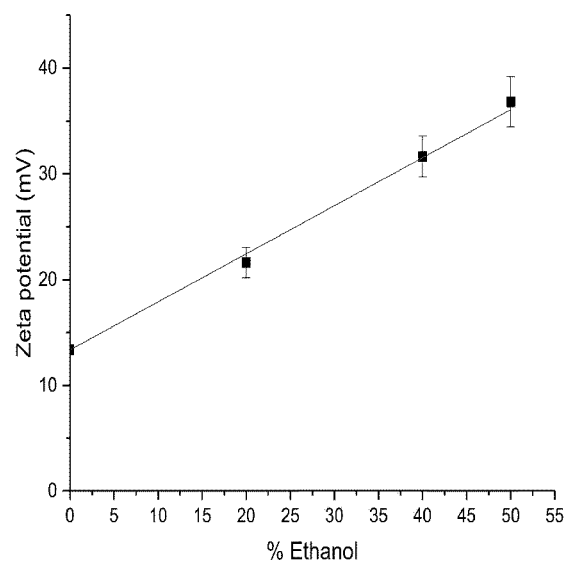
FIG. 4 shows the effects on membrane deposition of the addition of ethanol to the collagen suspension. The graph depicts: ζ-potential of collagen as a function of suspension ethanol percentage.

FIG. 4 shows the ζ-potential of collagen with respect to the proportion of ethanol in the mixed acetic acid:ethanol suspension. The ζ-potential rose linearly with increasing ethanol proportion up to 50% ethanol. Above this, ethanol proportion ζ-potential readings could not be determined.

Collagen films were then deposited by Pulsed-EPD with varying proportions of ethanol to explore the effect of ethanol on the deposited films, (V=5V, pulse length=25 ms, DC=40%, spacing=7.65 mm). At 25% ethanol, the deposited films show the effects of bubble formation, with a large amount of visible damage to the surface of the film in the form of large holes and a white cloudy structure, at 50% ethanol the deposited film is free from damage caused by evolved gas, giving a defect free deposit, and at 75% a defect free film was formed but the film was much less dense and was less robust. As the volume fraction of the organic medium increases, the water fraction reduces correspondingly, reducing the amount of water in contact with the electrode that can be electrolysed, reducing the amount of gas evolved.

Example 3: Effect of Pulse Width on Collagen Deposition

To determine if altering the pulse width affected the mass of collagen deposited on the electrode for a given $T_{on}$, the deposited mass was measured for a range of pulse widths while the $T_{on}$ was fixed.

Figure 5:
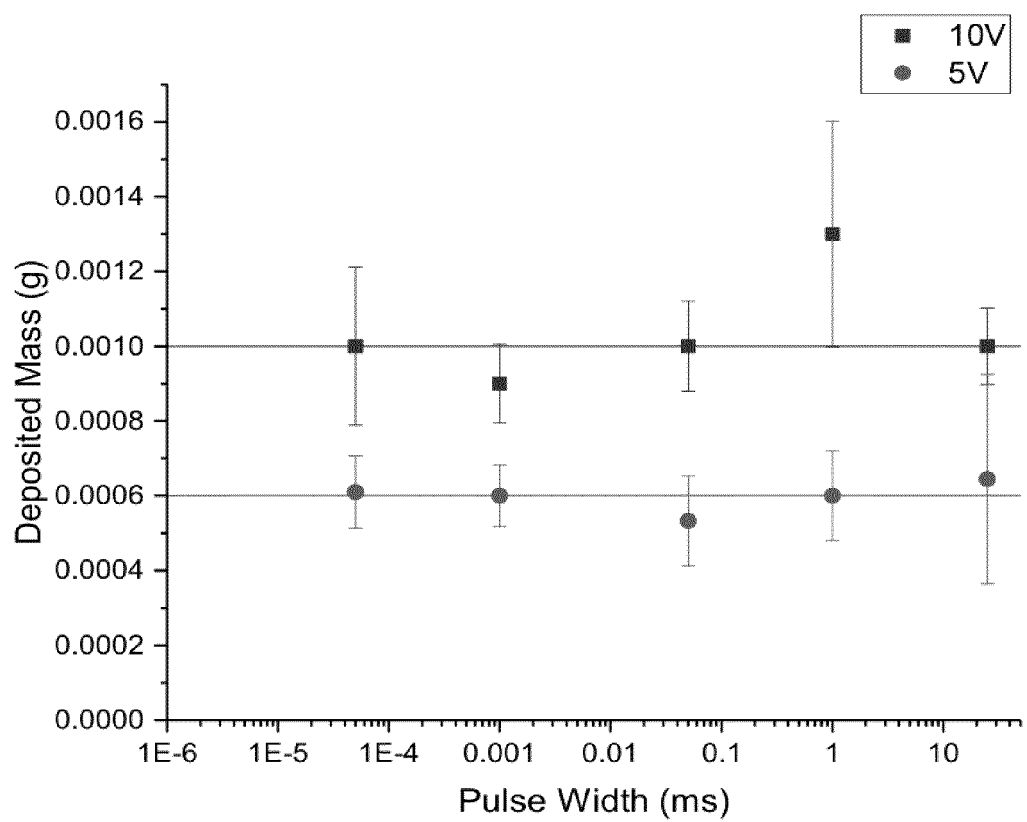
FIG. 5 shows the mass of collagen deposited by Pulsed-EPD for different pulse widths, with a total $T_{on}$ of 5 minutes. (DC=50%, electrode separation=7.65 mm).

A 0.1 wt % suspension of collagen was deposited for $T_{on}$ of 5 minutes. Pulsed-EPD at 10V lead to a mass of approximately 0.001 g being deposited, with this decreasing to 0.0006 g when the potential was set to 5V (FIG. 5). The smaller deposited mass at a lower applied potential is expected as a lower applied potential will reduce the velocity of the suspended particles and hence the rate of deposit formation. Additionally, at both applied potentials, altering the pulse width had no effect on the mass of collagen deposited. This implies that there is little difference in the mass transfer rate when the pulse width is altered.

Example 4: Deposition of Multiple Collagen Layers

In EPD of ceramic systems, it has generally been accepted that as material is deposited at the electrode the EPD cell resistance increases [37], reducing the rate of deposition, and decreasing the mass that can be deposited in each subsequent deposition step. It has been suggested that this decrease in the rate of mass deposition is controlled by a complex mechanism involving the electrostatic interactions between ions and the charged deposit, and the retention of the charge carrying species in the deposit, which is dependent on a range of variables such as the pore size and Debye screening length of the depositing particles [27].

Figure 6:
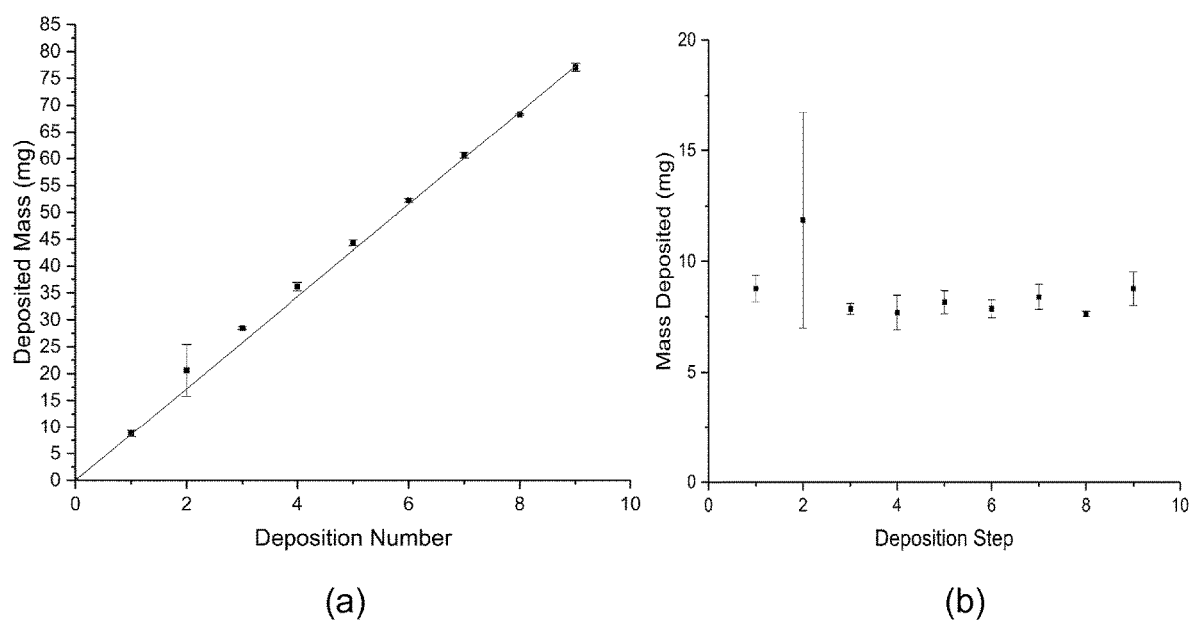
FIG. 6 shows the mass of collagen deposited by sequential depositions at pulse length=25 ms, DC=40%, Electrode spacing=7.65 mm, V=5V: (a) total deposited mass of collagen with number of sequential depositions; (b) mass deposited per deposition step for sequential depositions.

To determine the effect of deposited collagen on the deposition of further layers, collagen was deposited sequentially onto an electrode, with the electrode being dried and massed between each deposition step. The results from this, seen in FIG. 6, show that the mass of collagen deposited was surprisingly unaffected by previous deposition steps. Additionally, we found that when the collagen suspension was replaced after each deposition, without drying, the mass that could be deposited in each step did not change (data not shown).

Figure 7:
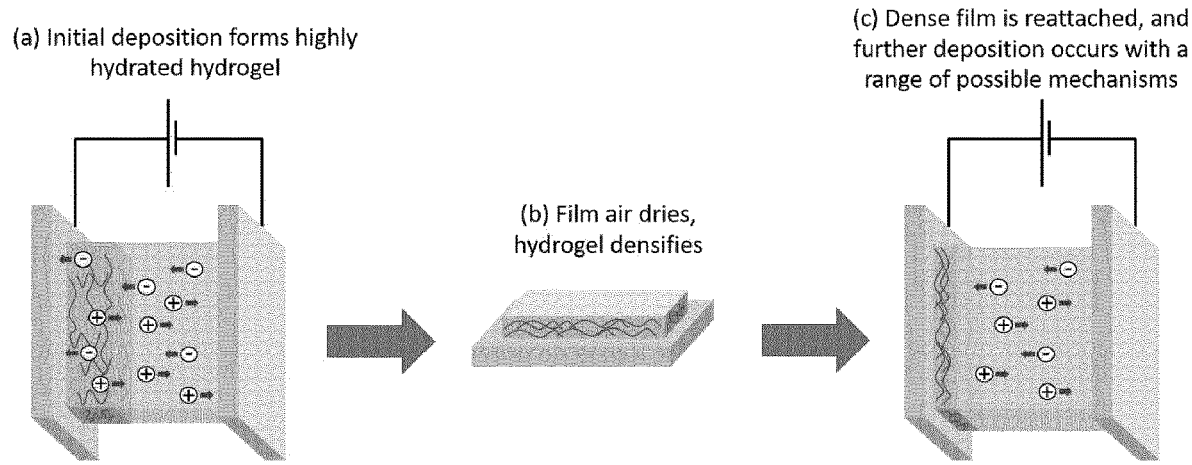
FIG. 7 shows a schematic of multiple depositions of collagen by Pulsed-EPD: (a) film is initially deposited as a highly hydrated hydrogel, with sufficient space between collagen fibres for ion transport to continue; (b) As the hydrogel dries, it forms a dense, non-porous, film; (c) the electrode and film are reattached to the EPD cell and new collagen suspension is added. The film charges, allowing for deposition to continue without an increase in the resistance.

When a collagen deposit is initially produced during EPD it forms a highly hydrated gel. Without being bound by theory, it appears this initially deposited gel has sufficient porosity to allow transport of conductive species through, as there is a conductive pathway that results in a minimal increase in the EPD cell's resistance. During drying the deposited gel collapses, producing a much denser film approximately 100 times thinner that cannot be rehydrated to the original deposit thickness. We have found that the deposition behaviour, and hence electrical conductivity, is unaffected. It is possible that the densified collagen membrane is still permeable enough to allow for ion transport unimpeded; or that the hydrated collagen membrane, when an electric field is applied, undergoes structural changes that affect the double layer repulsions between the collagen fibres, changing the porosity of the membrane and producing a pathway for conductive ions; or the collagen membrane could become rapidly charged upon application of an electrical potential. This is shown schematically in FIG. 7.

Example 5: Collagen Deposit Microstructure

Collagen films were produced by Pulsed-EPD and by solvent casting. Dry films were examined by AFM, and SEM, and hydrated films were examined with cryoSEM.

In order to remove the collagen membranes from the electrode after deposition, mechanical cleavage was applied by running a razor blade between the electrode and the membrane. No damage caused by separation was visible and the film maintained mechanical stability, integrity, and flexibility once removed from the substrate.

Figure 8:
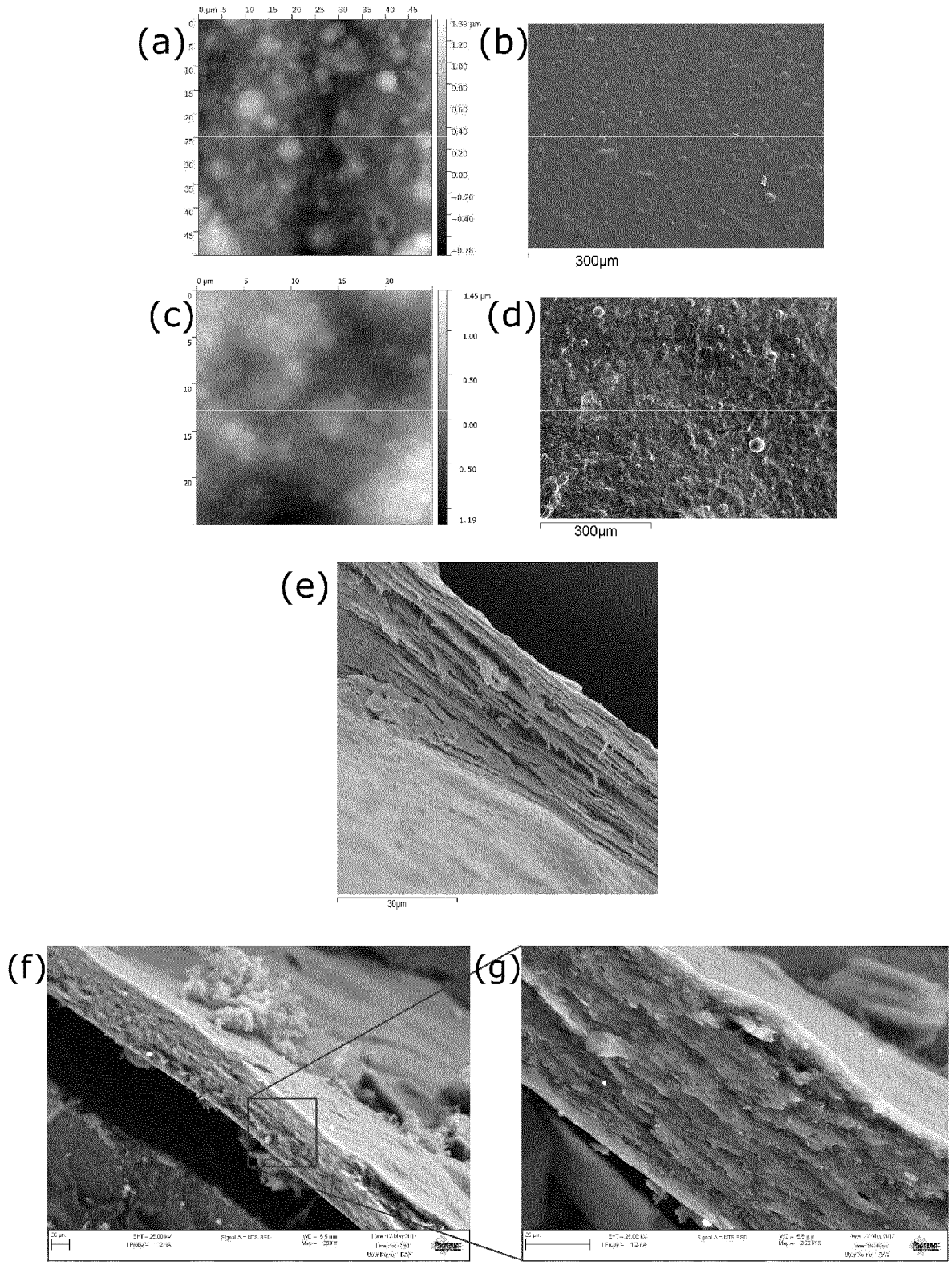
FIG. 8 shows the microstructure of collagen films: (a,b) AFM and SEM-SEI micrographs of the surface of a collagen film deposited by Pulsed-EPD, (c,d) AFM and SEM-SEI micrographs of the surface of a cast collagen film. (e) SEM micrograph of a cross section of a cast collagen film, and (f,g) BSD cryoSEM micrographs of the edge of a freeze-shattered collagen film produced by Pulsed-EPD.

FIG. 8a shows an AFM height map of a Pulsed-EPD collagen film. Visible on the surface are a number of circular and ring like structures. Many of these larger circular structures are likely caused by the evolution of microbubbles during the deposition process, with the ring structures the remnants of collapsed bubbles. This agrees with the mechanism of changing gas evolution sites during Pulsed-EPD as micro-bubbles have been able to nucleate but none of these visible micro-bubbles were able to coalesce into larger macro-bubbles. SEM investigation of the surface of the collagen film, seen in FIG. 8b shows a similar structure, with the overall surface of the film being planar with small circular lumps caused by micro-bubbles or due to collagen globules. FIGS. 8c and 8d show the surface of a collagen film formed by solvent casting, in which a broadly similar morphology can be seen, though the characteristic ring structures produced by collapsing bubbles are absent as expected. The surface similarity between the cast and Pulsed-EPD films is confirmed by FIG. 8d which shows a textured surface morphology with a number of collagen globules present.

The existence of the interior micron and sub-micron pores can be seen by cross sectional cryoSEM, shown in FIG. 8g. This porosity is likely to be due to bubbles that have nucleated on the surface of the membrane during deposition, which have then been overlaid with further collagen fibres, leaving a void internally within the membrane. This indicates that there is limited movement of the collagen fibres once they have come into contact with the deposit as the pores have remained unclosed during the drying process. The pores formed through this mechanism are too small however to have more than a local effect on the microstructure of the membrane. FIGS. 8f and 8g also show no signs of damage at the edges of the membrane due to the mechanical separation from the electrode.

CryoSEM was also used to examine the general microstructure of the membranes, with FIGS. 8f and 8g showing the interior microstructure of a swollen membrane. The membrane is clearly of an even thickness across its length, and in FIG. 8g the membrane can be seen to be comprised of many individual collagen fibres in a dense lamellar structure.

Example 6: HyA Deposition by DC-EPD and Pulsed-EPD

Figure 9:
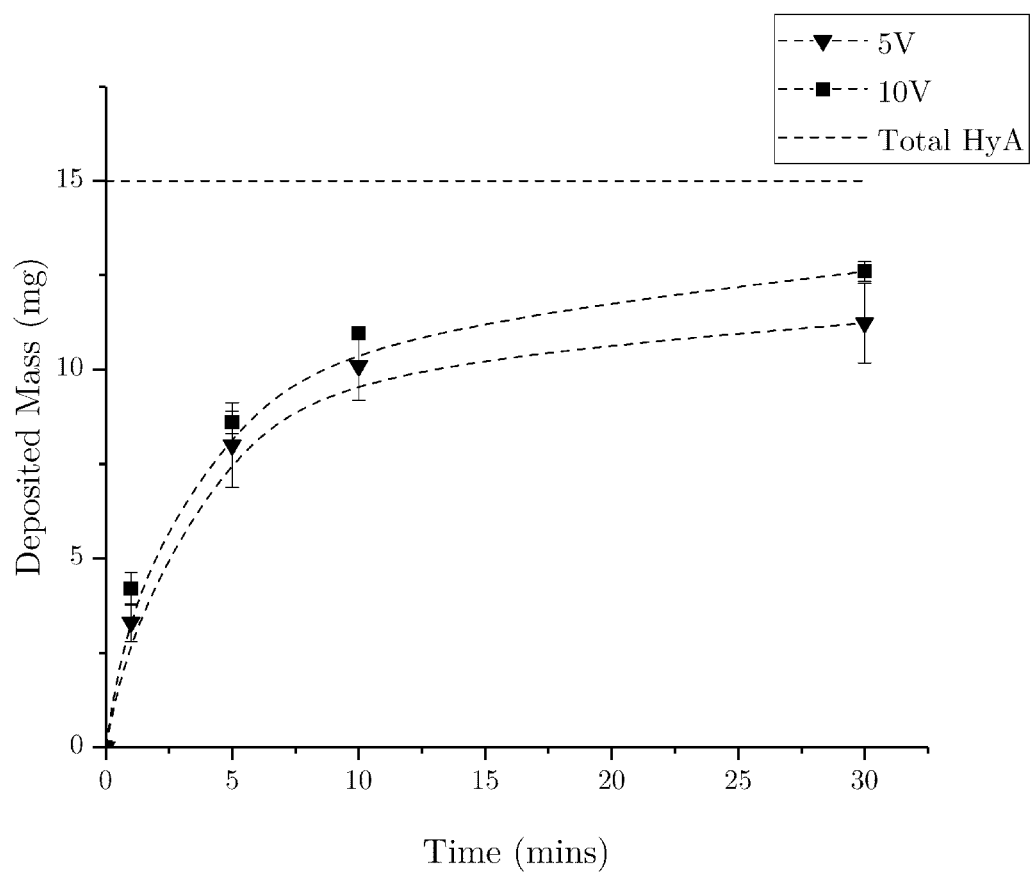
FIG. 9 shows deposition of hyaluronic acid films as a graph of deposited mass of hyaluronic acid against time for deposition by DC-EPD at 5V, and 10V.

To examine the deposition kinetics for HyA DC-EPD films, we measured the mass deposited against time for two different voltages, shown in FIG. 9. For deposition of ceramic materials at constant voltage, it is accepted that as the deposit forms there is an increase in the effective resistance, which leads to a decrease in the rate of deposition, and a reduction in the total mass that can be deposited with subsequent depositions [37]. However, from FIG. 9, we cannot see a difference in the mass deposited at each time point for different voltages. From this we can infer that, unlike in ceramic systems, there is not a large shielding effect caused by the formation of the HyA deposit on the electrode. We speculate that this may be because the initial deposit consists of a highly-porous, hydrogel which can allow charge carrying species to migrate through unimpeded, preventing an increase in the effective resistance at the electrode being seen. This is shown schematically in FIG. 7.

Additionally, DC-EPD deposition of HyA from a mixed aqueous ethanol solution of HyA resulted in production of films with a large number of gas bubble inclusions and damage to the structure of the film. Films were produced at 10V after an increasing deposition time. It was seen that even after 1 minute there are a large number of bubbles produced throughout the film. Bubbles increased with deposition time. The film produced after 30 minutes contained a large yellow/black discolouration. This discolouration is likely to be due to overpassing the normal potential of the electrodes, leading to migration of metallic impurities from the electrode into the deposit.

As we found it was not possible to produce macroscopically defect free HyA film by DC-EPD, we decided to produce HyA films by Pulsed-EPD. By varying the parameters associated with Pulsed-EPD, we found it possible to produce macroscopically defect free HyA films with V=10V, pulse length=30 ms, DC=30%, electrode spacing=7.65 mm.

Example 7: Collagen-HyA Multilayer Deposition

Figure 2:
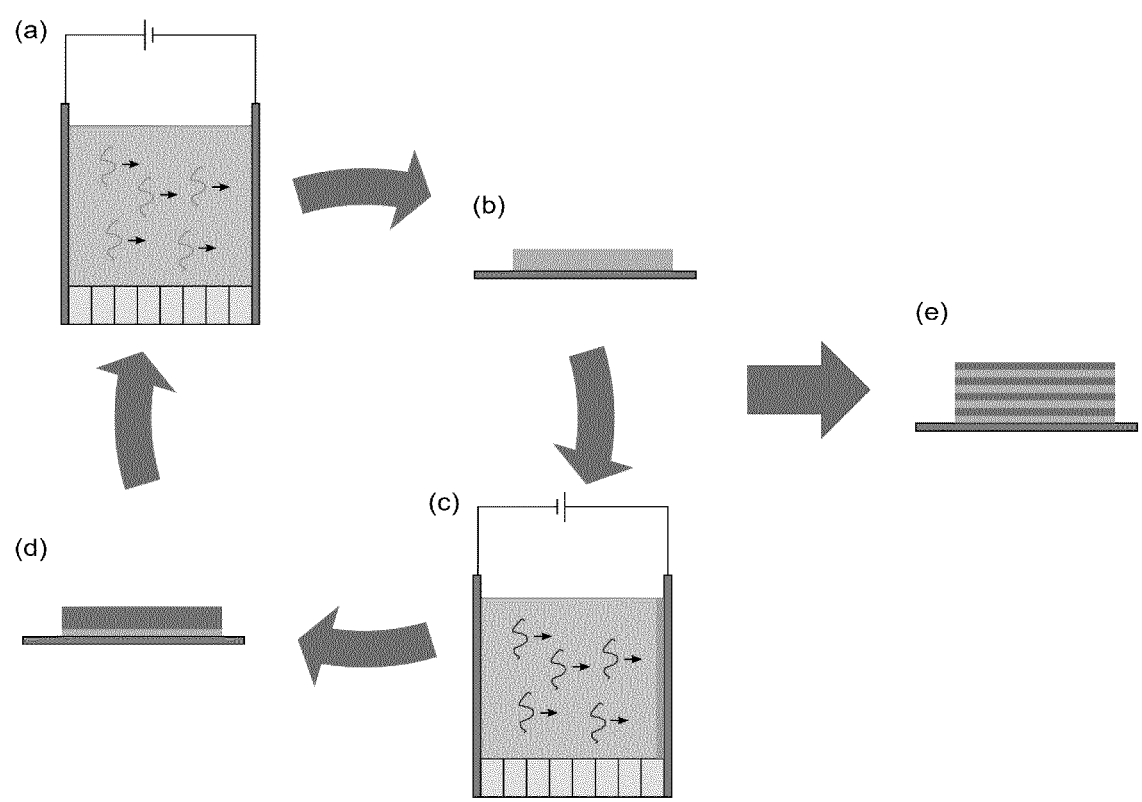
FIG. 2 shows the electrophoretic deposition of a multi-layered membrane; (a) a collagen suspension is placed in the EPD cell and an electric field applied, the collagen fibres of the suspension move towards the cathode where they form a solid or semi-solid structure, such as a membrane or gel. (b) The electrode is removed and allowed to air dry, significantly reducing the thickness of the deposit (c) The EPD cell is reassembled with the dry film still attached, a hyaluronic acid solution is placed in the EPD cell and an electric field is applied, opposite in polarity to the initial field. A HyA gel deposits on top of the previous collagen film. (d) The electrode is removed and allowed to air dry, the hyaluronic acid film reduces significantly in thickness. (e) Steps (a)-(d) are repeated and, after a desired number of cycles, a multilayer film is produced.
Figure 3:
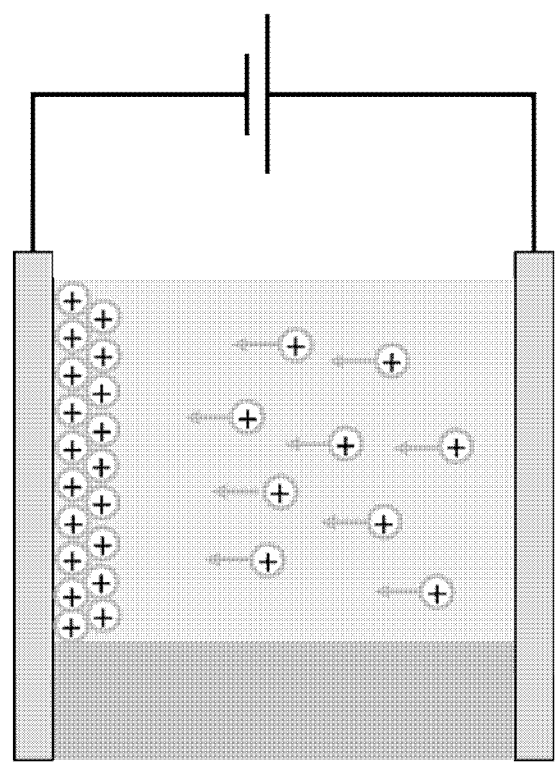
FIG. 3 shows a schematic of electrophoretic deposit of positively charged particles on the cathode during EPD.

In order to produce a multilayer structure, collagen and hyaluronic acid were laid down successively, with an air drying step between each deposition. A schematic overview of this method is shown in FIG. 2.

Figure 10:
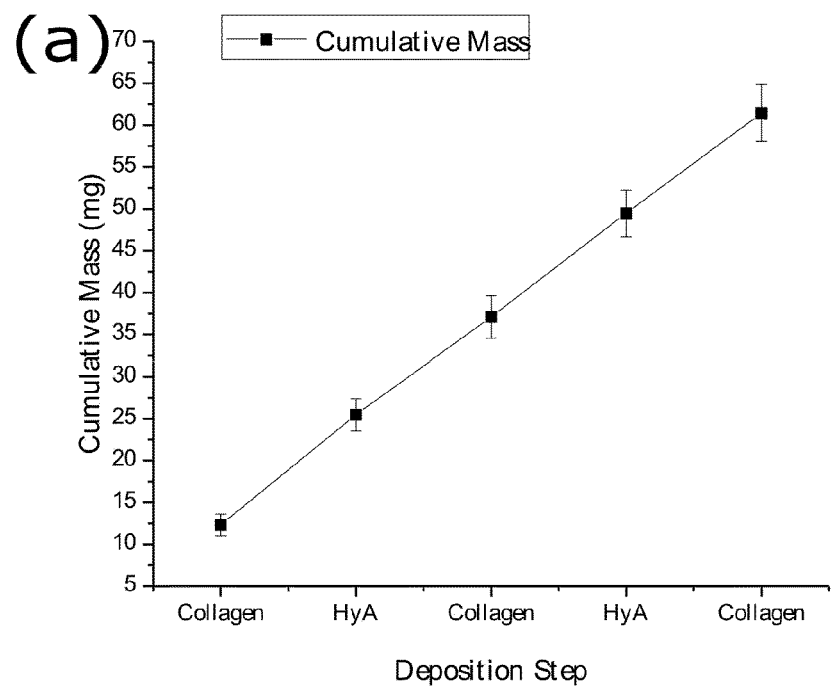
FIG. 10 shows the sequential deposition of collagen and hyaluronic acid by Pulsed-EPD: (a) Cumulative dry mass of a film formed by sequential deposition of collagen and hyaluronic acid by Pulsed-EPD, (b) SEI-SEM micrographs showing the structure of a dry film formed by sequential deposition of collagen and hyaluronic acid layers.
Figure 10:
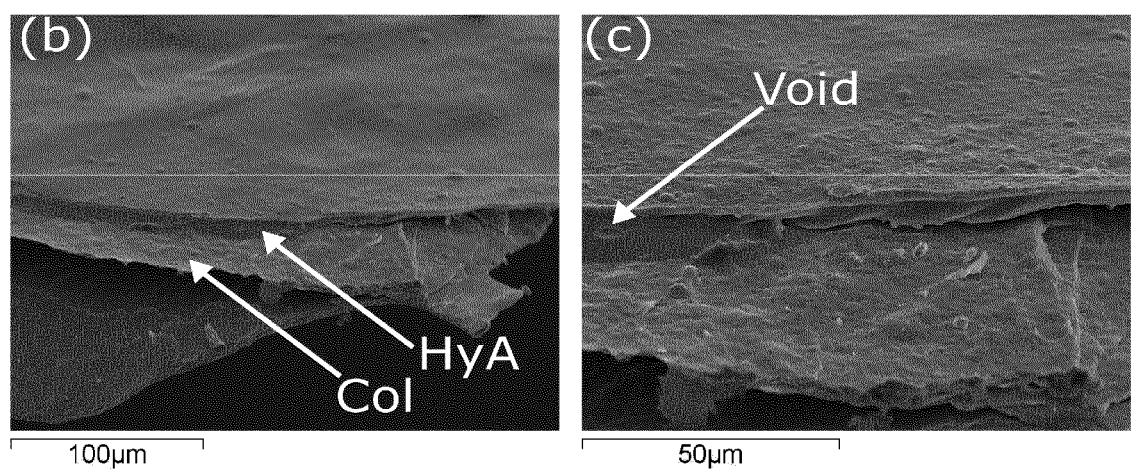

To determine if there was an increase in the cell resistance after deposition of both collagen and hyaluronic acid, we measured the mass after each deposition step, shown in FIG. 10, finding that there was no change in the deposition behaviour after previous film layers had been deposited.

We saw no increase in the effective resistance of the EPD cell after multiple depositions, as the mass that was deposited in each step is invariant. The rehydrated deposits are non-porous, potentially blocking ion transport from the bulk solution to the deposit. The exact mechanism for charge transfer to the electrode after the film has increased in density is unknown but there are a number of possible routes; the deposit could charge either through electron transfer between redox centres, counterion diffusion, diffusion of electroactive species, or a combination of these, it could still show have enough nano-porosity to allow for the unimpeded transport of ions even when dense, or structural changes could occur when an electric field is applied allowing for greater porosity.

Example 8: Collagen-HyA Multilayer Deposit Microstructure

The microstructures of the films generated in Example 7 were analysed. µ-CT investigation of the multilayer films, shown in FIG. 11a, showed that the collagen layers were clearly separate, with a layer of hyaluronic acid sandwiched between. There were no large voids caused by gas evolution during deposition.

Figure 11:
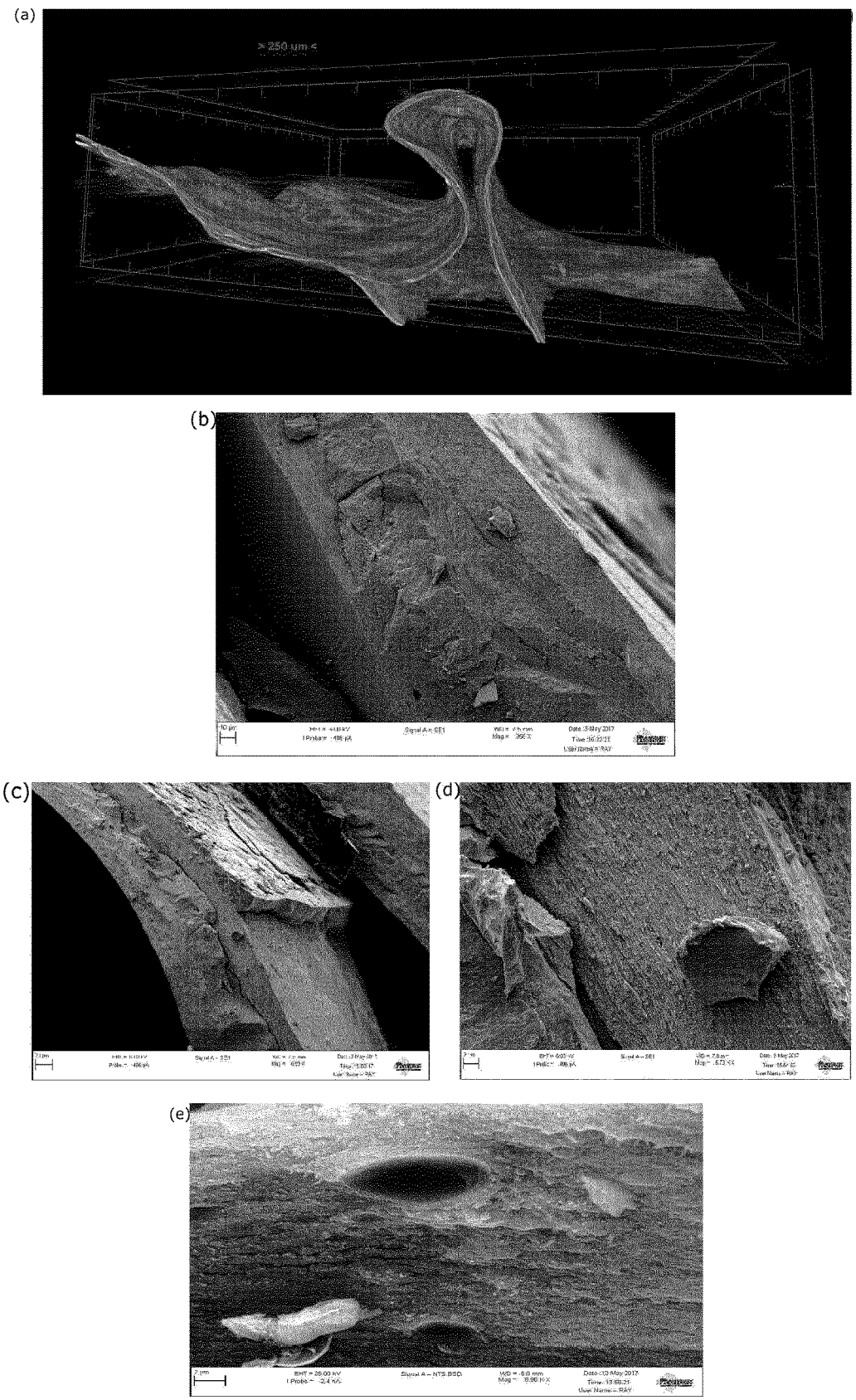
FIG. 11 shows the microstructure of collagen-hyaluronic acid multilayer films: (a) μ-CT image of a multilayer film formed by sequential deposition of collagen and hyaluronic acid layers, where one collagen layer has been sheared away, (b) cryoSEM micrograph of a hydrated multilayer film showing separate layers of collagen and hyaluronic acid, (c) cryoSEM micrograph of a hydrated multilayer film showing separation between collagen and hyaluronic acid layers, (d) cryoSEM of a hydrated collagen layer from a multilayer film showing a lamellar collagen structure, (e) BSD cryoSEM showing pore formation within a collagen layer in a hydrated multilayer film.

To examine the microstructure of the multilayer films in hydrated conditions, films were rehydrated in DI water before being frozen, fractured, and imaged by cryoSEM, shown in FIG. 11. In FIG. 11b the three collagen layers and two hyaluronic acid layers are clearly still distinct when rehydrated, with the hyaluronic acid layers swelling to a significantly greater thickness than the collagen layers. Additionally, the central collagen layer follows a curved path, indicating that the membrane did not rehydrate evenly, with some areas expanding to a greater extent than others. FIG. 11c shows an area of the multilayer film with a layer of collagen removed and a layer of HyA partially stripped away. The layer of collagen revealed is relatively flat, with no evidence of intrusion of HyA into its surface at any point, additionally, there are no collagen fibres visibly embedded within the HyA layer. The different construction of the collagen and HyA layers is clearly visible in FIG. 11c, the hyaluronic acid layer appears as a non-porous, glassy layer, indicating a frozen hydrogel.

The collagen layer can be seen to comprise of layers of individual, micron scale collagen fibres packed together in a lamellar structure. This collagen structure can be more easily seen in FIG. 11d which shows a magnified view of the collagen layer. It is possible to see that the layer is made of individual collagen fibres laid down parallel to each other. It is to be noted that all of the collagen fibres appear to be lying in similar orientations, with few collagen fibres lying out of plane. Additionally, the structure of the collagen layer produced by P-EPD shows a microstructure more evenly dense than collagen membranes produced by casting shown in FIG. 8e, which have a microstructure consisting of "leaves" of dense collagen separated by regions of fibrillar collagen.

Figure 12:
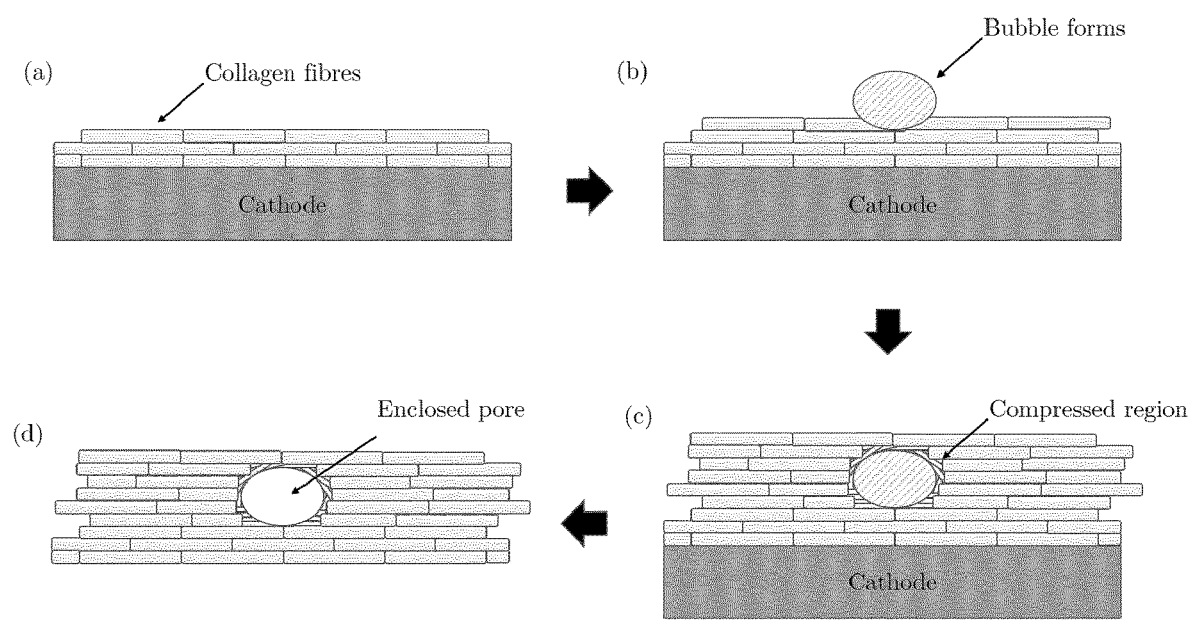
FIG. 12 is a schematic showing bubble formation in a collagen film. (a) Collagen fibres initially deposit onto the electrode, (b) A micro bubble forms on the surface of the collagen film, more collagen continues to be deposited around the bubble, (c) Collagen is deposited onto the bubble, leading to a skin of compressed collagen fibres around the bubble, (d) After deposition, the film is removed from the electrode, leaving a hollow pore in the collagen film.

FIG. 11e shows a BSD micrograph of a section through a void within a collagen layer. The collagen at the edge of the pore appears compressed, indicating that the bubble was present while new layers of collagen were deposited over it, encapsulating the gas within the film. Though the size of the gas bubble is large compared to the size of the individual collagen fibres, it has only led to a local distortion in the structure of the film. A schematic showing the bubble formation is shown in FIG. 12; it shows that bubbles form on top of previously laid down collagen fibres, where they grow at a rate slower than the rate of new collagen deposition. This leads to the encapsulation of the bubbles within a surrounding matrix of collagen, the collagen local to the bubble shows evidence of compression, caused by the force of the collagen fibres that are being added to the deposit.

While the multilayer structures produced herein are comprised of 5 layers of similar thickness, the lack of an increase in EPD cell resistance seen after multiple depositions indicates that membranes with thicker layers, and composed of a greater number of layers should be possible to produce using the same methodology. In addition, a number of other biological molecules could be incorporated into these multilayer films, allowing the mechanical and chemical properties of the membranes to be tailored to specific clinical needs. Furthermore, as these multilayer membranes are produced in situ we can produce non-planar membranes and coatings easily by varying the shape and conductivity of the underlying electrode. Together, the fundamental flexibility of the EPD process allow for creation of a range of widely varied biological multilayer membranes.

Example 9—Effect of Dialysis of Collagen Suspensions on Pulsed-EPD

Figure 13:
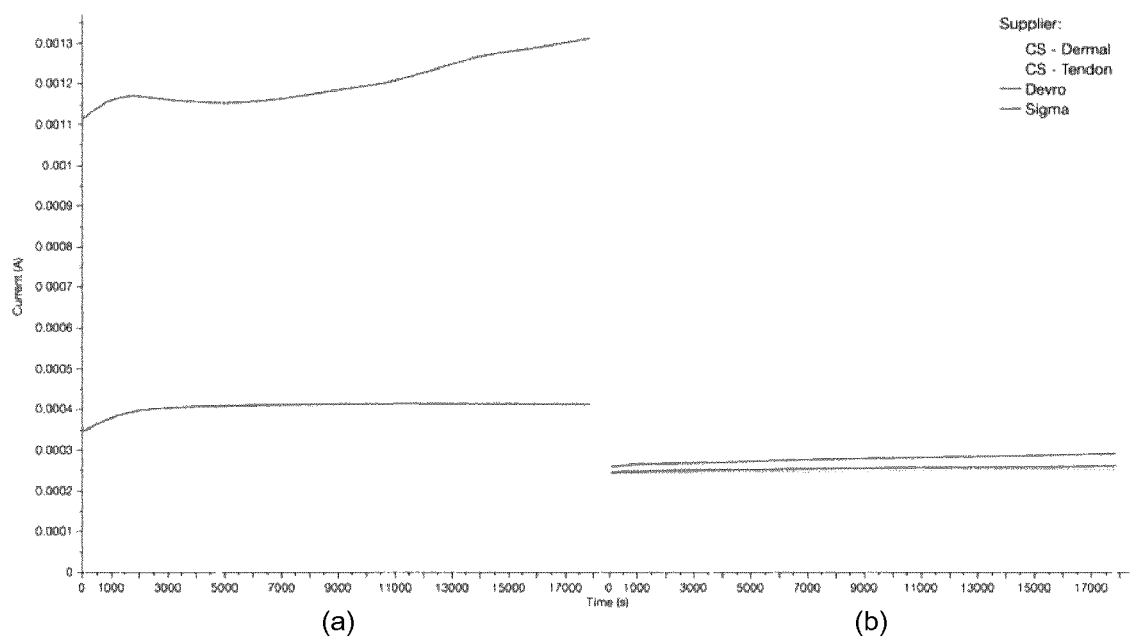
FIG. 13 shows the effects of dialysis on collagen suspensions: (a-b) current profiles during Pulsed-EPD (voltage=5V, pulse length=25 ms, electrode spacing=7.65 mm, DC=50%) for different collagen 1 slurries without (a) and with (b) dialysis.

A panel of collagen I suspensions was generated and dialysed in deionised water before being used for Pulsed-EPD. The collagen solutions were visibly clearer following dialysis. Without dialysis, the current during Pulsed-EPD for varies greatly between the different collagen solutions (FIG. 13 a), despite being the same type of collagen, i.e. collagen I. However, after suspensions have been dialysed, they all behave in the same way (FIG. 13 b). Given the lower current exhibited following dialysis, it would seem that dialysed suspensions can be run at higher voltages, reducing deposition time.

Example 10—Deposition of Collagen Films onto a Sacrificial Layer

Figure 14A:
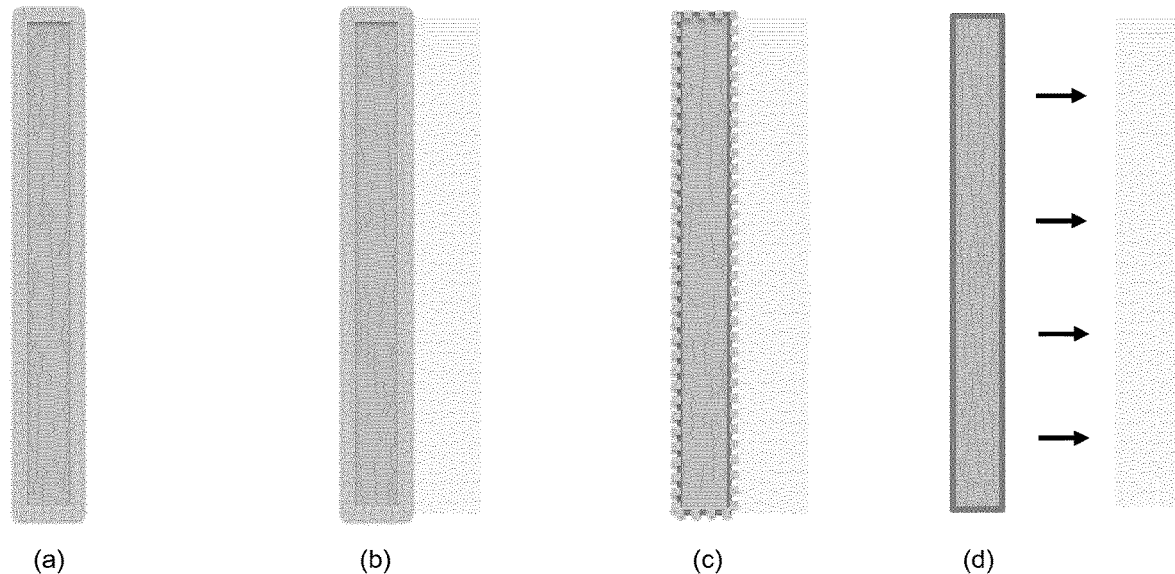
FIG. 14A is a schematic view of deposition onto a sacrificial layer: (a) electrode substrate is coated in cellulose acetate, (b) collagen is deposited onto the substrate by Pulsed-EPD, (c) once collagen is dry cellulose acetate is dissolved in acetone, (d) the collagen is liberated and retrieved from the substrate without any damage.

In order to provide more recoverable collagen films, a sacrificial layer of cellulose acetate was deposited onto the electrode substrate as described previously (S. A. Hasan, et al, ACS Nano, vol. 4, no. 12, pp. 7367-7372, 2010). A collagen layer was deposited onto the coated electrode by pulsed-EPD, and the electrode removed whilst the collagen dried. Once dry, acetone is added to dissolve the sacrificial layer, liberating the collagen layer from the electrode substrate and allowing recovery without any damage. This is shown schematically in FIG. 14A. In the absence of a sacrificial layer, the collagen layer cannot be released from the electrode surface without mechanical separation.

Figure 14B:
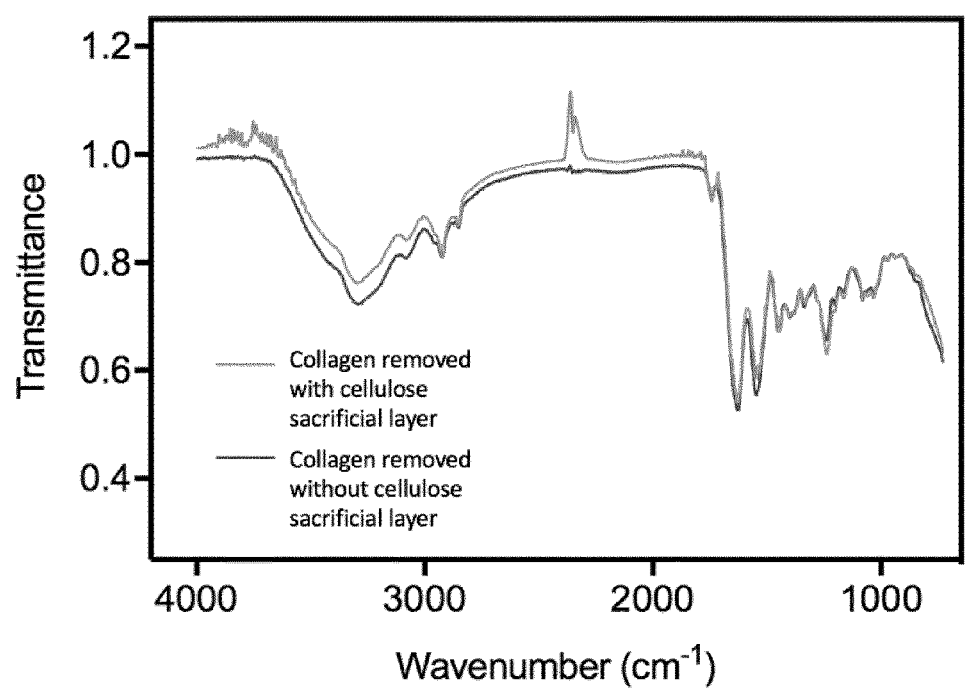
FIG. 14B shows the FTIR spectra of a collagen membrane prepared with a sacrificial layer and a collagen membrane prepared without one.

The fourier-transform infrared (FTIR) spectra of a collagen membrane prepared on a sacrificial layer of cellulose acetate and a collagen membrane prepared without a sacrificial layer (FIG. 14B). The spectra were found to be the same, indicating that the cellulose acetate layer is successfully removed during the acetone removal step.

Figure 14C:
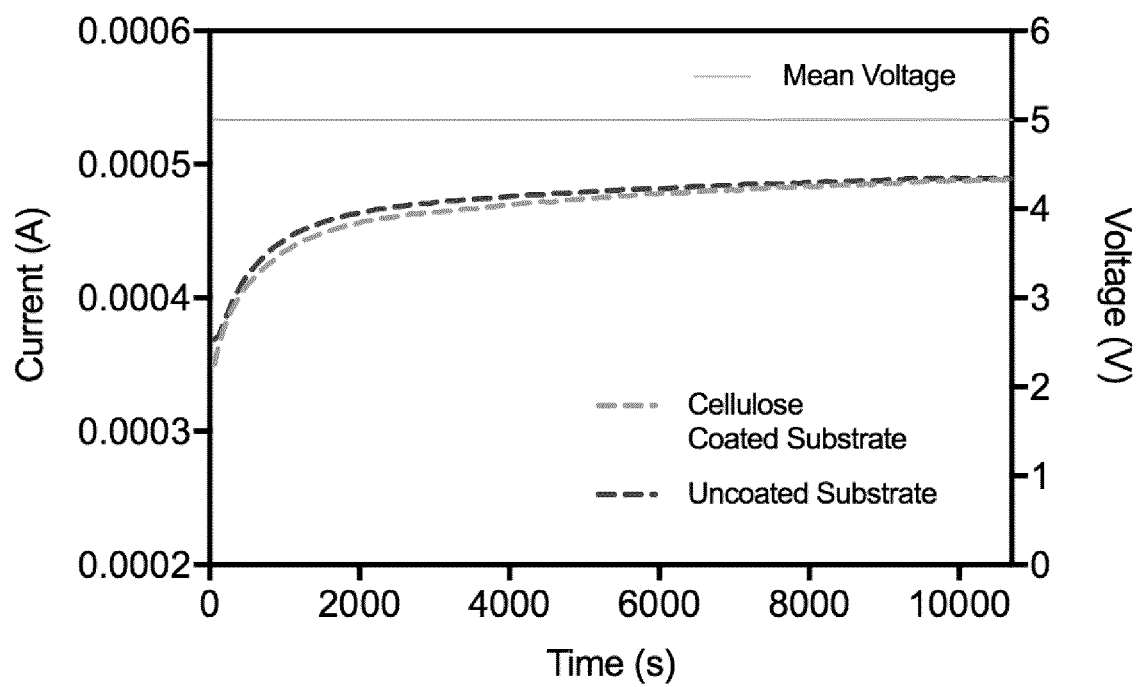
FIG. 14C shows the currents during membrane deposition on an uncoated substrate and a substrate coated with a cellulose layer.

The addition of a sacrificial layer of cellulose acetate was found to have no effect on the current required for deposition of collagen (FIG. 14C).

Example 11—High Voltage DC-EPD

Figure 15:
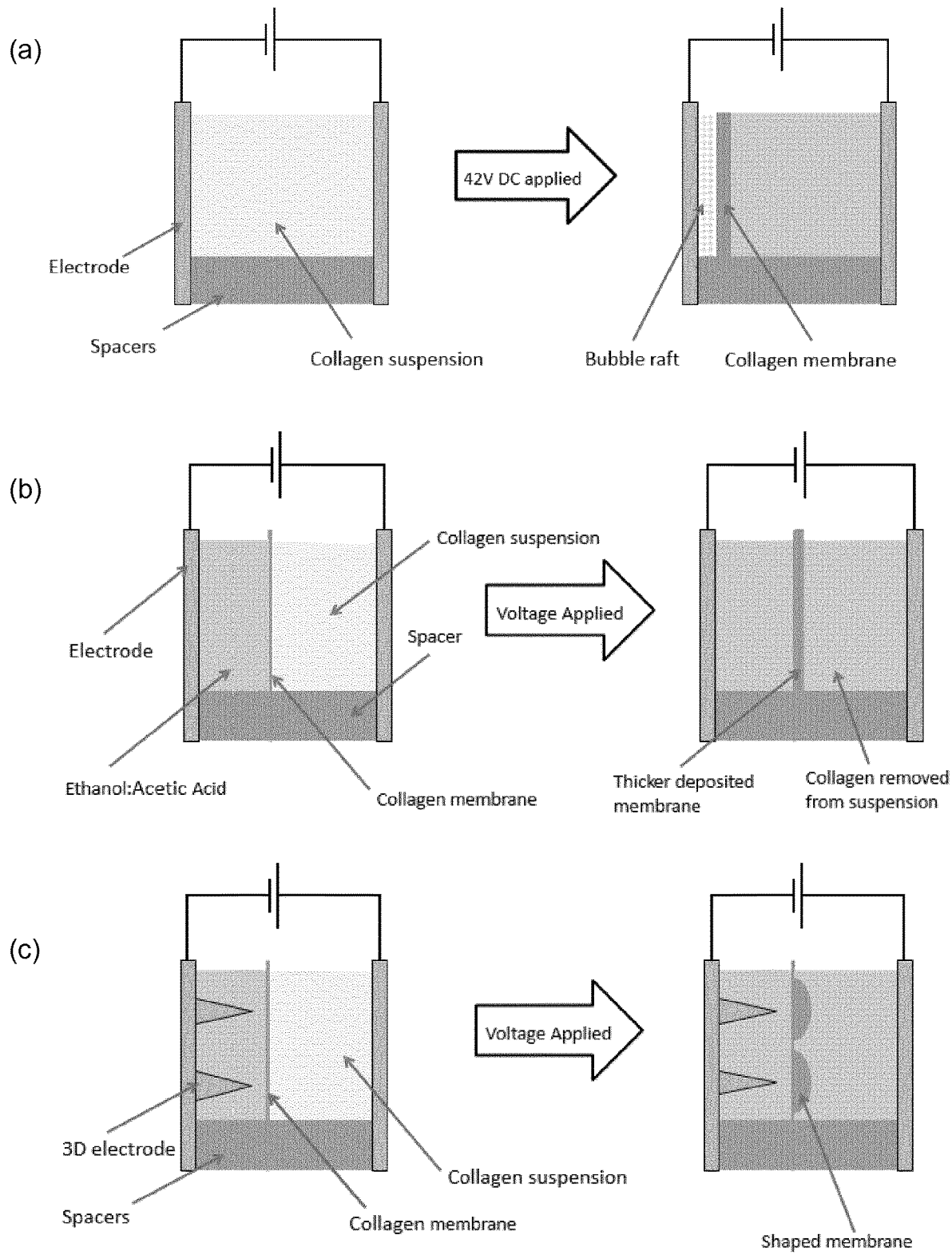
FIG. 15 shows alternative EPD protocols: (a) is a schematic of high voltage DC-EPD resulting in a collagen membrane deposited on a bubble raft. The membrane is not attached and can be manipulated immediately. (b) is a schematic of DC-EPD onto a suspended collagen membrane. Bubbles form at the electrodes but do not interfere with deposition. (c) shows that, using a 3D shaped electrode with the suspended membrane protocol of FIG. 15 (*b*), we can control the shape and strength of the electric field, resulting in the formation of a shaped membrane.

In an alternative protocol, collagen deposition by DC-EPD was performed at high voltage (42V). At such a high voltage, a large number of bubbled form at the electrodes. However, a collagen membrane still forms. Application of a high voltage to a collagen suspension leads to the formation of a collagen membrane on a bubble raft, and not in direct contact with the electrode (FIG. 15a). The membrane is not attached to the electrode and can be manipulated immediately.

Example 12—Suspended Membrane DC-EPD

This is currently performed using DC-EPD but it is conceivable that use of P-EPD would be useful for the final properties of the deposited membrane. In an alternative protocol, a collagen membrane was suspended between two electrodes and held in place by spacers effectively defining the electrophoresis cell into two sub-compartments or chambers (FIG. 15b). A collagen suspension was loaded into the compartment formed between the membrane and the anode, whilst ethanol:acetic acid was loaded into the compartment between the membrane and the cathode. DC-EPD was otherwise performed as normal.

In this way, we can deposit to a membrane suspended between two electrodes by applying an electric field. Deposition occurs onto the suspended membrane. Whilst bubbles form at the electrodes, these do not interfere with deposition.

Figure 28:
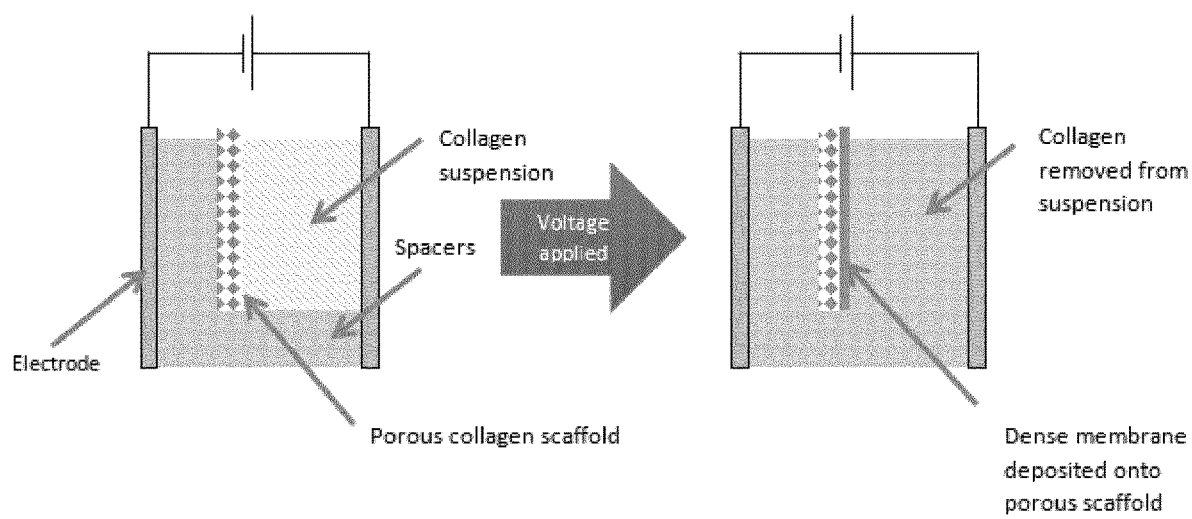
FIG. 28 shows a schematic drawing of electrophoretic deposition of a collagen membrane onto a porous scaffold. A porous collagen scaffold is suspended in an EPD cell, and collagen suspension is placed on one side, and another liquid (e.g. water) on the opposing side. An electric field is applied across the EPD cell, causing the collagen to move towards the porous scaffold where it deposits, leaving a dense collagen membrane on the surface of the porous collagen scaffold.
Figure 29:
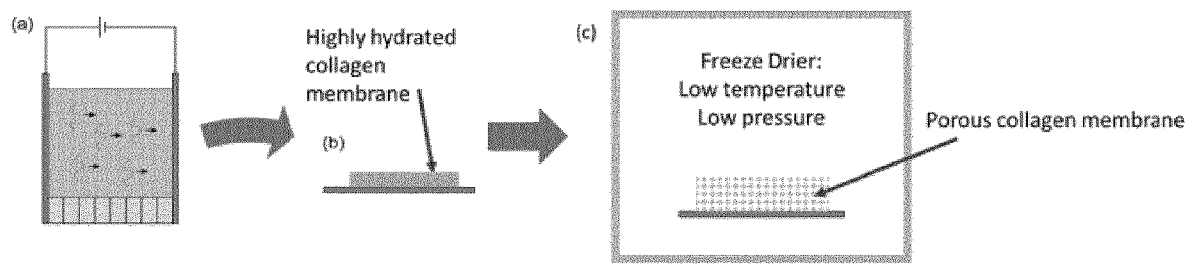
FIG. 29 shows a schematic drawing of fabrication of an expanded collagen membrane via EPD; (a) Collagen suspension is deposited by EPD; (b) the highly hydrated collagen membrane is removed from the EPD cell after deposition; (c) the hydrated collagen membrane is lyophilised to producing a collagen membrane with internal porosity.
Figure 30:
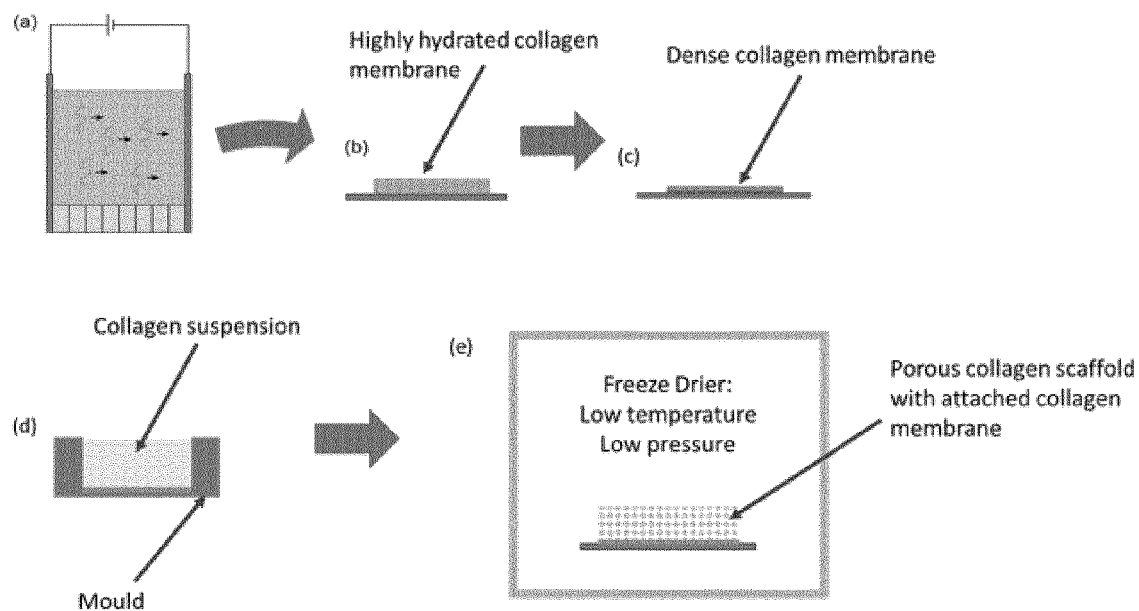
FIG. 30 shows a schematic drawing of fabrication of a porous collagen scaffold with an attached collagen membrane; (a) Collagen suspension is deposited by EPD; (b) the highly hydrated collagen membrane is removed from the EPD cell after deposition; (c) the collagen membrane is allowed to dry to a dense collagen membrane; (d) the membrane is placed in a mould and collagen suspension is added on top of the membrane; (e) the suspension and membrane are placed in a freeze-drier and lyophilised, producing a porous collagen scaffold with an attached collagen membrane.

FIG. 28 shows a further protocol for depositing a suspended membrane. Here, a porous collagen scaffold was suspended between two electrodes, effectively defining the electrophoresis cell into two sub-compartments or chambers. A collagen suspension was loaded into the compartment formed between the membrane and the anode whilst another liquid was loaded into the compartment between the membrane and the cathode. DC-EPD was otherwise performed as normal. A dense collagen membrane was deposited onto the porous collagen scaffold.

Using a 3D shaped electrode, we can control the shape and strength of the electric field, resulting in formation of a shaped membrane. This is possible even for deposition onto a suspended membrane and not directly onto the electrode substrate. A schematic view of this approach is provided in FIG. 15C Example 13—Formation of Shaped and Macro-Textured Films The shape of the collagen film produced by pulsed-EPD is in part determined by the shape of the electrode. We generated electrodes with a ridged macro-structure and performed pulsed-EPD deposition as described previously to produce collagen films with a corresponding ridged surface structure (FIG. 16 a). SEM microscopy revealed that the electrode structure was translated onto the collagen films even at the micro scale (FIG. 16 b). This was maintained during the drying and re-hydration of collagen films. These ridges provide internal grooves. The provision of such a textured surface, or other suitable textured surface, allows for the guidance of cell colonisation, for example.

Figure 16A:
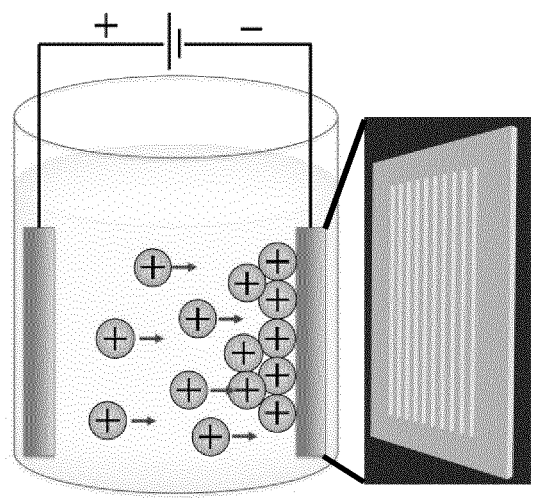
FIG. 16A shows a schematic view of pulsed-EPD deposition onto macro-textured cathode.
Figure 16B:
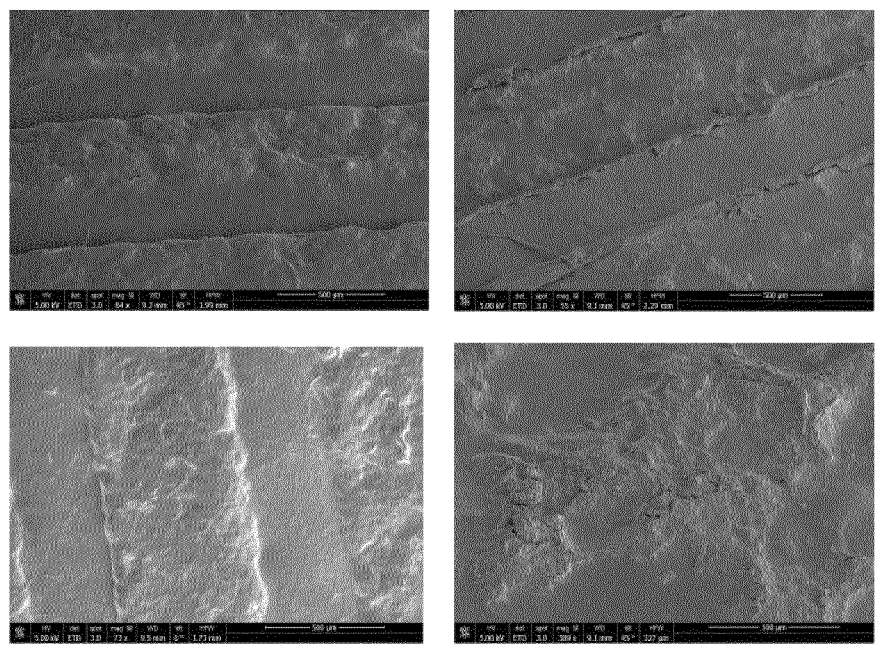
FIG. 16B shows SEM imaging of macro-textured collagen films.
Figure 16C:
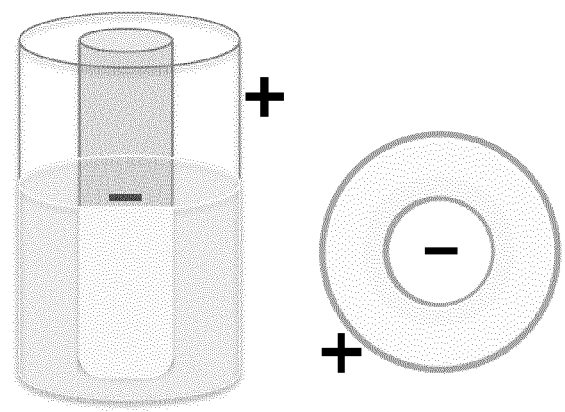
Figure 16D:
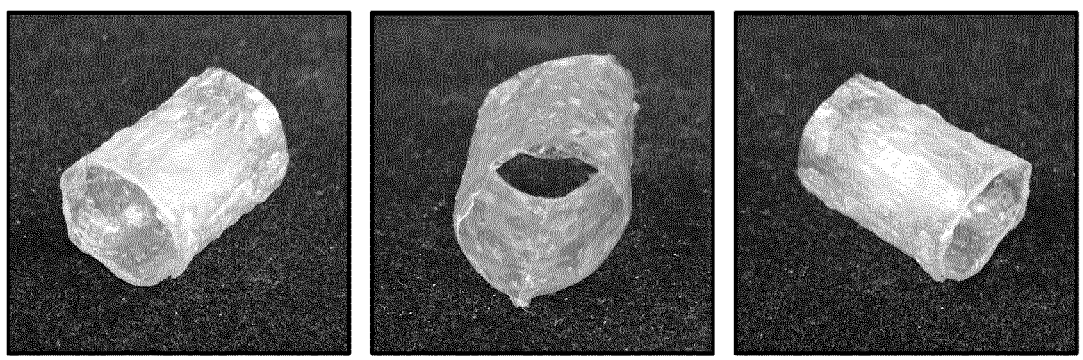
FIG. 16D shows collagen tubes produced by EPD.

Curved or otherwise non-planar membranes are difficult to produce using conventional methods known in the prior art. We further carried out pulsed-EPD using a tubular electrode as shown in FIG. 16C. A tubular cathode was placed within a larger anode, with collagen suspension between the two electrodes. Pulsed-EPD using these electrodes resulted in the deposit of collagen onto the cathode, which was subsequently removed to produce a seamless collagen tube (FIG. 16D). By varying the size, shape, and structure of the electrodes, it is possible to produce a range of optimised macro or micro-structured collagen membranes, which could find application in growing and/or directing cells. Specific larger structures, such as curved films or tubes, may be produced by manipulating the electrode shape, and could provide a better fit for the collagen gels when deployed. The size and shape of the electrode may therefore be manipulated to produce films of varying area and form.

Figure 16E:
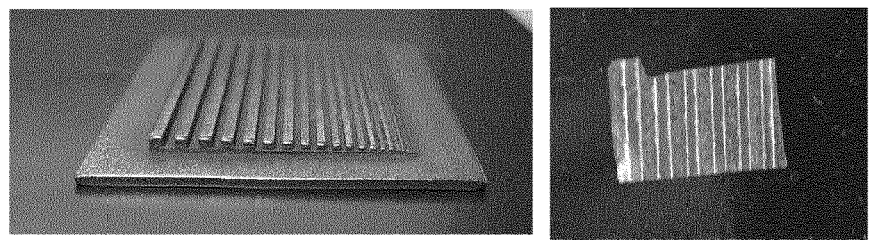
FIG. 16E shows a 3D printed electrode with grooves and a collagen membrane deposited onto the grooved electrode.
Figure 16F:
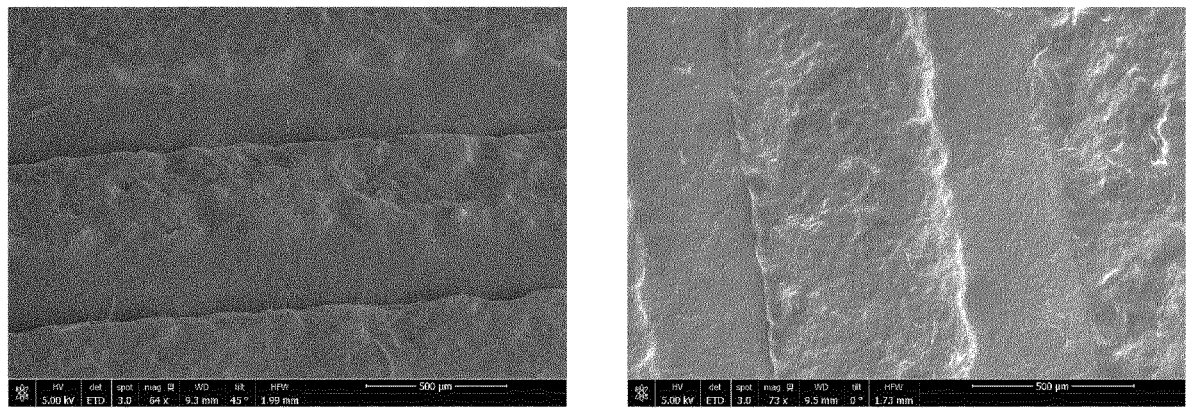
FIG. 16F shows SEM micrographs of shaped collagen membrane produced on the grooved electrode.

A 3D shaped electrode was produced by 3D printing (FIG. 16E). The electrode surface included a series of parallel grooves and ridges. Deposition onto this electrode produced a collagen membrane displaying parallel grooves and ridges (FIGS. 16E and F).

Example 14—Command Set Crosslinking of Multilayer Films

Figure 17A:
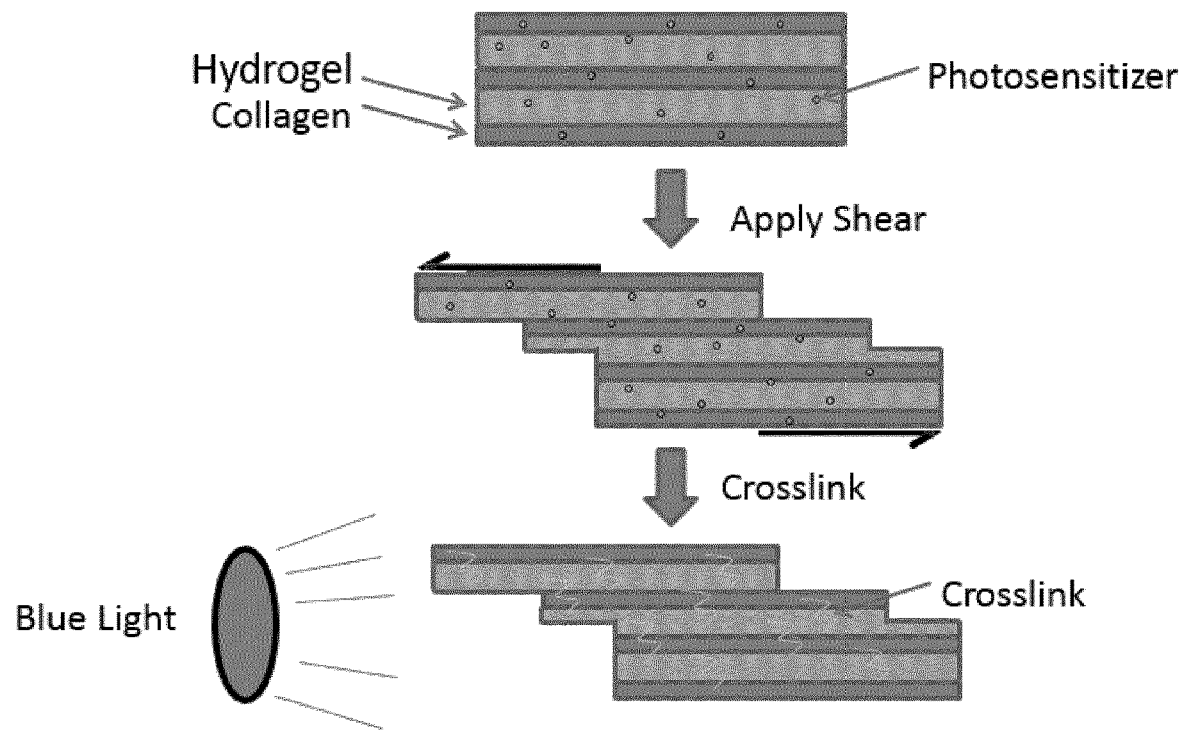
FIG. 17A shows shearing and command set crosslinking of a multi-layered collagen hydrogel membrane laced with photosensitive cross-linker. The hydrated multilayer film can be sheared into the desired shape. After being sheared the film is exposed to a blue light, activating the crosslinking agent. This fixes the film into sheared shape.
Figure 17B:
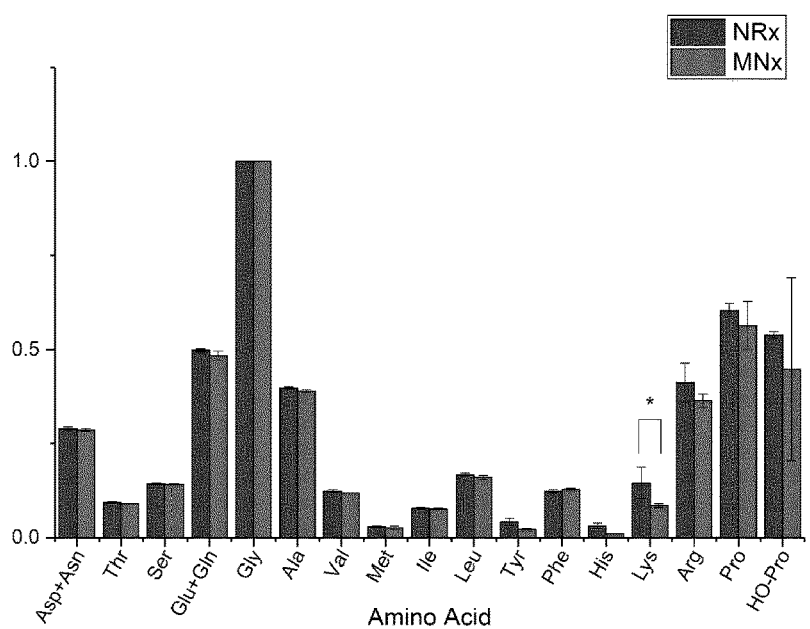
FIG. 17B shows the crosslinking of collagen membranes by amino acid analysis. NRx corresponds to un-crosslinked collagen samples, and MNx corresponds to samples that have undergone the riboflavin based crosslinking.

Deposited membranes may be laced with a variety of entities by adding them to the electrophoretic media prior to EPD or by soaking the membranes in the suspension after membrane formation. Collagen suspensions and HyA solutions were made and laced with a light-activated crosslinking agent. For collagen, this is riboflavin, whilst methacrylated end groups were used for HyA. The collagen suspensions and HyA solutions were then used to generate a collagen/HyA multilayer film using the protocol described in Example 7. Shear stress was applied in order to laterally shear the hydrated multilayer film (FIG. 17A). After being sheared the film is exposed to a blue light, activating the crosslinking agent. Suitable light sources for light curing include dental blue wavelength light sources. This fixes the film into sheared shape. This process may be performed in situ. Alternatively, the light-activated crosslinking agent may be added after generation of the collagen/HyA multilayer film.

The extent of crosslinking within collagen by riboflavin was determined by amino acid analysis. The quantities of each amino acid were determined by ion-exchange analysis of protein hydrolysates. This allows the determination of the quantity of each amino acid in the collagen except tryptophan and cysteine. The levels of each amino acid in collagen layers that have undergone light-activated riboflavin crosslinking (FIG. 14B; MRx) were compared with the levels in collagen layers that have not undergone light-activated crosslinking (FIG. 14B; NRx). The level of lysine was observed to drop in the cross-linked samples, indicating that crosslinking of lysine residues has occurred.

Examples 15A & B—Deposition of Collagen Films Containing Cells

Figure 18A:
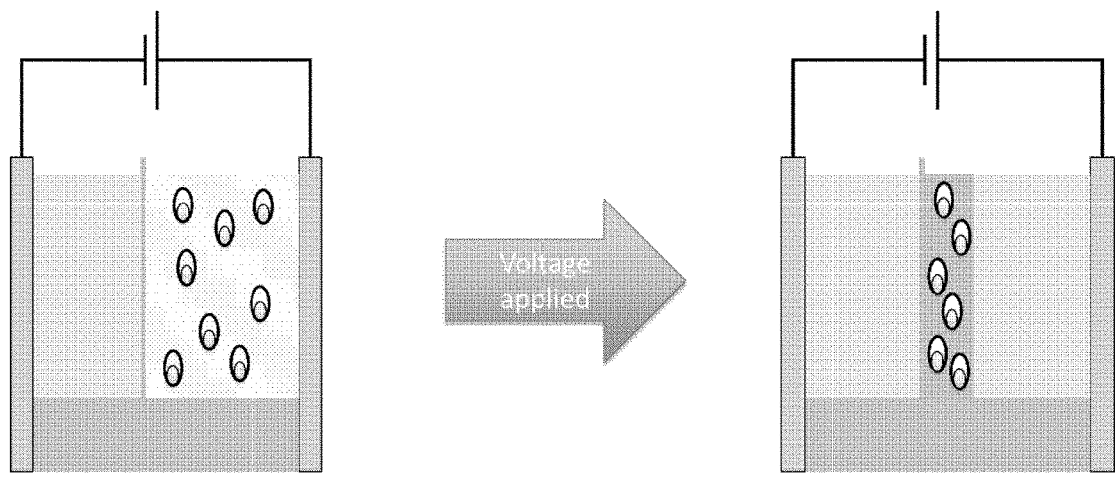
FIG. 18A is a schematic of EPD of a collagen and cell co-suspension to produce a collagen film laced said cells.

Collagen suspensions supplemented with salts and other factors to support cell viability may be laced with living cells prior to film formation by EPD (FIG. 18A). Voltage may be applied by pulsed or DC-EPD.

The resulting collagen films contain the cells incorporated into the collagen matrix, lying dormant, allowing for easy transportation before being reactivated at the destination. The location and function of the cells can be chosen together to complement wound healing and tissue regeneration.

Figure 18B:
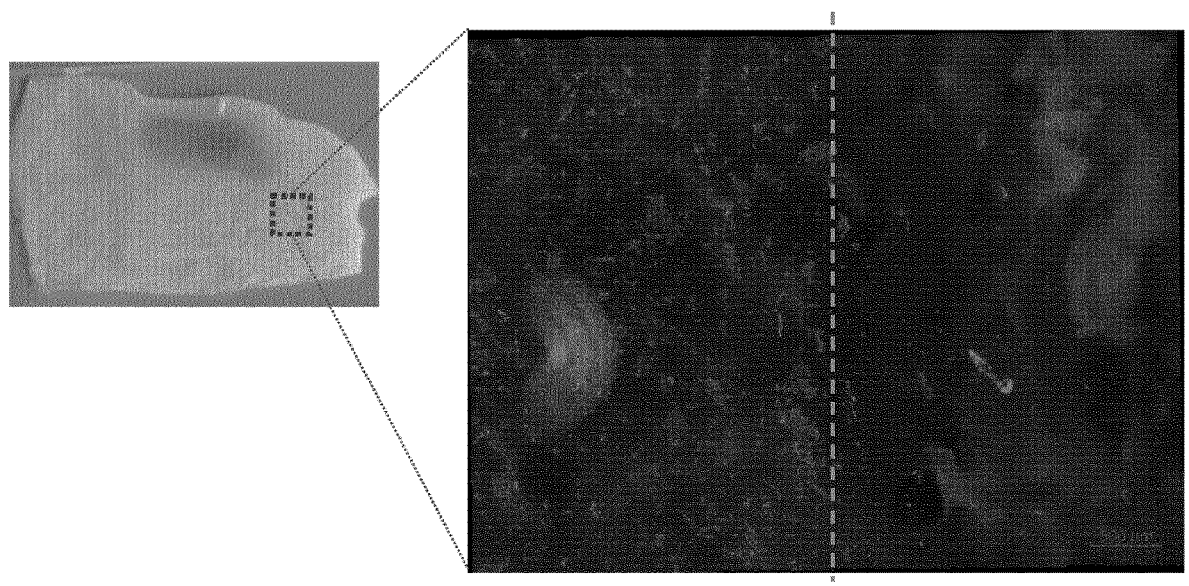
FIG. 18B shows, on the left, a photo of the collagen membrane onto which cells were deposited, with the approximate boundary of the cell deposition region highlighted, and on the right, a fluorescence micrograph which shows the location of cells as blue dots. The left side of the micrograph exposed to an electric field contains a large number of cells, and the right side not exposed to an electric field shows no cells, indicating that cells have been deposited by EPD.

Example 15A: A collagen membrane was suspended in an EPD cell, as shown in FIG. 18A and a collagen suspension containing cells was placed on one side of the membrane and an acetic acid solution on the other side of the membrane. A voltage was applied across the cell, moving the collagen and cells towards the membrane, where they deposited. The membrane was removed from the cell and stained using a DAPI stain. DAPI (4',6-diamidino-2-phenylindole) is a fluorescent stain that binds to the cell DNA, which when excited with the correct wavelength light allowed for highlighting of viable cells during fluorescent microscopy. Viable cells were clearly visible within the membrane (FIG. 18B).

Figure 31:
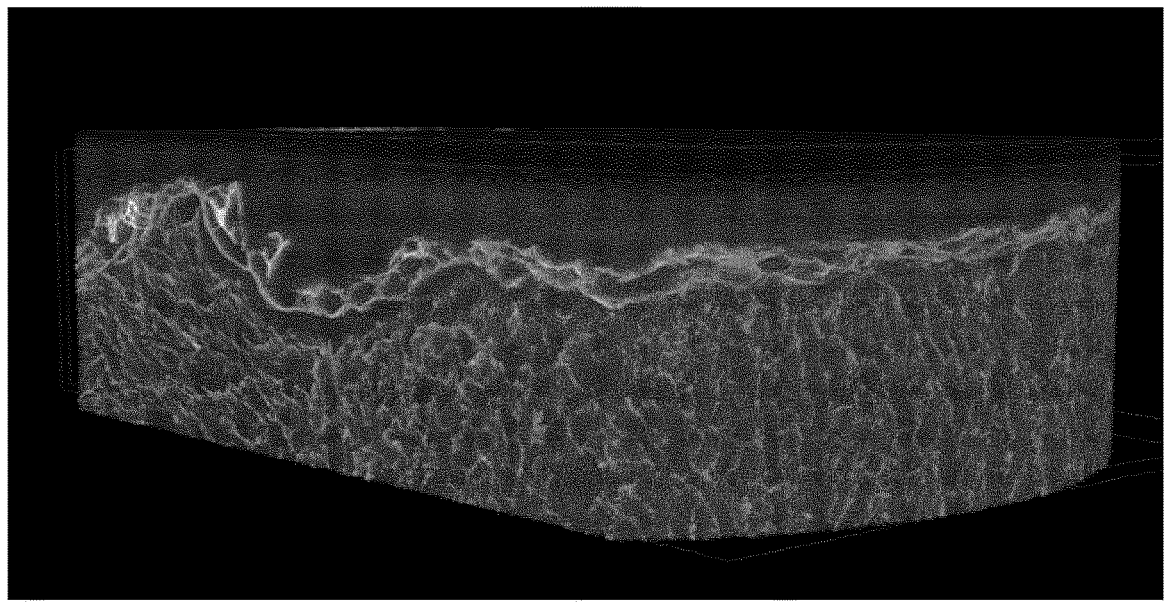
FIG. 31 is a µ-CT image of a porous collagen scaffold with porous collagen membrane attached.

Example 15B: In an alternative arrangement, shown in FIG. 31 ((a) being a side-view, (b) being a plan-view), two collagen membranes were suspended in an EPD cell, to thereby form a 3-chamber system. A spacer was used to hold the collagen membranes. A 0.25% collagen suspension containing cells, 0.03 g/L hyaluronic acid and various salts (30 mM NaCl, 40 mM BISTRIS, 20 mM EPPS, 170 mM sucrose, 10 mM glucose) was placed in the center chamber between the two collagen membranes. The outer two chambers were both filled with a buffer liquid—the buffer liquid is flowed through these chambers during the electrophoretic deposition. The chamber of the cathode side was filled with a cathode margin buffer solution comprising 300 mM NaCl, 40 mM BISTRIS, 20 mM EPPS, and 75 mM sucrose. The chamber of the anode side was filled with an anode margin buffer solution comprising 150 mM sodium sulphate, 40 mM BISTRIS, and 20 mM EPPS. Alternative buffer solutions suitable for use in this method can be found in work by Weber et al. "Applications of binary buffer systems to free flow cell electrophoresis" (2000), ELECTROPHORESIS, 21: 325-328.

Figure 32:
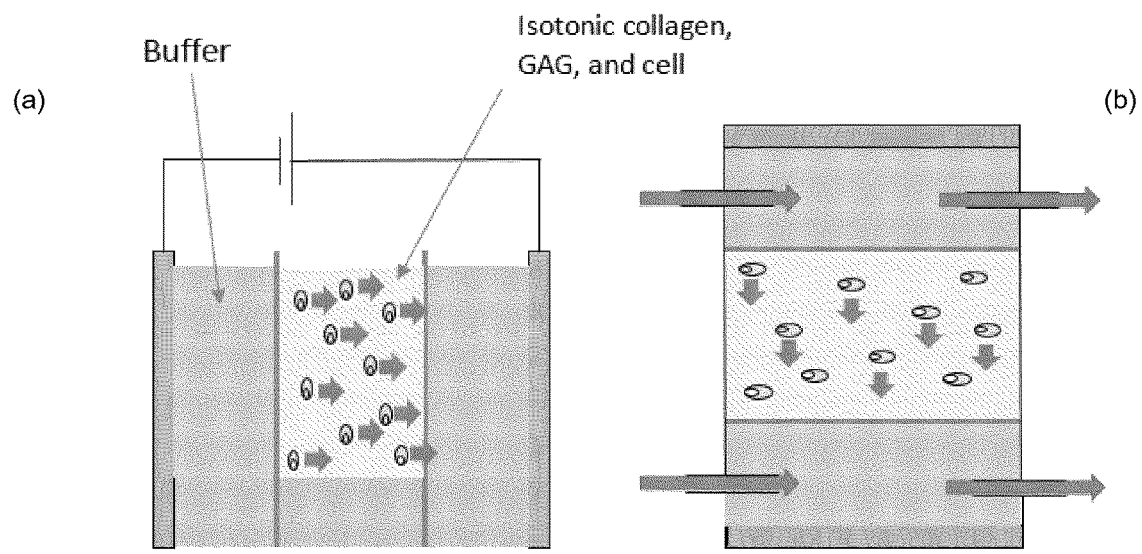
FIG. 32 is a schematic showing (a) a side view, and (b) a plan view, of EPD of a collagen and cell co-suspension to produce a collagen film comprising cells.
Figure 33:
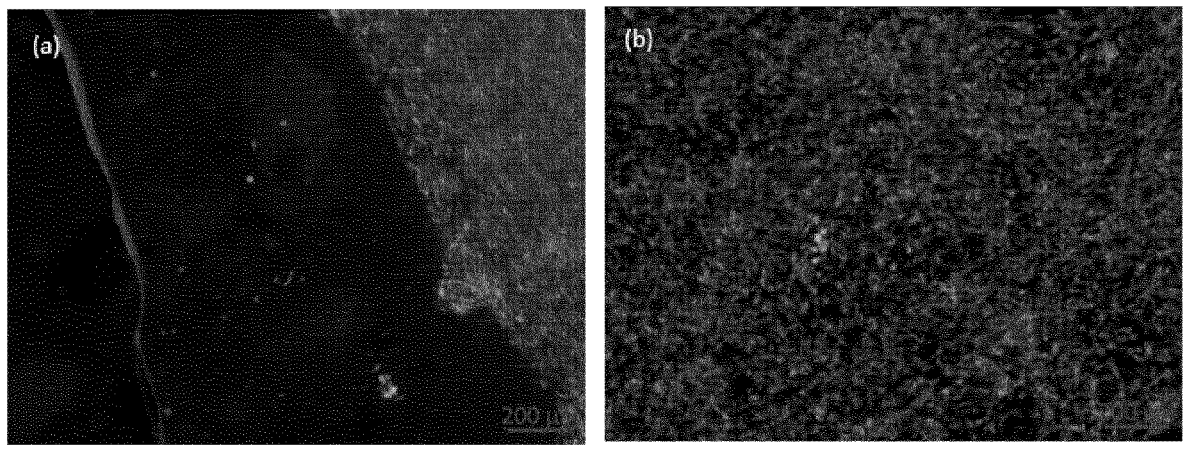
FIGS. 33 (*a*) and (*b*) are fluorescence images of cell deposited membranes stained with calcein AM and ethidium homodimer-1, green shows live cells and red dots show dead cells.

An electric field of 20V was applied across the chamber for 10 minutes, after which the field was turned off, the cell disassembled and the membranes removed and placed into Dulbecco's Modified Eagle Medium (DMEM). After 24 hours in a cell incubator at 37° C. in a 5% $CO_2$, the cells are stained with LIVE/DEAD® (Invitrogen, L3224) as described in the manufacturer provided protocol, briefly 2 µM calcein AM and 4 µM ethidium homodimer-1 in PBS were added to the cells, which were then incubated for 30 minutes in a cell incubator at 37° C. with 5% $CO_2$, and imaged using a fluorescence microscope. Viable cells were clearly visible (FIG. 32 (a), (b)). Live cells appear green and dead cells appear red. The cells are visibly trapped in a deposited gel and at the side an area not exposed to the field can be seen to be predominantly free of cells.

Example 16—Alignment of Collagen Fibres within Films

Figure 19:
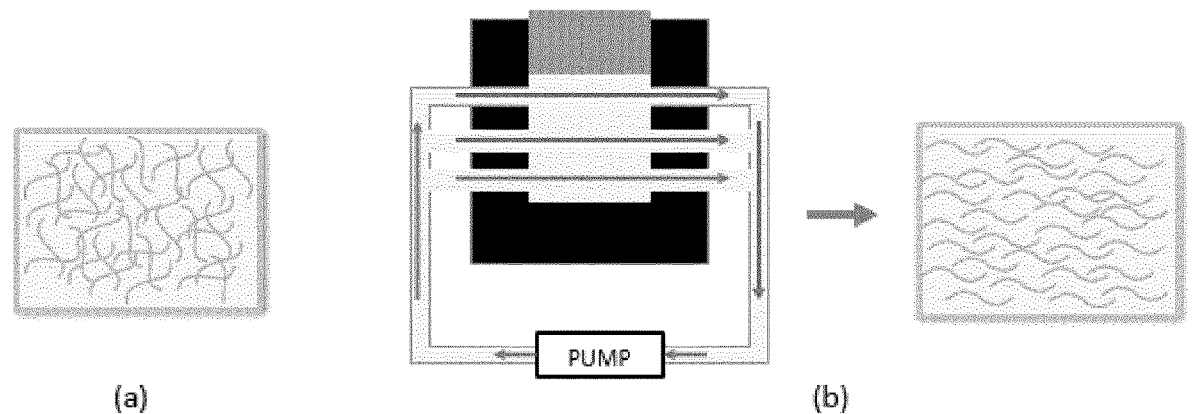
FIG. 19 is a schematic view of a pump-driven EPD cell that induces collagen flow during deposition, to force alignment of collagen with direction of flow. (a) Collagen fibres deposit in random orientation under normal EPD conditions, (b) flow during EPD aligns collagen fibres as they deposit.

Under normal EPD conditions, collagen fibres deposit in random orientation, within the plane of deposition, leading to a disordered film structure. In order to generate uniformly aligned collagen fibres, we provided an EPD cell with a pump to induce collagen flow during deposition and force alignment of collagen with the direction of flow. EPD was performed as normal with the circulating collagen suspension. As the fibres deposited, they did so in alignment, producing a uniformly directional collagen film. A schematic of this process is shown in FIG. 19.

Aligning collagen fibres within films can be used to tune mechanical properties. For example, suture pull-out resistance can be increased in all directions by using multilayer films in which each layer is aligned in a different direction.

Example 17—Measurement of Mechanical Properties and Effect of Cross-Linking

Cast Collagen Films

Cast collage films (i.e. not deposited by EPD) with and without crosslinking were subjected to tensile testing to determine the UTS. The following protocol was used:

A rectangular or dumbbell shaped sample is prepared of the membrane

Sample is rehydrated in a liquid medium at 37° C.

The initial thickness and width of the sample are measured. In the case of a dumbbell shaped sample, the thickness and width is measured at the narrow region of the sample.

The samples is clamped into appropriate grips of a mechanical testing machine and the separation between the grips is measured A tensile force is applied and the extension and applied force are recorded The tensile force is increased until the sample breaks The force is converted to a stress measurement using the recorded thickness and width (Stress=Force/Area)

The extension is converted to a strain measurement (Strain=Extension/Original Length)

Figure 20:
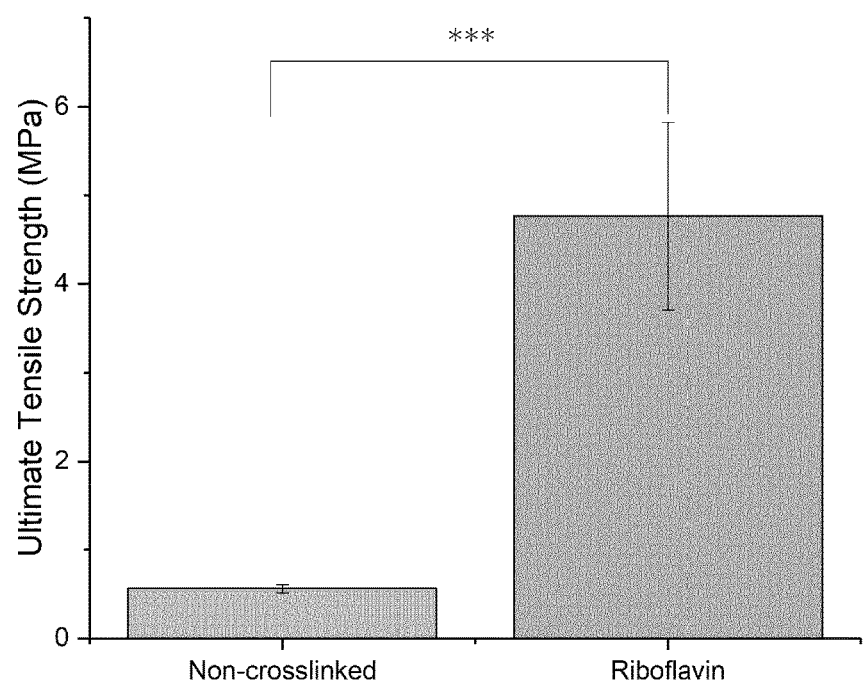
FIG. 20 shows the results of UTS testing of crosslinked and non-crosslinked cast collagen films.

The stress and strain are plotted onto a graph, with stress as the y axis and strain as the x axis The ultimate tensile stress is defined as the peak value on the stress-strain curve After testing the mean of each population and its standard deviation was determined, with the results shown in the table below and shown in FIG. 20.

|  | Average UTS (MPa) | StDev (MPa) |
| --- | --- | --- |
| Non-crosslinked | 0.56 | 0.04 |
| Crosslinked with Riboflavin | 4.77 | 1.06 |

The results in the table above refer to cast collagen films rather than EPD collagen films. This data backs up the amino acid analysis data. From this, it is reasonable to infer that EPD deposited collagen films will also respond with higher UTS when crosslinked.

EPD Collagen Films

Aligned and non-aligned collagen films were prepared by EPD according to the invention with an applied voltage of 10V, a pulse length 25 ms, duty cycle of 40%, and using a flow speed of 9 cm/minute (for the aligned film). The non-aligned films were formed without a flow being applied during deposition to thereby produce films having randomly orientated collagen fibres within the layer.

The films were crosslinked using riboflavin as described in example 14. The UTS of these films was determined as described above for the cast collagen films.

After testing, the mean of each population and the standard deviation was determined with the results shown in the table below:

|  | Average UTS (MPa) | StDev (MPa) |
| --- | --- | --- |
| Non aligned EPD collagen membrane | 3.53 | 1.12 |
| Aligned EPD collagen membrane (tested orthogonal to alignment) | 2.89 | 0.25 |
| Aligned EPD collagen membrane (tested parallel to alignment) | 6.34 | 1.48 |

This demonstrates that aligned collagen membranes are stronger in the direction of fibre alignment Coefficient of Friction of Multilayer Films The coefficient of friction between subsequent layers in multilayer membranes produced according to the present invention was also investigated for a 3 layer (collagen/hyaluronic acid/collagen) membrane and a 3 layer collagen/ methacrylated-hyaluronic acid/collagen membrane. The coefficient of friction gives a measure of how easily two items slide over each other.

The coefficient of friction for layer sliding was calculated using a custom linear reciprocating tribometer, designed by Jan Girman and disclosed in the article: Girman, Jan, University of Cambridge. Department of Materials Science Metallurgy, degree granting institution. "Novel Treatments for Spinal Facet Arthrosis", 2016, and by using the following protocol: A 10 mm diameter 316L stainless steel rod, with 4000 grit sand paper was traversed over the collagen and multilayer samples. The cycle frequency was set to 1 Hz. Samples were rehydrated in water at room temperature for 5 minutes prior to being tested. A normal force of 5.962N was applied by addition of weights to the tribometer, and the motor was allowed to run for a minimum of 60 cycles. Force was measured using a 10 kg s-type compression/tension load cell, and linear displacement was measured with a linear variable differential transformer.

The coefficient of friction was determined by initially plotting force vs time and determining the cycles under which steady-state sliding had occurred, then plotting these cycles as a force vs linear displacement graph. At the mid-point in the linear displacement the difference between the forward (trace) and backward (retrace) force readings was calculated and halved, giving the average friction force at the mid-point of travel.

From this, it was shown that collagen/hyaluronic acid/collagen layers could slide on the central layer, and a coefficient of friction of 0.00881±0.00178 was determined for the 3-layer collagen/hyaluronic acid/collagen multilayer membrane.

Similarly, collagen/methacrylated-hyaluronic acid/collagen membranes were prepared by EPD according to the present invention, using hyaluronic acid that had been methacrylated to 50% (Blafar Ltd., code: HA-MA301). These membranes were then crosslinked with riboflavin as in example 14 and the coefficient of friction was determined to be 0.0226±0.0042 for the collagen/methacrylated-hyaluronic acid/collagen multilayer membrane.

Example 18—Birefringence of Aligned Membranes and SEM Imaging of Aligned Membranes The optical birefringent properties of a polymer material directly correspond to the anisotropic structure within. Increasing anisotropy (or alignment) increases the optical birefringence of a material. The following experimental procedure was used to determine the birefringence of a membrane (protocol 'A'):
  The thickness of the membrane is first measured
  The membrane is placed in a polarised light microscope, between the analyser and the polariser lenses that are rotated 90° to each other.
  The sample is rotated to the maximum intensity of light passes through, 45°, and the colour of the sample is recorded.
  The colour recorded and the thickness of the sample are used with a Michel-Levy chart to determine the value of the birefringence of the sample. (Alternatively, a quartz wedge can be used to determine the value of the birefringence of the sample.)

Figure 21:
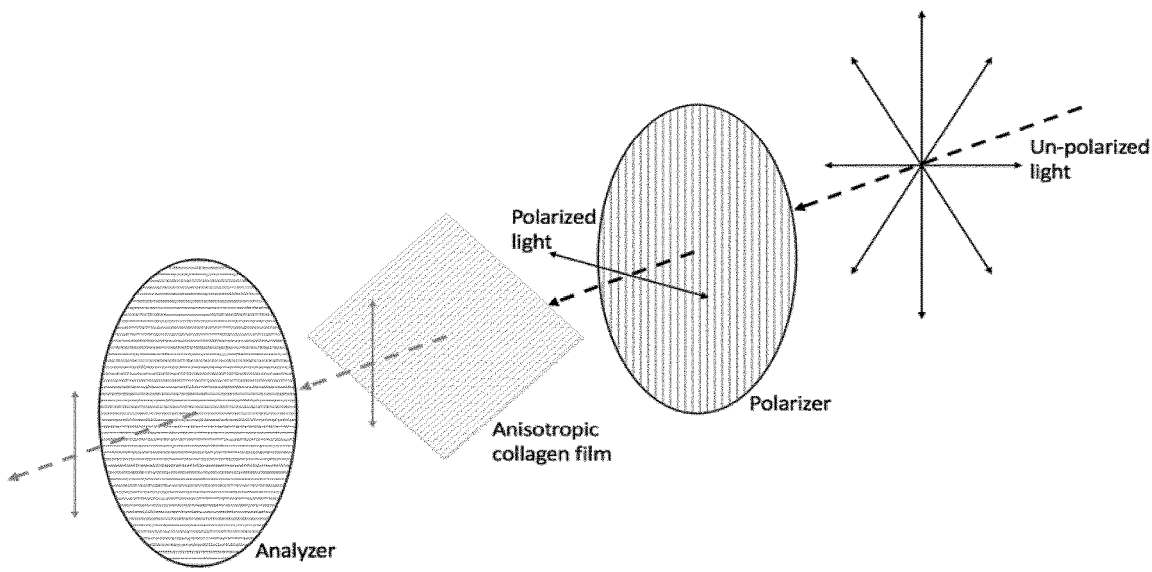
FIG. 21 illustrates schematically a process for testing the optical birefringence of a collagen film.

FIG. 21 illustrates schematically the process for testing the optical birefringence of a collagen film based on the steps set out above.

Collagen membranes were prepared using EPD, both with flow during deposition and without flow, thereby to form films without a preferential alignment direction of the collagen fibres and to form films with a preferential alignment direction of the collagen fibres. The thickness of the membranes were determined, prior to polarized microscopy, using micro-CT, which was found to be 40 µm. The samples were imaged in a polarized microscope, as described above.

Figure 22:
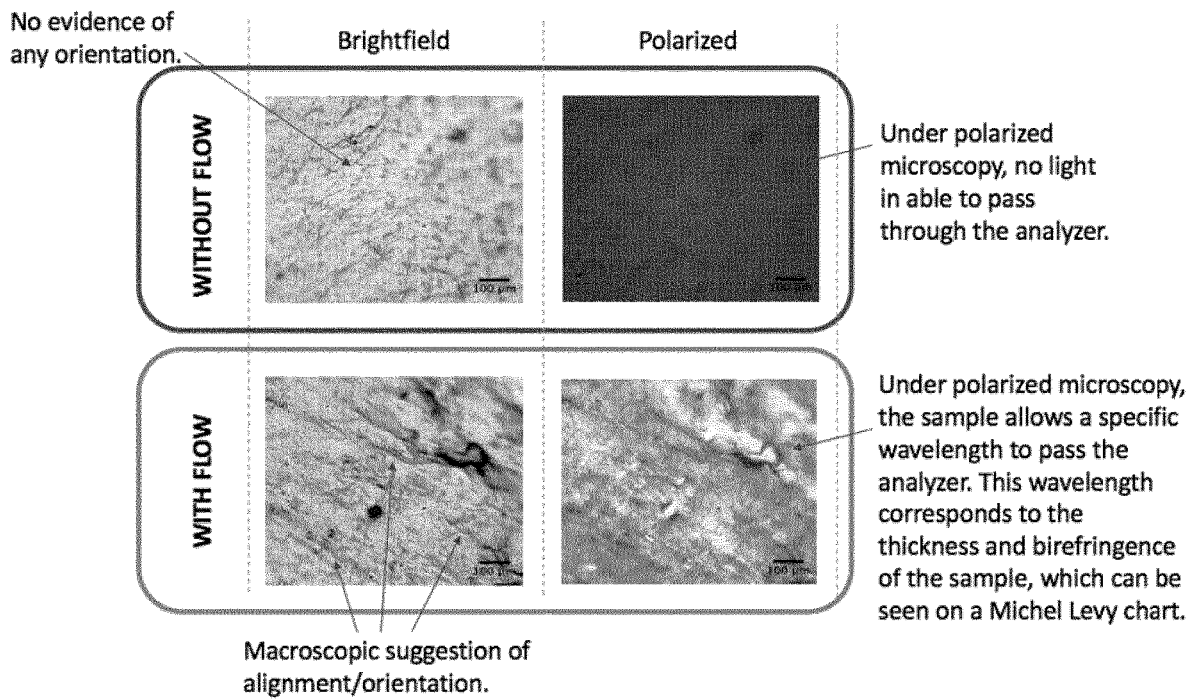
FIG. 22, which shows brightfield microscopy on the left, polarized microscopy on the right, collagen deposited without flow above, and collagen deposited with flow below) that where the collagen film is deposited in an environment in which there is relative movement between the layer deposition interface and the suspension of collagen fibres during deposition, there is measurable birefringence attributable to the sample.

The results from which are illustrated in FIG. 22, which shows brightfield microscopy on the left, polarized microscopy on the right, collagen deposited without flow above, and collagen deposited with flow below that where the collagen film is deposited in an environment in which there is relative movement between the layer deposition interface and the suspension of collagen fibres during deposition, there is measurable birefringence attributable to the sample. This compares with no measurable birefringence when the sample is deposited without such relative movement.

Based on the measurements carried out in the course of this work in line with the above protocol, the samples prepared with flow were found to show a colour when rotated to 45° to the cross polar lenses. This colour can be used with a Michel-Levy chart, to determine the birefringence along with the thickness of the samples. A typical birefringence of an embodiment of the invention, from the Michel-Levy chart, is 0.03. A typical minimum birefringence indicating a suitable degree of alignment of the collagen fibres is 0.015. These degrees of alignment are achievable for membranes deposited with flow, as described herein. In comparison, membranes deposited without flow typically have a birefringence of 0.00.

An alternative protocol (protocol B') for measuring birefringence of samples was used to determine the birefringence of some samples:
  The thickness of the membrane is first measured
  The membrane is placed in a polarised light microscope, between the analyser and the polariser lenses that are rotated 90° to each other.
  The sample is rotated to the maximum intensity of light passes through, 45°.
  A quartz compensator is inserted into the microscope, parallel to the sample layer.
  The quartz compensator is rotated until no light passes through the microscope eye-piece, and the angle of the quartz compensator is recorded.
  Using the angle, the retardation of light from the birefringent sample is calculated, using the following equation:

$$\text{retardation (nm)} = -0.004(\text{angle})^2 + 1.2539(\text{angle})^2 - 0.54(\text{angle}) - 5.3114$$

Birefringence is calculated using the retardation and sample thickness in the following equation:

$$\text{birefringence} = \frac{\text{retardation (nm)}}{\text{thickness (nm)}}$$

Example 19—Deposition of Collagen Films Containing Therapeutic Compound

A standard curve was prepared by measuring the absorbance of tetracycline in a 50% (v/v) ethanol in water at 360 nm using a UV-vis, with concentrations in the range 20-200 µg/ml. From this it was determined that in the range 20-80 µg/ml the absorbance at 360 nm is linearly correlated to the concentration of tetracycline dissolved.

80 µg/ml tetracycline was added to a 0.25% collagen suspension in 50% 0.05M acetic acid (dialysed), 50% ethanol. The suspension was placed into an EPD cell, and an electric field applied. A membrane formed on an electrode, impregnated with tetracycline. The post-deposition suspension liquid was poured off and the absorbance at 360 nm was measured using a UV-vis. The absorbance was found to correspond to a value of 62 µg/ml, down from 80 µg/ml, indicating that tetracycline had been incorporated into the EPD membrane and had been removed from the suspension. Additionally, the membrane had taken on a yellow colour, the colour of tetracycline, indicating that the drug had been incorporated into the membrane.

Example 20—Investigation of Suitability of Collagen Membranes for Various Applications The ultimate tensile strength (UTS) of a hydrated collagen membrane produced by EPD according to the present invention and crosslinked with riboflavin was also tested, and determined as 3.73±0.15 MPa.

Assuming a thin walled cylinder:

$$\sigma_\theta = \frac{Pr}{t}$$

Where:
P is the internal pressure
t is the wall thickness
r is the mean radius of the cylinder.
$\sigma_\theta$ is the hoop stress.

Assuming a cylinder with diameter 4.5 mm (equivalent to the lumen of an artery), t=100 µm, and set $\sigma\theta=\sigma_{UTS}$ it is found that the theoretical maximum pressure an EPD membrane could withstand based on these values is P=166 kPa. This theoretical burst pressure is significantly above the 13 kPa pressure of the arterial system.

Additionally, the ability of an EPD collagen membrane to contain water was tested by placing a membrane over a beaker filled with water and inverting the beaker. The beaker was left for 7 days and examined each day to determine if water was able to leak through. The chamber was examined each day to check for leaks. After 7 days no fluid had leaked through the EPD membrane.

Figure 34:
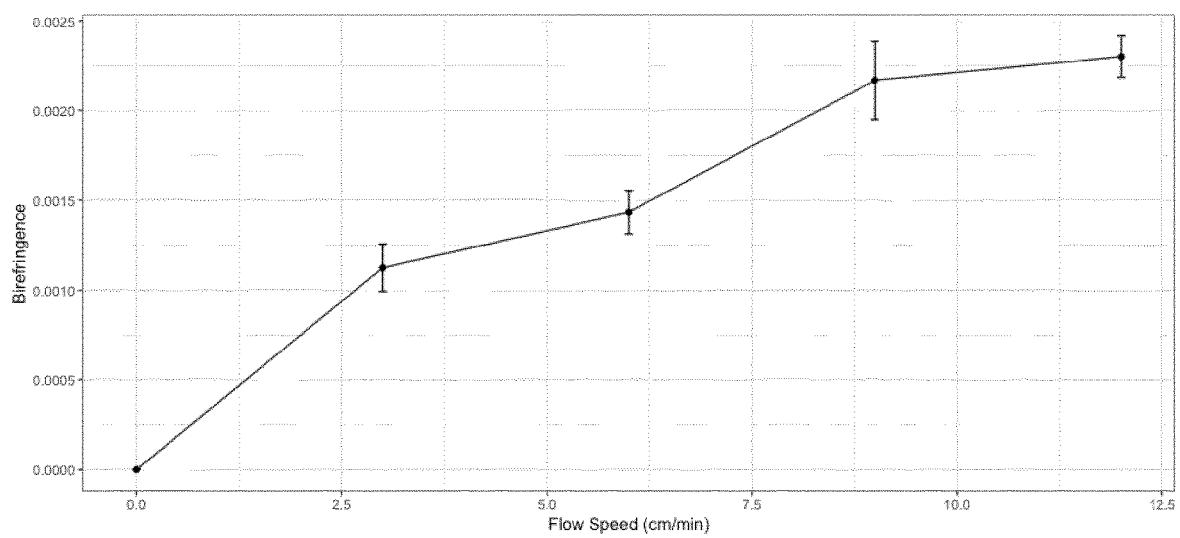
FIG. 34 is a graph of birefringence vs deposition flow speed (cm/min) for collagen films produced by EPD.

These results indicate that EPD collagen membranes produced according to the present invention are suitable for applications such as containing bodily fluids during surgery, use as a patch to stop blood loss, or use as a venous or arterial replacement Example 20—Investigation of the Effect of Deposition Parameters on the Birefringence of Collagen Membranes The birefringence was measured (using protocol 'B' discussed above) of samples produced at 10V pulsed current EPD at a range of different flow speeds. It was found that the birefringence of the samples increased with increasing flow speeds, as can be seen in FIG. 34, a graph of flow speed (cm/min) against Birefringence.

Figure 35:
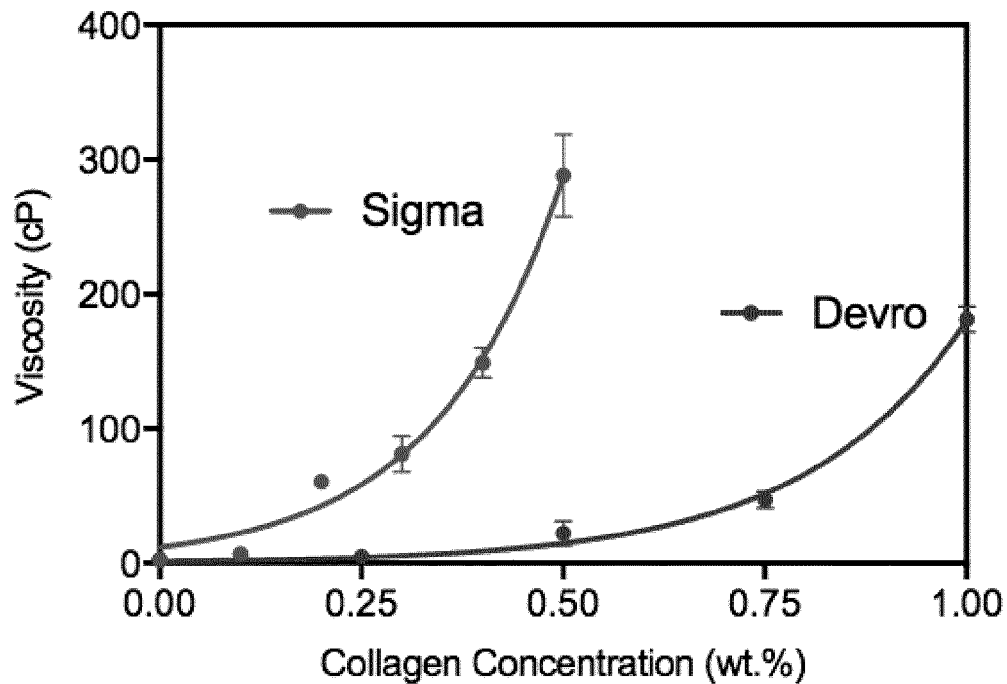
FIG. 35 is a graph showing variation in Viscosity (cP) of collagen suspensions with collagen concentration (wt %).

How the viscosity of the collagen suspension affects the birefringence of samples was also investigated. The viscosity of the collagen suspension can be manipulated by changing the concentration of collagen, as depicted in FIG. 35, a graph showing Viscosity (cP) as a function of collagen concentration (wt %). 'Sigma' and 'Devro' lines on this graph refer to original collagen sources, Sigma is sourced from Sigma Aldrich (Code: C9879), and Devro is collagen sourced from Devro Plc.

Viscosities measurements were obtained using the following protocol:
  Collagen suspensions were prepared as described above, using acetic acid and ethanol, but at varying concentrations of collagen.
  Viscosity measurements of the suspensions were taken using a rheometer:
    0.5 ml of collagen suspension was pipetted into the base of the rheometer, and the rheometer was sealed shut before running.
    For each measurement, a CPA-40Z disc/spindle was used, the temperature was 23.1° C., the speed was 5 rpm, the shear rate was 37.5/s, and the conditioning time was 30 seconds.

Figure 36:
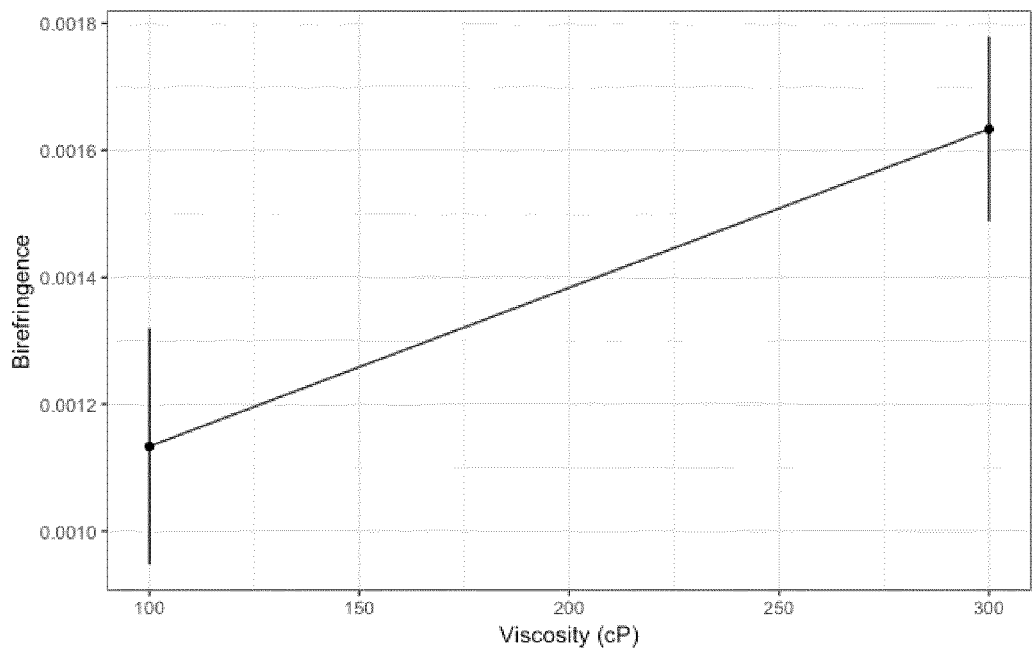
FIG. 36 is a graph of birefringence vs Viscosity (cP) for collagen films produced by EPD.

Collagen membranes were produced from collagen suspensions with different viscosities, where all other parameters remained the same: 10V pulsed current, and a flow speed of 5 cm/min. Preliminary results suggest that increasing the viscosity of the suspensions increases the birefringence of the collagen membranes produced, as shown in FIG. 36. Based on these measurements, a preferred range of viscosity of collagen suspension for generating alignment can be selected as between 50-400 cP, preferably between 100 and 300 cP.

Example 21—Investigation into Controlling Density of Collagen Membranes

Figure 37:
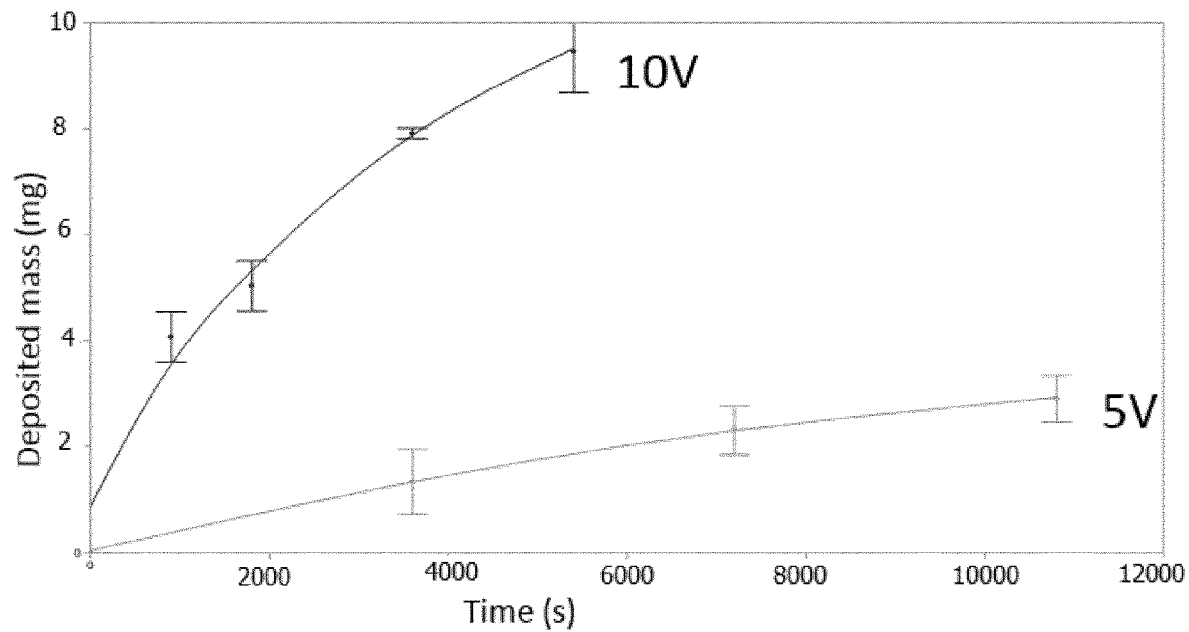
FIG. 37 is a graph of deposited mass (mg) over time for two different EPD voltages (5 V and 10V)

The density of the collagen membranes produced by EPD can be controlled by changing the rate of deposition. The rate at which collagen deposits increases with increasing deposition voltage, as shown in FIG. 37, which shows the deposited mass of collagen during EPD for deposition voltages of 5V and 10V. Without wishing to be bound by theory, the inventors suggest that when the collagen deposits at an increased rate, with increased force, it will pack together more tightly when depositing, thus leading to increased density.

Collagen membranes were produced using a range of deposition voltages and measured the density of said membranes with the following method:
  Collagen was deposited under normal pulsed current parameters, but at varying voltages.
  Collagen membranes were dried and weighed.
  The lengths and widths of the membranes were measured with a calliper, and the thicknesses were measured with a micrometer. With these the volume of each membrane was determined.
  The density of each membrane was then calculated using the volume and mass:

$$\text{Density} = \frac{\text{Mass}}{\text{Volume}}$$

Figure 38:
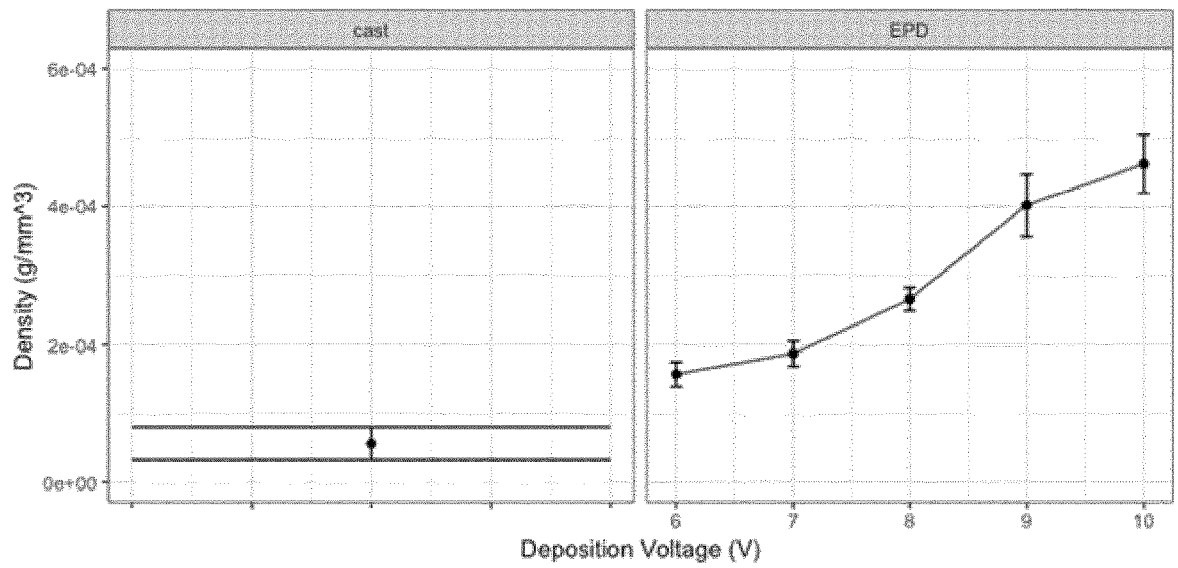
FIG. 38 shows (a) density of a cast collagen membrane and (b) variation in density (g/mm$^3$) with deposition voltage for EPD collagen membranes.

The results are shown in FIG. 38. It can be seen that the density of the deposited membranes increased from about 1.6 e-04 for a deposition voltage of 6 V, up to about 4.5e-04 for a deposition voltage of 10 V. These densities were also higher than for cast films. The results show that the density of collagen membranes produced using EPD can be altered, which is not possible for cast membranes.

Figure 23:
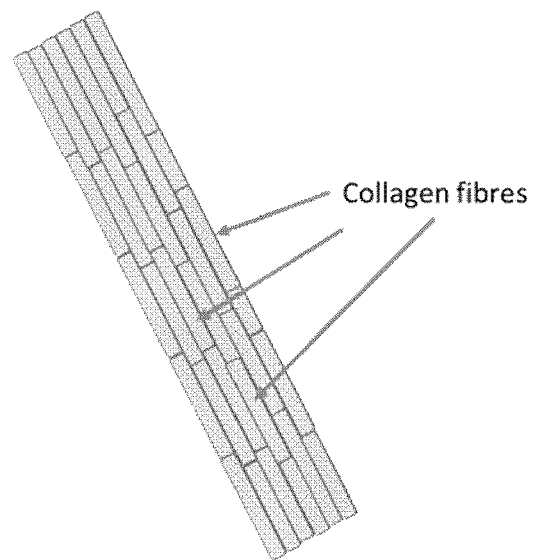
FIG. 23 shows a schematic drawing of the lamellar structure formed by the collagen fibres in a membrane produced by EPD.
Figure 24:
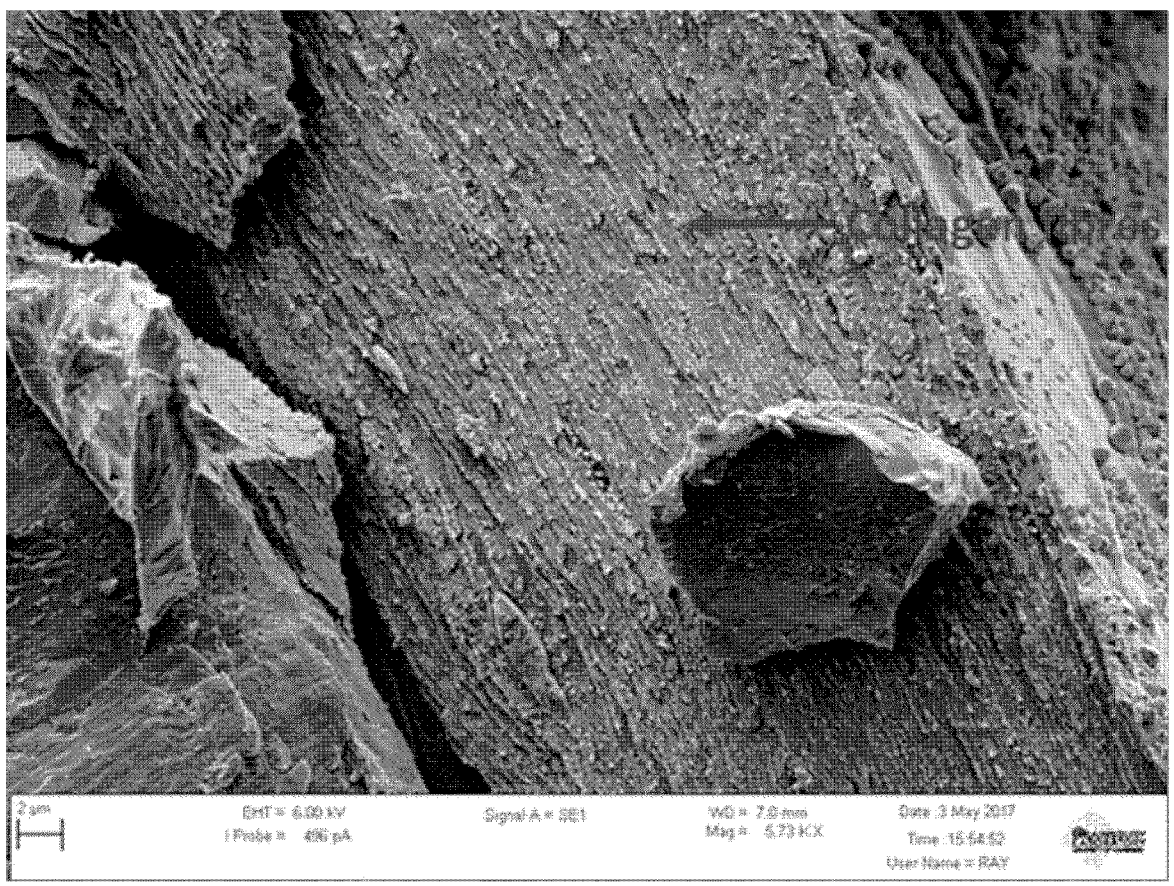
FIG. 24 shows an SEM cross section of a hydrated aligned collagen membrane produced by EPD. The fibre structure is densely packed.

FIG. 23 shows a schematic drawing of the lamellar structure formed by the collagen fibres in a membrane produced by EPD. FIG. 24 shows an SEM cross section of a hydrated collagen membrane produced by EPD. The fibre structure is densely packed. For membranes formed of two or more collagen films of different degrees and/or directions of alignment, the differences in alignment between difference layers can be seen by fracture the membrane after freezing in liquid nitrogen. The fracture surfaces are then examined using SEM. A suitable protocol comprises the steps:

Immerse membrane sample in liquid nitrogen until the sample is frozen.

The membrane is then fractured using a knife or other instrument.

The membrane is mounted on an SEM stub with the fracture surface upturned.

The membrane is coated in gold, carbon, or other conductive material by sputter coating The edge of the membrane is imaged using a SEM, where the different orientations of the fibres in each layer can be observed.

Figure 25:
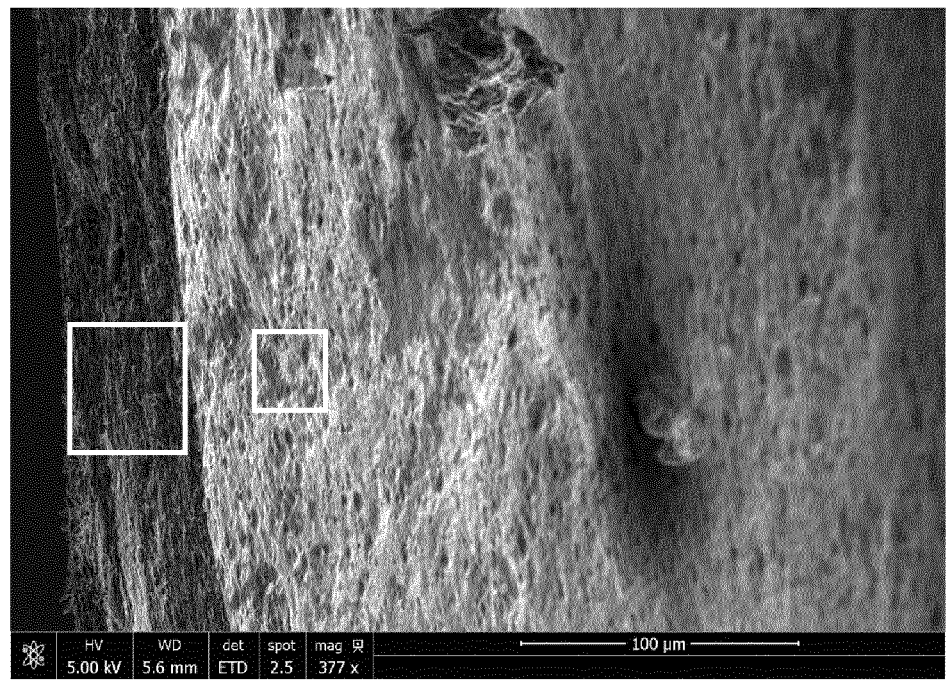
FIG. 25 shows an electron microscopy image of a collagen membrane prepared by EPD at low magnification, showing the edge and surface of the membrane.
Figure 26:
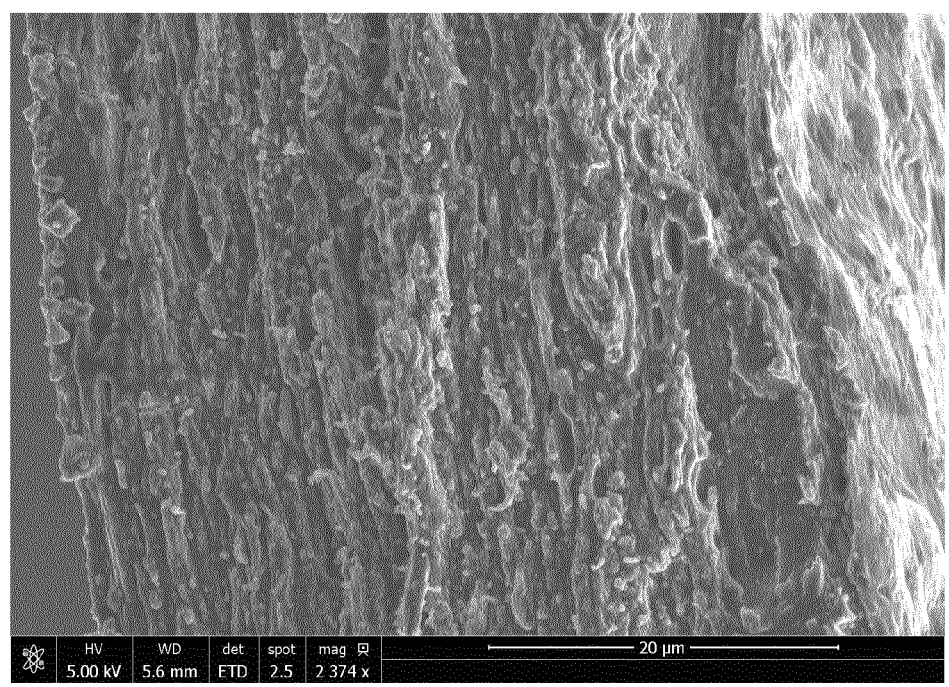
FIG. 26 shows a higher magnification image of the membrane of FIG. 25, indicated by the larger white box on FIG. 25, FIG. 26 showing the lamellar structure.
Figure 27:
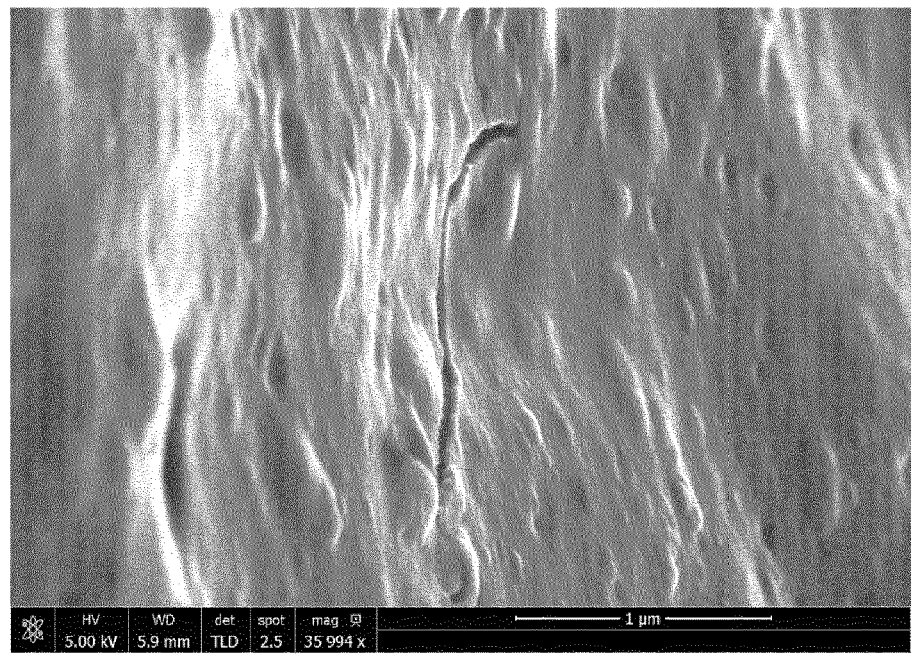
FIG. 27 shows a higher magnification image of the surface of the collagen membrane of FIG. 25, indicated by the smaller white box on FIG. 25, FIG. 27 showing almost no surface porosity.

It is of interest here to consider the morphological differences between embodiments of the present invention and prior art approaches in which collagen monomers in solution are deposited using electrochemical compaction, causing films to form at the isoelectric point between electrodes. Subsequently, a step is then carried out to induce fibrillogenesis. Membranes formed using such an approach tend to have a higher porosity than membranes formed using the disclosure set out here. Reference 39 shows electron microscopy images of such collagen films, but in non-hydrated format. In order to enable a like-for-like comparison, FIG. 25-27 show a collagen membrane prepared by EPD according to an embodiment of the invention, but in non-hydrated (i.e. dry) form. FIG. 25 shows the collagen membrane prepared by EPD at low magnification, showing the edge and surface of the membrane. FIG. 26 shows a higher magnification image of the membrane of FIG. 25, indicated by the larger white box on FIG. 25. The lamellar structure of the film can be seen in FIG. 26. FIG. 27 shows a higher magnification image of the surface of the collagen membrane of FIG. 25, indicated by the smaller white box on FIG. 25. As can be seen in FIG. 27, the film has almost no surface porosity.

By careful choice of deposition parameters such as voltage, pulse width, and duty cycle, it was shown that macroscopically defect free films of collagen can be produced from an aqueous suspension by Pulsed-EPD. The deposition rate was found to be greater at higher voltages, and deposition of multiple suspensions onto a single electrode was found to increase the mass linearly. Investigation of the microstructure showed minor differences in surface morphology between collagen membranes formed by solvent casting and by Pulsed-EPD, and the internal structure of hydrated collagen membranes was found to be densely packed, with a small number of nano-scale voids. Membranes produce by Pulsed-EPD could be mechanically separated from electrodes easily after drying with no visible damage.

We demonstrated the ability to deposit HyA by both DC-EPD and Pulsed-EPD. The deposition rate was higher at greater voltages, and it was only possible to produce macroscopically defect free films of hyaluronic acid by Pulsed-EPD. Sequential deposition of collagen and hyaluronic acid layers by Pulsed-EPD was found to result in a multilayer film consisting of well defined, separate layers of collagen and hyaluronic acid. The deposition rate and thickness that could be achieved was found to be unaffected by prior depositions of collagen and HyA layers. Investigation of hydrated multilayer films showed that the HyA layer comprised a dense hydrogel, and the collagen layer comprised a lamellar structure of collagen fibres. Micro voids were found within both the collagen and hyaluronic acid layers, indicating that micro-scale bubbles had formed during deposition but had not coagulated into macroscopic, damaging bubbles. We have demonstrated a method of producing complex multilayer membranes from biomolecules that can be used to produce films of tailored thickness, chemistry, and complexity, that can be generalised to produce materials highly tailored to clinical requirements.

NON-PATENT REFERENCES

[1] S. F. Badylak et al., "The use of xenogeneic small intestinal submucosa as a biomaterial for Achilles tendon repair in a dog model.", *J. Biomed. Mater. Res.* 29 977-85, 1995

[2] Steven F. S. "The effect of chelating agents on collagen interfibrillar matrix interactions in connective tissue", Biochim. Biophys. Acta 140, 522-528, 1967

[3] Schofield, J. D. et al, "The Isolation, and Amino Acid and Carbohydrate Composition of Polymeric Collagens Prepared from Various Human Tissues" Biochem. J. 124, 467-473, 1971

[4] Steven, F. S. et al, "Polymeric collagen isolated from the human intestinal submucosa", Gut 10, 484-487, 1969

[5] Brown et al, Adv Funct Mater 25 2762-1770, 2005

[6] K. Panduranga Rao, "Recent developments of collagen-based materials for medical applications and drug delivery systems," *J. Biomater. Sci. Polym. Ed.*, vol. 7, pp. 623-645, January 1996.

[7] V. A. Kumar, J. M. Caves, C. A. Haller, E. Dai, L. Liu, S. Grainger, and E. L. Chaikof, "Collagen based substrates with tunable strength for soft tissue engineering," *Biomater. Sci.*, vol. 1, no. 11, p. 1193, 2013.

[8] A. Sculean, R. Gruber, and D. D. Bosshardt, "Soft tissue wound healing around teeth and dental implants," *J. Clin. Periodontol.*, vol. 41 Suppl 1, pp. S6-22, April 2014.

[9] V. A. Perumal, T. Govender, D. Lutchman, and I. Mackraj, "Investigating a New Approach to Film Casting for Enhanced Drug Content Uniformity in Polymeric Films," *Drug Dev. Ind. Pharm.*, vol. 34, pp. 1036-1047, January 2008.

[10] L.-Q. Wu, A. P. Gadre, H. Yi, M. J. Kastantin, G. W. Rubloff, W. E. Bentley, G. F. Payne, and R. Ghodssi, "Voltage-Dependent Assembly of the Polysaccharide Chitosan onto an Electrode Surface," *Langmuir*, vol. 18, pp. 8620-8625, October 2002.

[11] T. Jiang, Z. Zhang, Y. Zhou, Y. Liu, Z. Wang, H. Tong, X. Shen, and Y. Wang, "Surface functionalization of titanium with chitosan/gelatin via electrophoretic deposition: characterization and cell behavior," *Biomacromolecules*, vol. 11, pp. 1254-60, May 2010.

[12] J. Zhang, Z. Wen, M. Zhao, G. Li, and C. Dai, "Effect of the addition CNTs on performance of CaP/chitosan/ coating deposited on magnesium alloy by electrophoretic deposition," *Mater. Sci. Eng. C*, vol. 58, pp. 992-1000, January 2016.

[13] P. Benzoni, P. Ginestra, L. Altomare, A. Fiorentino, L. De Nardo, E. Ceretti, and P. Dell'Era, "Biomanufacturing of a Chitosan/Collagen Scaffold to Drive Adhesion and Alignment of Human Cardiomyocyte Derived from Stem Cells," *Procedia CIRP*, vol. 49, pp. 113-120, 2016.

[14] X. Pang and I. Zhitomirsky, "Electrophoretic deposition of composite hydroxyapatite-chitosan coatings," *Mater. Charact.*, vol. 58, no. 4, pp. 339-348, 2007.

[15] W.-W. Li, H.-Y. Wang, and Y.-Q. Zhang, "A novel chitosan hydrogel membrane by an improved electrophoretic deposition and its characteristics in vitro and in vivo," *Mater. Sci. Eng. C*, vol. 74, pp. 287-297, May 2017.

[16] I. Zhitomirsky and L. Gal- or, "Electrophoretic deposition of hydroxyapatite," *J. Mater. Sci. Mater. Med.*, vol. 8, pp. 213-219, April 1997.

[17] O. Albayrak, O. El-Atwani, and S. Altintas, "Hydroxyapatite coating on titanium substrate by electrophoretic deposition method: Effects of titanium dioxide inner layer on adhesion strength and hydroxyapatite decomposition," *Surf. Coatings Technol.*, vol. 202, pp. 2482-2487, February 2008.

[18] X. F. Xiao and R. F. Liu, "Effect of suspension stability on electrophoretic deposition of hydroxyapatite coatings," *Mater. Lett.*, vol. 60, pp. 2627-2632, September 2006.

[19] F. Frajkorov'a, E. Molero, P. Montero, M. C. Gomez-Guillen, A. J. Sanchez-Herencia, and B. Ferrari, "Biodegradable bi-layered coatings shaped by dipping of Ti films followed by the EPD of gelatin/hydroxyapatite composites," *J. Eur. Ceram. Soc.*, vol. 36, pp. 343-355, January 2016.

[20] Y. Göncü, M. Geggin, F. Bakan, and N. Ay, "Electrophoretic deposition of hydroxyapatitehexagonal boron nitride composite coatings on Ti substrate," *Mater. Sci. Eng. C*, vol. 79, pp. 343-353, October 2017.

[21] V. A. Webster, E. L. Hawley, O. Akkus, H. J. Chiel, and R. D. Quinn, "Fabrication of Electrocompacted Aligned Collagen Morphs for Cardiomyocyte Powered Living Machines," in *Conf. Biomim. Biohybrid Syst. Living Mach. 2015 Biomim. Biohybrid Syst.*, pp. 429-440, Springer International Publishing, 2015.

[22] V. A. Webster, E. L. Hawley, O. Akkus, H. J. Chiel, and R. D. Quinn, "Effect of actuating cell source on locomotion of organic living machines with electrocompacted collagen skeleton," *Bioinspir. Biomim.*, vol. 11, p. 036012, May 2016.

[23] X. Cheng, U. A. Gurkan, C. J. Dehen, M. P. Tate, H. W. Hillhouse, G. J. Simpson, and O. Akkus, "An electrochemical fabrication process for the assembly of anisotropically oriented collagen bundles," *Biomaterials*, vol. 29, no. 22, pp. 3278-3288, 2008.

[24] H. R. Baker, E. F. M. S, and K. M. Poduska, "Electrochemically controlled growth and positioning of suspended collagen membranes," *Langmuir*, vol. 24, pp. 2970-2, April 2008.

[25] A. R. Boccaccini, S. Keim, R. Ma, Y. Li, and I. Zhitomirsky, "Electrophoretic deposition of biomaterials," *J. R. Soc. Interface*, vol. 7 Suppl 5, pp. S581-613, October 2010.

[26] K. Mazloomi, N. B. Sulaiman, and H. Moayedi, "Electrical Efficiency of Electrolytic Hydrogen Production," *Int. J. Electrochem. Sci*, vol. 7, pp. 3314-3326, 2012.

[27] L. Besra, T. Uchikoshi, T. S. Suzuki, and Y. Sakka, "Bubble-Free Aqueous Electrophoretic Deposition (EPD) by Pulse-Potential Application," *J. Am. Ceram. Soc.*, vol. 91, pp. 3154-3159, October 2008.

[28] T. Uchikoshi, K. Ozawa, B. D. Hatton, and Y. Sakka, "Dense, bubble-free ceramic deposits from aqueous suspensions by electrophoretic deposition," J. Mater. Res., vol. 16, pp. 321-324, February 2001.

[29] J. Tabellion and R. Clasen, "Electrophoretic deposition from aqueous suspensions for near-shape manufacturing of advanced ceramics and glasses applications," *J. Mater. Sci.*, vol. 39, pp. 803-811, February 2004.

[30] O. Sakurada, K. Suzuki, T. Miura, and M. Hashiba, "Bubble-free electrophoretic deposition of aqueous zirconia suspensions with hydroquinone," *J. Mater. Sci.*, vol. 39, pp. 1845-1847, March 2004.

[31] A. Nold and R. Clasen, "Bubble-free electrophoretic shaping from aqueous suspension with micro point-electrode," *J. Eur. Ceram. Soc.*, vol. 30, pp. 2971-2975, October 2010.

[32] B. Neirinck, J. Fransaer, O. V. der Biest, and J. Vleugels, "Aqueous electrophoretic deposition in asymmetric AC electric fields (ACEPD)," *Electrochem. commun.*, vol. 11, pp. 57-60, January 2009.

[33] K. Raju and D. Yoon, "Electrophoretic deposition of BaTiO3 in an aqueous suspension using asymmetric alternating current," *Mater. Lett.*, vol. 110, pp. 188-190, November 2013.

[34] F. Caubert, P.-L. Taberna, and L. Arurault, "Innovating pulsed electrophoretic deposition of boehmite nanoparticles dispersed in an aqueous solution, into a model porous anodic film, prepared on aluminium alloy 1050," *Surf. Coatings Technol.*, vol. 302, pp. 293-301, 2016.

[35] L. Besra, T. Uchikoshi, T. Suzuki, and Y. Sakka, "Application of constant current pulse to suppress bubble incorporation and control deposit morphology during aqueous electrophoretic deposition (EPD)," *J. Eur. Ceram. Soc.*, vol. 29, pp. 1837-1845, July 2009.

[36] D. Nečas and P. Klapetek, "Gwyddion: an open-source software for SPM data analysis," Cent. *Eur. J. Phys*, vol. 10, no. 1, pp. 181-188, 2012.

[37] L. Besra and M. Liu, "A review on fundamentals and applications of electrophoretic deposition (EPD)," *Prog. Mater. Sci.*, vol. 52, no. 1, pp. 1-61, 2007.

[38] US20100311949A1

[39] Younesi M, Islam A, Kishore V, Panit S, Akkus O., Fabrication of compositionally and topographically complex robust tissue forms by 3D-electrochemical compaction of collagen, Biofabrication. 2015 Jun. 12; 7(3): 035001. doi: 10.1088/1758-5090/7/3/035001.

The invention claimed is:

1. A method of manufacturing a layer comprising an array of fibres of collagen, the method comprising:
providing a suspension of insoluble collagen fibres;
providing a layer deposition interface;
applying an electric field across the suspension to cause electrophoretic deposition of the insoluble collagen fibres at the layer deposition interface, thereby building up a layer comprising deposited collagen,
wherein the electric field is pulsed in order to subject the suspension to pulsed electrophoresis, the electric field strength being in the range 100-2000V/m, the average pulse length being in the range 10-100 ms and a duty cycle being 20-70%, and wherein the method further comprises causing relative movement, in a relative movement direction, between the layer deposition interface and the suspension, thereby causing alignment of the collagen fibres in the layer, the fibres being substantially aligned within the layer along a first in-plane direction substantially parallel to the relative movement direction.

2. The method according to claim 1 wherein the duty cycle is 30-60%.

3. The method according to claim 1 wherein the electric field is applied between opposing electrodes, the potential difference between the electrodes being at most 20 V.

4. The method according to claim 1, wherein the electric field is applied between, opposing electrodes, wherein at least one of the opposing electrodes in is contact with the suspension, a surface of the electrode providing the layer deposition interface.

5. The method according to claim 1, the method further comprising lyophilising the layer comprising an array of fibres of collagen.

6. The method according to claim 1, the method further comprising steps of drying the layer comprising an array of fibres of collagen to form a collagen membrane, disposing the collagen membrane within a mould, at least partially filling the mould with a suspension of insoluble collagen fibres, and lyophilising of the mould containing the suspension of insoluble collagen fibres and the collagen membrane to thereby form a porous collagen scaffold incorporating the collagen membrane.

7. The method according to claim 1, wherein the suspension of insoluble collagen fibres further comprises viable mammalian cells, such that the cells are embedded in the layer during the electrophoretic deposition of the insoluble collagen fibres.

8. The method according to claim 1, wherein the layer deposition interface comprises a surface of a release layer.

9. The method according to claim 1 wherein the suspension of insoluble collagen fibres further comprises one or more therapeutic compounds, such that the one or more therapeutic compounds are comprised in the layer during the electrophoretic deposition of the insoluble collagen fibres.

10. The method according to claim 1 wherein, after deposition of the layer comprising deposited collagen, the relative movement direction is changed, in order to deposit a subsequent layer in which the fibres are substantially aligned within the layer along a second in-plane direction, not parallel with the first in-plane direction.

11. A method of manufacturing a layer comprising an array of fibres of collagen, the method comprising:
providing a suspension of insoluble collagen fibres;
providing a layer deposition interface;
applying an electric field across the suspension to cause electrophoretic deposition of the insoluble collagen fibres at the layer deposition interface, thereby building up a layer comprising deposited collagen,
wherein the layer deposition interface is provided by a membrane or scaffold having opposing major surfaces, the membrane or scaffold being supported by the suspension by at least one of the major surfaces of the membrane or scaffold being in contact with the suspension, and wherein the method further comprises causing relative movement, in a relative movement direction, between the layer deposition interface and the suspension, thereby causing alignment of the collagen fibres in the layer, the fibres being substantially aligned within the layer along a first in-plane direction substantially parallel to the relative movement direction.

12. The method according to claim 11 wherein the layer deposition interface is provided by a collagen membrane and the collagen membrane is held within the suspension with both of the major surfaces of the membrane being in contact with the suspension.

13. The method according to claim 11, the method further comprising lyophilising the layer comprising an array of fibres of collagen.

14. The method according to claim 11, the method further comprising steps of drying the layer comprising an array of fibres of collagen to form a collagen membrane, disposing the collagen membrane within a mould, at least partially filling the mould with a suspension of insoluble collagen fibres, and lyophilising of the mould containing the suspension of insoluble collagen fibres and the collagen membrane to thereby form a porous collagen scaffold incorporating the collagen membrane.

15. The method according to claim 11, wherein the suspension of insoluble collagen fibres further comprises viable mammalian cells, such that the cells are embedded in the layer during the electrophoretic deposition of the insoluble collagen fibres.

16. The method according to claim 11, wherein the layer deposition interface comprises a surface of a release layer.

17. The method according to claim 11 wherein the suspension of insoluble collagen fibres further comprises one or more therapeutic compounds, such that the one or more therapeutic compounds are comprised in the layer during the electrophoretic deposition of the insoluble collagen fibres.

18. The method according to claim 11 wherein, after deposition of the layer comprising deposited collagen, the relative movement direction is changed, in order to deposit a subsequent layer in which the fibres are substantially aligned within the layer along a second in-plane direction, not parallel with the first in-plane direction.

* * * * *